(12) United States Patent
Lenhard et al.

(10) Patent No.: US 6,983,753 B1
(45) Date of Patent: Jan. 10, 2006

(54) INFRARED THERMOGRAPHY

(75) Inventors: James Martin Lenhard, Durham, NC (US); Mark Andrew Paulik, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 498 days.

(21) Appl. No.: 10/129,880

(22) PCT Filed: Nov. 17, 2000

(86) PCT No.: PCT/US00/31755

§ 371 (c)(1),
(2), (4) Date: May 10, 2002

(87) PCT Pub. No.: WO01/35819

PCT Pub. Date: May 25, 2001

Related U.S. Application Data

(63) Continuation-in-part of application No. 09/441,493, filed on Nov. 17, 1999.

(51) Int. Cl.
*A61B 19/00* (2006.01)

(52) U.S. Cl. .................. 128/898; 600/474; 600/549
(58) Field of Classification Search ............. 128/898; 600/407, 412, 473, 474, 549; 436/147
See application file for complete search history.

(56) References Cited

FOREIGN PATENT DOCUMENTS

GB 2311368 A 9/1997

*Primary Examiner*—Corrine McDermott
*Assistant Examiner*—William H Matthews
(74) *Attorney, Agent, or Firm*—Michael M. Conger

(57) ABSTRACT

The present invention relates, in general, to thermography and, in particular, to a method of using infrared thermography to monitor physiological and molecular events that elicit a thermogenic response in animals (including humans), plants, tissues, cells and cell-free systems. The present method can be used for screening, identifying, and ranking drug candidates for multiple diseases, disorders and conditions.

5 Claims, 46 Drawing Sheets

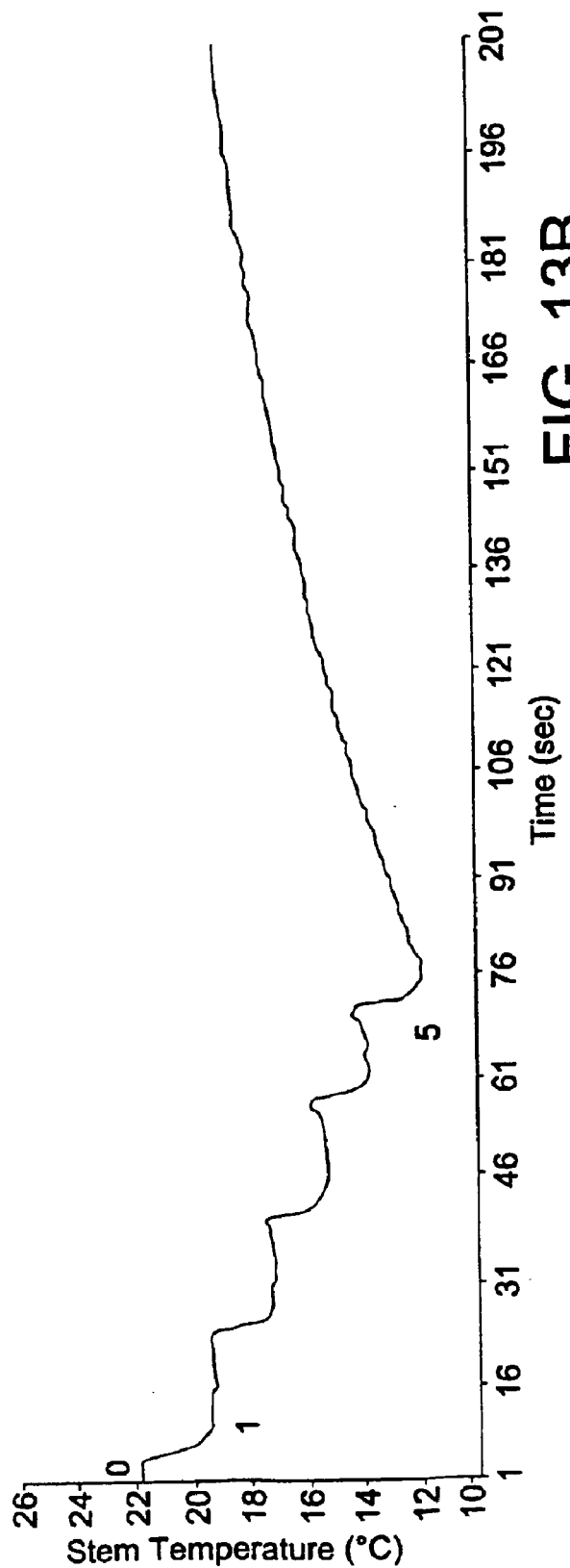

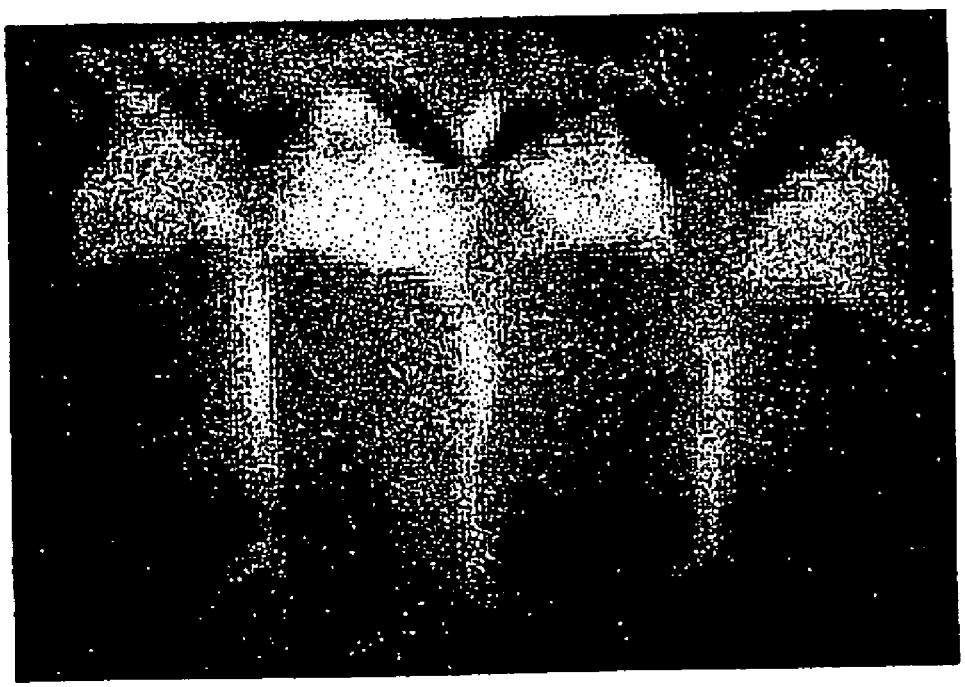
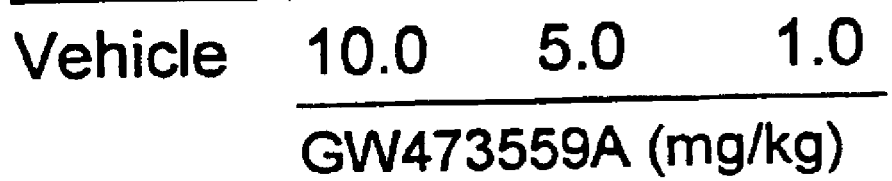
FIG. 15A.

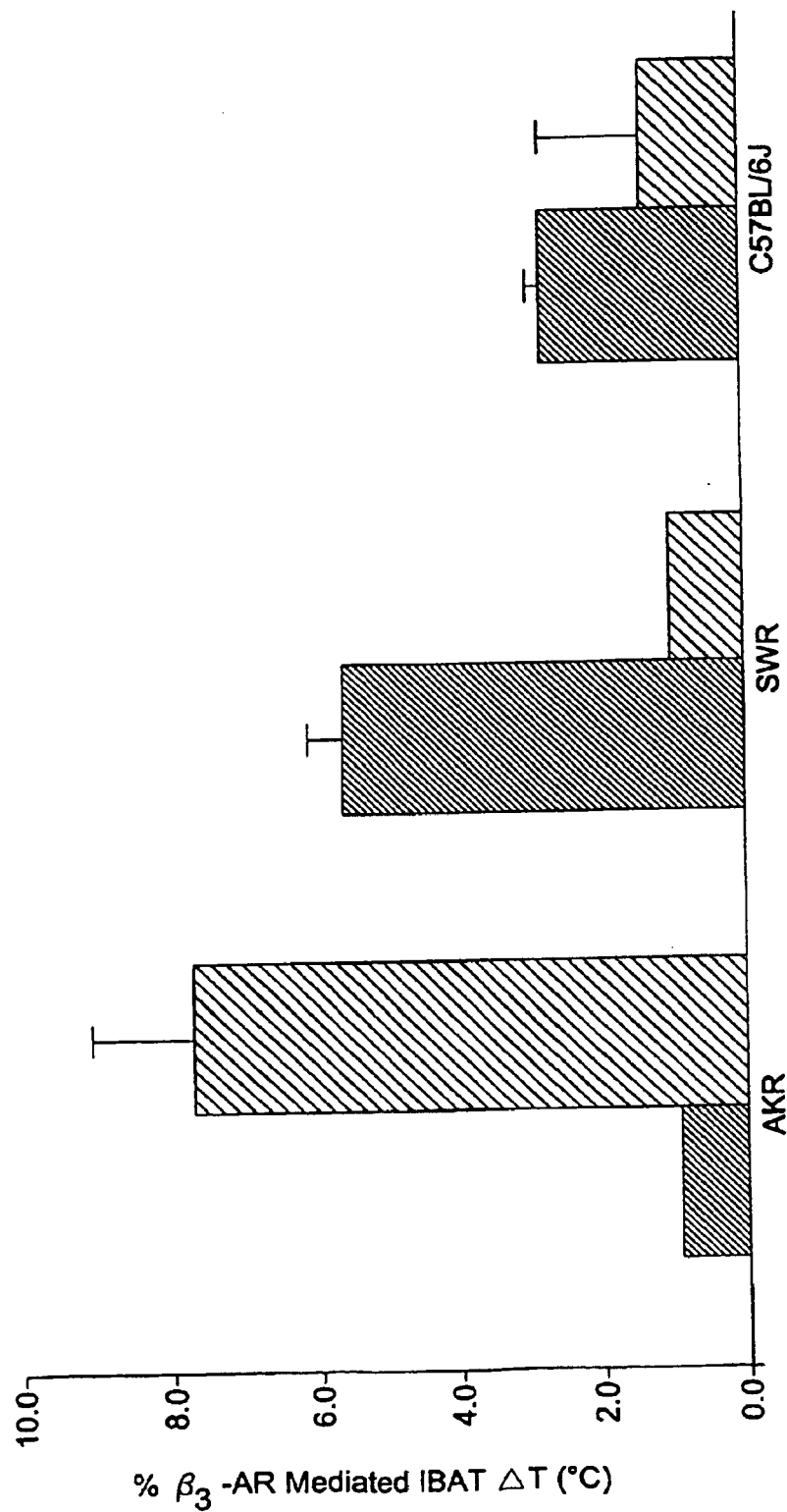

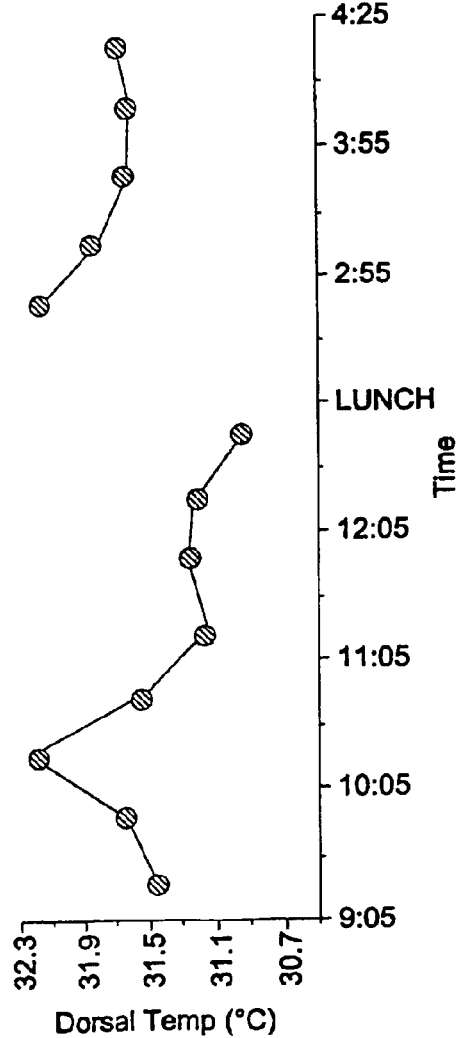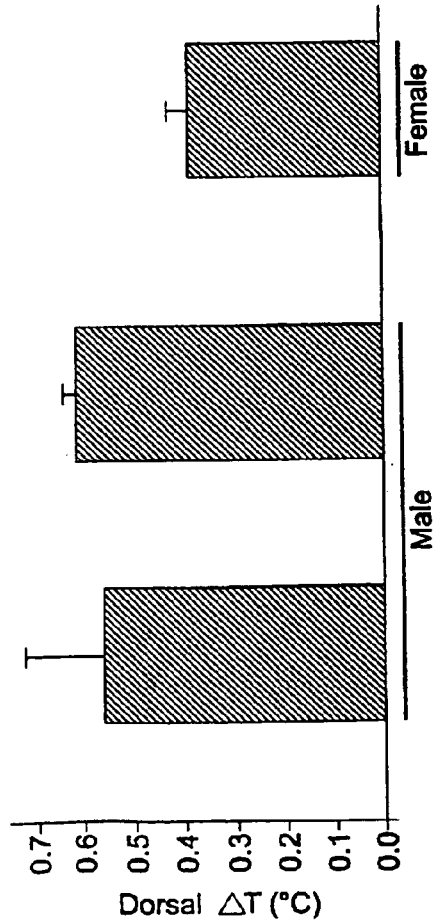

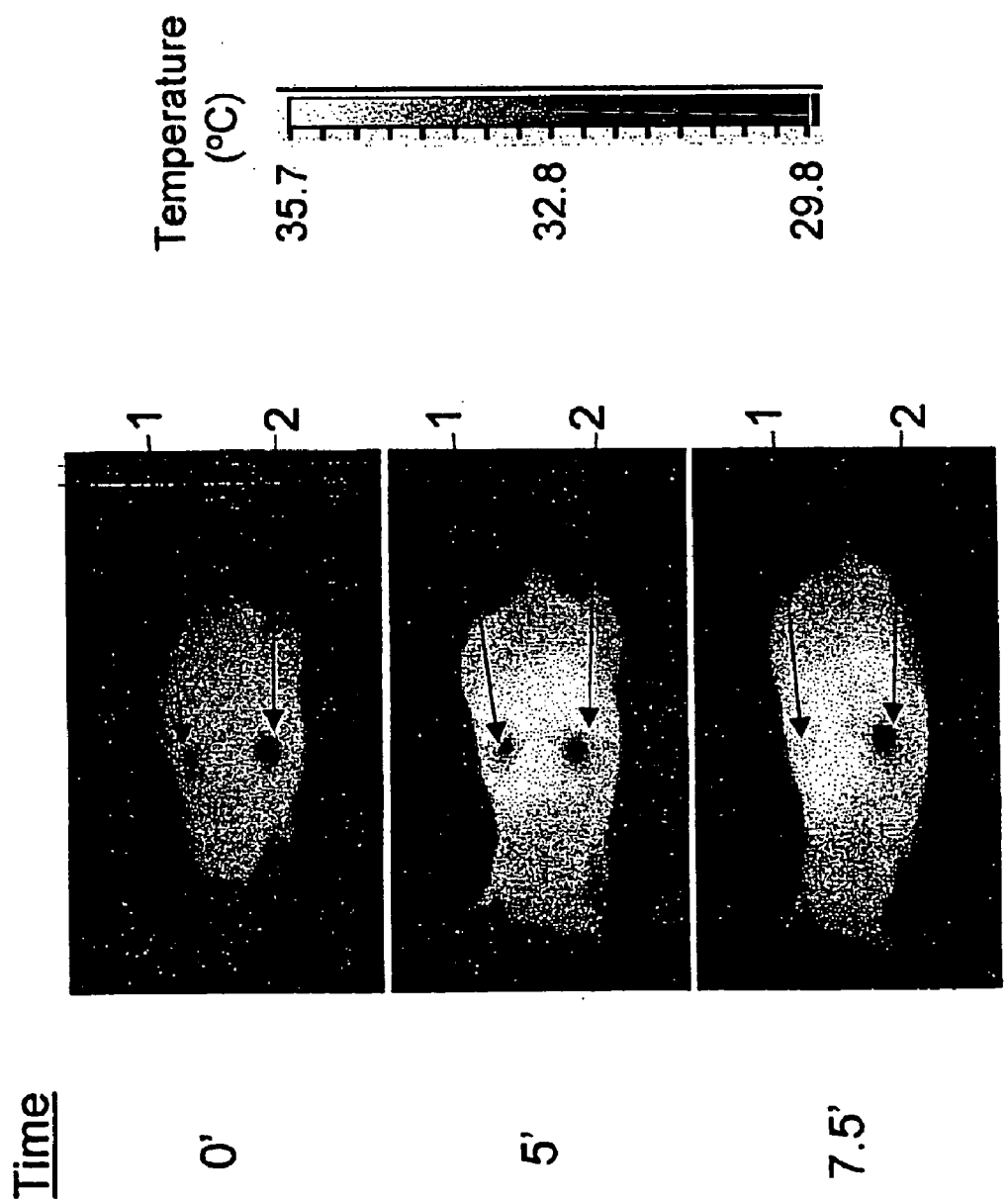

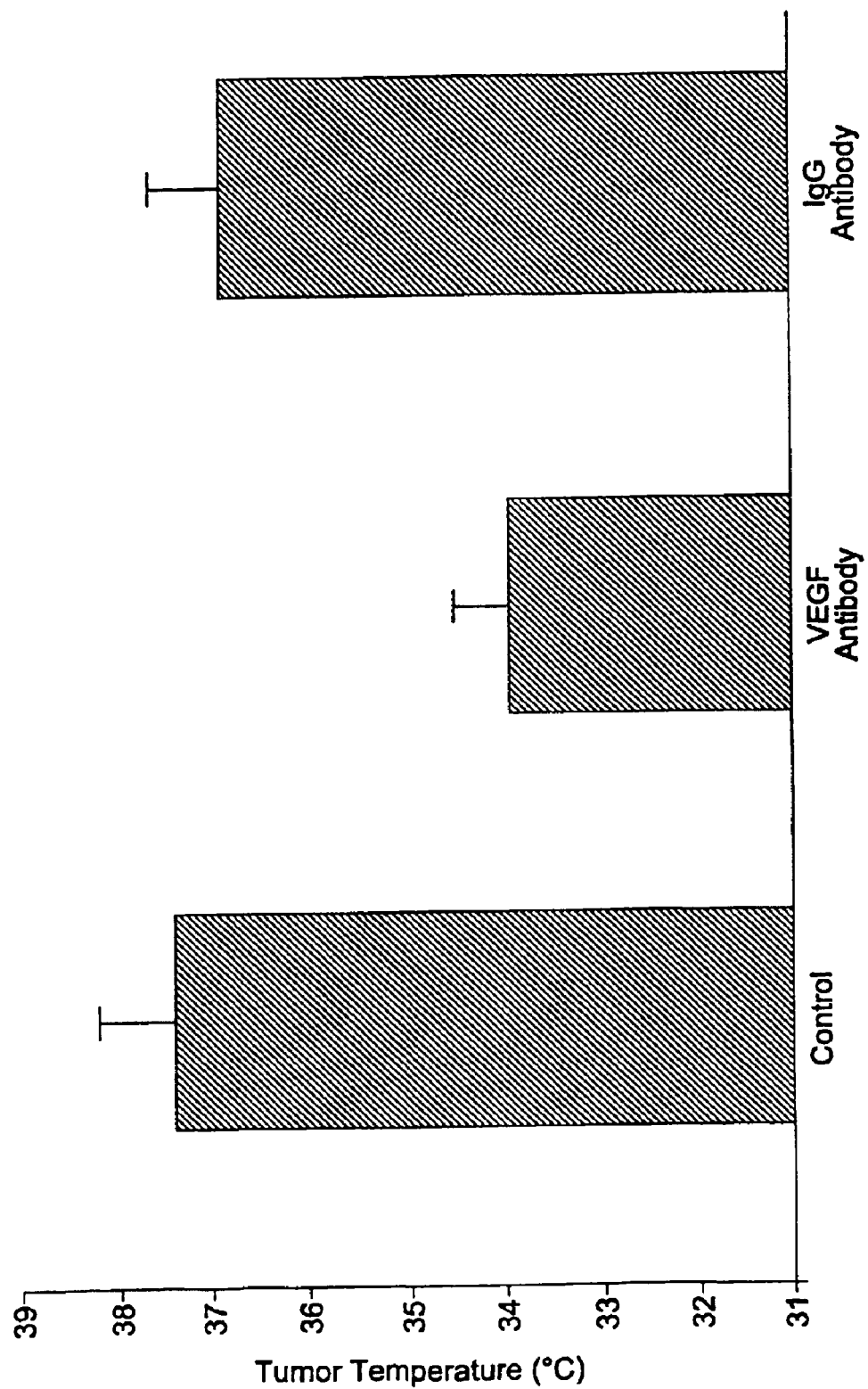

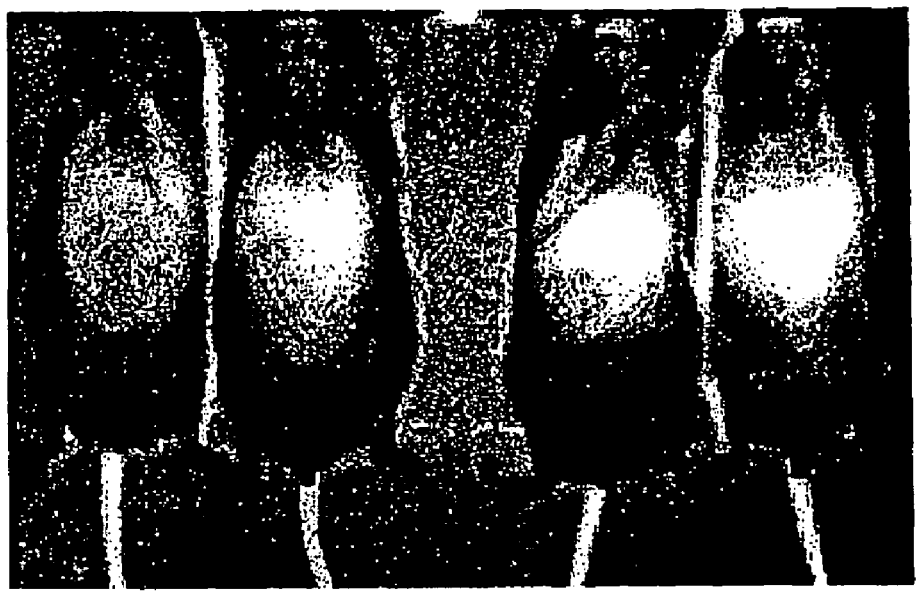
control 0.1 0.3 1.0
Lipopolysacharide (mg/kg)
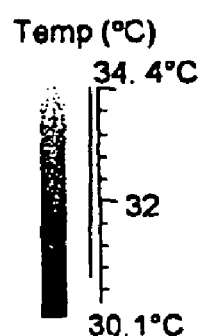
FIG. 29A.

INFRARED THERMOGRAPHY

This application is filed pursuant to 35 U.S.C. § 371 as a United States National Phase Application of International Application No. PCT/US00/31755 filed 17 Nov. 2000, which is a continuation-in-part U.S. Ser. No. 09/441,493 filed 17 Nov. 1999.

TECHNICAL FIELD

The present invention relates, in general, to thermography and, in particular, to a method of using infrared thermography to monitor physiological and molecular events that elicit a thermogenic response in animals (including humans), plants, tissues, cells and cell-free systems. The present method can be used for screening, identifying, and ranking drug candidates for multiple diseases, disorders and conditions. It can also particularly advantageously be used to diagnose lipodystrophy syndrome in a patient.

BACKGROUND

Thermodynamics is a science concerned with relations between work and heat. Virtually every chemical reaction or physiological process in animals or cells occurs with the absorption or generation of heat and thus, any heat absorbed or generated by a system is proportional to the amount of work done. Consequently, measurement of heat output (i.e., thermogenesis) can be used to estimate the energy used in or produced by chemical reactions and physiological processes.

Various methods (e.g., Northern or Western-blotting) are available for detecting the expression of proteins that regulate thermogenesis in cells (e.g., uncoupling proteins, UCPs), but these methods are labor intensive and do not directly measure protein activity. Guanosine 5'-diphosphate (GDP)—binding assays and fluorescent dyes (e.g., JC-1 or rhodamine derivatives) provide a direct measure of UCP activity (Nedergaard and Cannon, Am. J. Physiol. 248(3 Pt 1):C365–C371 (1985); (Reers et al, Biochemistry 30:4480–4486 (1991)). However, GDP-binding assays require protein purification and use of dyes is limited because of non-selective staining, cytotoxicity, and metabolism of the dyes by cells. More importantly, all of these techniques fail to directly measure real-time fluctuations in thermogenesis and are invasive.

Bomb calorimeters and microcalorimeters provide a means for quantitatively measuring the heat generated or consumed by cultured cells (Bottcher and Furst, J. Biochem. Biophys. Methods 32:191–194 (1996)) or chemical reactions. However, despite recent progress in developing multichannel calorimeters, methods for rapidly analyzing changes in heat in multiple simultaneous reactions ($\geq 60$) are not available. Moreover, temperature gradations over fixed surface areas, such as those in cell culture plates or on the surface of skin, cannot be measured using calorimeters.

Infrared thermometers have been developed that can measure the magnitude of infrared energy emitted from a specific body site (e.g., the ear canal). These instruments, however, cannot be used to measure heat production of isolated cells, tissues, or chemical reactions and cannot provide real time measurements of heat output by multiple samples over extended periods of time. Moreover, these devices do not provide images over large surface areas.

Infrared interactance instruments have also been developed. Unlike infrared thermometers, these instruments contain diodes that emit near radiation at wavelengths of <1000 nm. Since these instruments measure the absorption of near infrared radiation, they do not provide an accurate measure of thermogenesis.

The present invention provides a rapid non-invasive method of measuring real-time thermogenesis in animals, plants, tissues and isolated cells, including cells in culture. This invention extends to molecular interactions, such as receptor-ligand binding, enzyme catalysis, and other chemical reactions that alter heat output. The present method, which is based on the use of infrared thermography, can be used to screen and identify drug candidates for treating various diseases, disorders and conditions. Additionally, the present method can be used to visualize thermal changes within an animal tissue or organ, which can have significant uses in monitoring various effects and reactions within a subject.

Body shape and metabolic changes associated with the use of retroviral therapies are causing increasing concern among physicians who treat patients with HIV/AIDS. These changes in metabolism are due to a lipodystrophy syndrome which is characterized by an increase in abdominal fat and loss of subcutaneous adipose depots (Carr A., et al. Lancet 353, 2093–2099 (1999)). The present method can also advantageously be used to diagnose lipodystrophy in a patient, in particular, well before pathophysiological data typically becomes available. Such a diagnostic would allow treatment at an earlier stage in progression of the syndrome.

SUMMARY OF THE INVENTION

The present invention relates generally to a method of monitoring physiological changes and molecular interactions using infrared thermography. Infrared thermography provides a non-invasive approach to analyze the effects of any of a variety of agents on heat production in animals, plants, cells in culture, and chemical reactions in cell-free systems. The invention makes it possible to screen compounds for their ability to alter heat dissipation, and to identify compounds that have application in the treatment of various diseases, disorder and conditions.

The present invention provides a method of diagnosing lipodystrophy in a body region in a test subject in vivo comprising measuring the temperature of the body region using infrared thermography, a raise in temperature relative to the same body region in a normal subject indicating the presence of lipodystrophy in the subject.

The present invention further provides a method of monitoring the dyslipidemic effect of treatment with a protease inhibitor in a subject comprising monitoring the body temperature of the subject during protease inhibitor treatment using infrared thermography, a raise in the temperature of the subject relative to an earlier measurement of the subject indicating a dyslipidemic effect.

The invention further provides a method of determining the temperature of internal tissues or organs of a subject comprising replacing a portion of the skin of the subject in a region of the body in proximity to the tissue or organ with an infrared-invisible polymer and measuring the temperature of the region of the tissue or organ using infrared thermography.

The invention provides a method of screening a test agent for its ability to cause a thermodynamic change in a cell-free sample, comprising:

i) measuring the temperature of said sample using infrared thermography, ii) contacting said sample with said test agent, iii) measuring the temperature of said sample resulting from step (ii) using infrared thermography, iv) comparing the temperature obtained in step (i) with the temperature obtained in step (iii), wherein a difference in temperature between that obtained in step (i) and that obtained in step (iii) indicates that said test agent causes a thermodynamic change in said sample.

The invention provides a method of screening a test agent for its ability to cause a thermodynamic change in an sample of cells in vitro, comprising:

i) measuring the temperature of said sample using infrared thermography,
ii) contacting said sample with said test agent,
iii) measuring the temperature of said sample resulting from step (ii) using infrared thermography,
iv) comparing the temperature obtained in step (i) with the temperature obtained in step (iii)

wherein a difference in temperature between that obtained in step (i) and that obtained in step (iii) indicates that said test agent causes a thermodynamic change in said sample.

The invention further provides a method of screening a test agent for its ability to cause a thermodynamic change in a sample comprising:

i) measuring the temperature of a sample or portion thereof using infrared thermography,
ii) contacting said sample, or portion thereof, with said test agent,
iii) measuring the temperature of said sample or portion thereof resulting from step (ii) using infrared thermography,
iv) repeating steps (i)–(iii) at least once,
v) comparing the temperature obtained in step (i) with the temperatures obtained in steps (iii), wherein a difference in temperature between that obtained in step (i) and that obtained in steps (iii) indicates that said test agent causes a thermodynamic change in said sample.

The invention provides a method of screening a multiplicity of test agents for their ability to cause a thermodynamic change in a sample comprising:

i) measuring the temperature of a sample or portion thereof using infrared thermography,
ii) contacting said sample, or portion thereof, with said test agent,
iii) measuring the temperature of said sample or portion thereof resulting from step (ii) using infrared thermography,
iv) repeating steps (ii)–(iii) using a multiplicity of different test agents, individually,
v) comparing the temperature obtained in step (i) with the temperatures obtained in steps (iii), wherein a difference in temperature resulting from the addition of one of said test compounds to said sample or portion thereof indicates that said one of said test agents causes a thermodynamic change in said sample.

The present invention provides a method of monitoring the physical state of a compound or composition comprising measuring the temperature of said compound or composition over time using infrared thermography, and, further, a method of determining the amount of a compound or composition present in a container comprising measuring the temperature of said compound or composition present in said container.

The present invention provides a method of determining the thermogenic effect of a test agent on a sample comprising:

i) contacting said sample, or portion thereof, with a first amount of said agent and measuring the resulting temperature using infrared thermography,
ii) repeating step (i) at least once using a second, different, amount of said agent, wherein a test agent that results in a thermogenic change in said sample at at least of said amounts is an agent that exerts a thermogenic effect on said sample.

The invention further provides a method of determining the thermogenic effect of a test agent on a sample comprising contacting said sample, or portion thereof, with said test agent and measuring the resulting temperature at a multiplicity of time points using infrared thermography, wherein a test agent that causes a thermogenic change in said sample at at least one of said time points is an agent that exerts a thermogenic effect on said sample.

The invention provides a method of screening animals for their ability to respond thermogenically to a test agent in a desired manner comprising contacting said animals with said test agent and measuring the thermogenic response of said animals using infrared thermography and selecting from said animals those that have the desired thermogenic response.

Objects and advantages of the present invention will be clear from the description that follows.

BRIEF DESCRIPTION OF THE DRAWINGS

FIGS. 13A–13D. Infrared thermographic analysis of a metered dose inhaler (MDI) device (FIG. 13A; actuations 0, 1 and 5) during and after 5 consecutive actuations (FIG. 13B). Presentation of infrared thermographic analysis of nude mice treated with the inhalant, Albuterol (FIG. 13C), and subsequent quantitation of the thoracic areas showing the kinetics of Albuterol activity (FIG. 13D).

FIGS. 15A and 15B. Infrared thermographic analysis of interscapular thermogenesis of ob/ob mice—dose-response (FIG. 15A) and kinetic data (FIG. 15B) after treatment with monoamine reuptake inhibitor GW473559A (10.0 mg/kg=-○-; 5.0 mg/kg=-□-; 1.0 mg/kg=-Δ-).

FIG. 17. Graph demonstrating the use of infrared thermography to characterize the influence of genetic background and diet on $\beta_3$-mediated thermogenesis of 19 week old rodent animal models (low fat diet=solid gray bar; high fat diet=hatched bar (animals on diet 14 weeks)) on interscapular thermogenesis.

FIGS. 18A and 18B. Infrared thermographic analysis of diet-induced thermogenesis in humans. FIG. 18A shows dosal temperature versus time; FIG. 18B shows mean differences in dosal temperature of 2 males and 1 female (mean=3–5 different days/subject) before and after lunch.

FIG. 21. Infrared thermographic analysis of VEGF peptide-induced thermogenic activity in nude mice (1=VEGF; 2=control).

FIG. 22. Infrared thermographic analysis of the effect of anti-VEGF antibody on tumor temperature.

FIG. 23A shows the thermographic image obtained at day 0, day 3 and day 5. FIG. 23B shows torso delta T(° C.) versus time post dosing (days) (back=open bar, front=solid gray bar).

FIG. 26B shows quantification of the IBAT Δ temperature for mice who have been shaved (circles) or who have had their skin removed and replaced with IR transmissive polymer (triangles) 1 h after being dosed with varying concentrations of $\beta_3$-adrenoceptor agonist.

FIG. 27B shows quantification of IR signal in the liver area 90 min after treatment with glucose at the indicated doses. FIG. 27C shows a time course of liver thermogenesis in mice after treatment with 1 g/kg glucose.

FIG. 28B shows quantification of IR signal in liver area for rats dosed with vehicle or ethanol.

FIGS. 29A and 29B. Detecting increases in liver thermogenesis utilizing an IR transparent polymer in mice treated with lipopolysaccharide (LPS) (FIG. 29A). FIG. 29B shows correlation between liver thermogenesis 90 min after treatment with LPS and aspartate aminotransferase (AST), a classical serum marker of liver damage, 10 h after treatment with LPS.

DETAILED DESCRIPTION OF THE INVENTION

The present invention is directed to a method of using infrared thermography as a tool to monitor temperature changes that occur during molecular interactions, including those that occur in isolated cells, tissues, plants, animals (e.g., man). Infrared thermography can be used to analyze the effects of various agents on heat production in a variety of cell, tissue, plant, and animal types, during enzyme catalysis, and, more generally, during ligand interaction with a binding partner. Thus, infrared thermography can be used to identify agents suitable for treating various diseases, disorders, and conditions, including those involving altered thermogenic responses.

Generally, the designation "infrared radiation" refers to electromagnetic radiation having a wavelength of between about 2.5 and about 50 microns or, expressed differently, that having a frequency of between about 200 and about 4000 inverse centimeters ($cm^{-1}$ or "wave numbers"). As understood by those familiar with infrared (IR) radiation and the IR spectrum, the frequencies of electromagnetic radiation generally characterized as infrared are emitted or absorbed by vibrating molecules, and such vibrations generally correspond to the thermal state of a material in relation to its surroundings. All solid bodies whose temperatures are above absolute zero radiate some infrared energy, and for temperatures up to about 3500° K (3227° Celsius, 5840° Fahrenheit), such thermal radiation falls predominantly within the infrared portion of the electromagnetic spectrum. There thus exists a rather straightforward relationship between the temperature of a body and the infrared radiation which it emits. In the present invention, the monitoring of radiation in the range of 3–100 microns is preferred, 3–15 microns being more preferred and 3–12 microns being most preferred (e.g., 6–12 microns).

As further understood by those familiar with electromagnetic radiation, wavelengths below 2.5 cm$^{-1}$ are considered as the "near IR" portion of the electromagnetic spectrum, and represent vibrational "overtones" and low level electronic transitions. The designation "infrared" as used herein is not intended to encompass the "near IR" portion of the electromagnetic spectrum.

Figure 1:
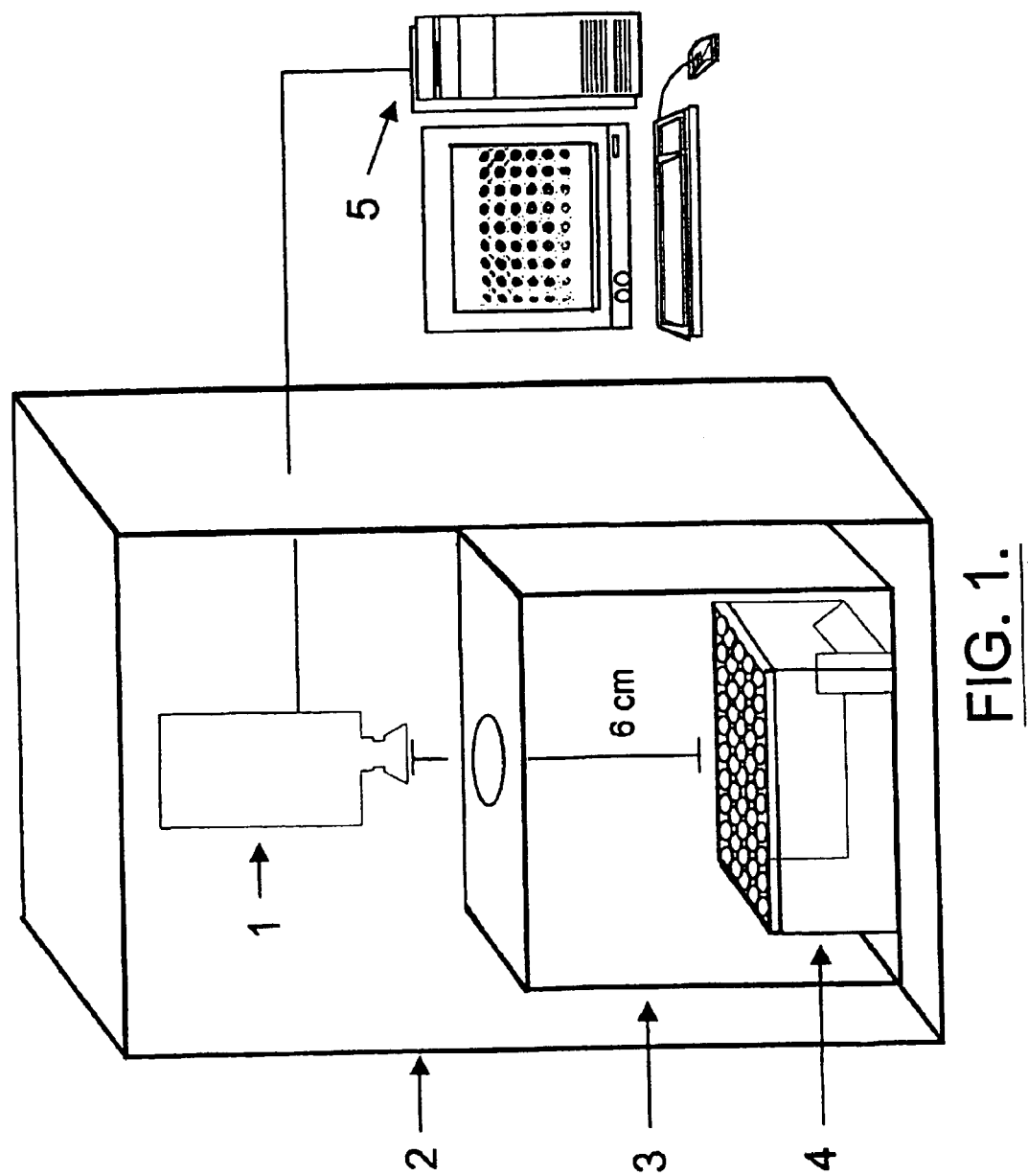
FIG. 1. Schematic of an apparatus suitable for use in imaging infrared thermogenesis in cells in culture. 1=Infrared camera; 2=cell culture incubator (37+/−0.02° C.); 3=isothermal chamber; 4=plate holder; 5=computer interface.
Figure 2:
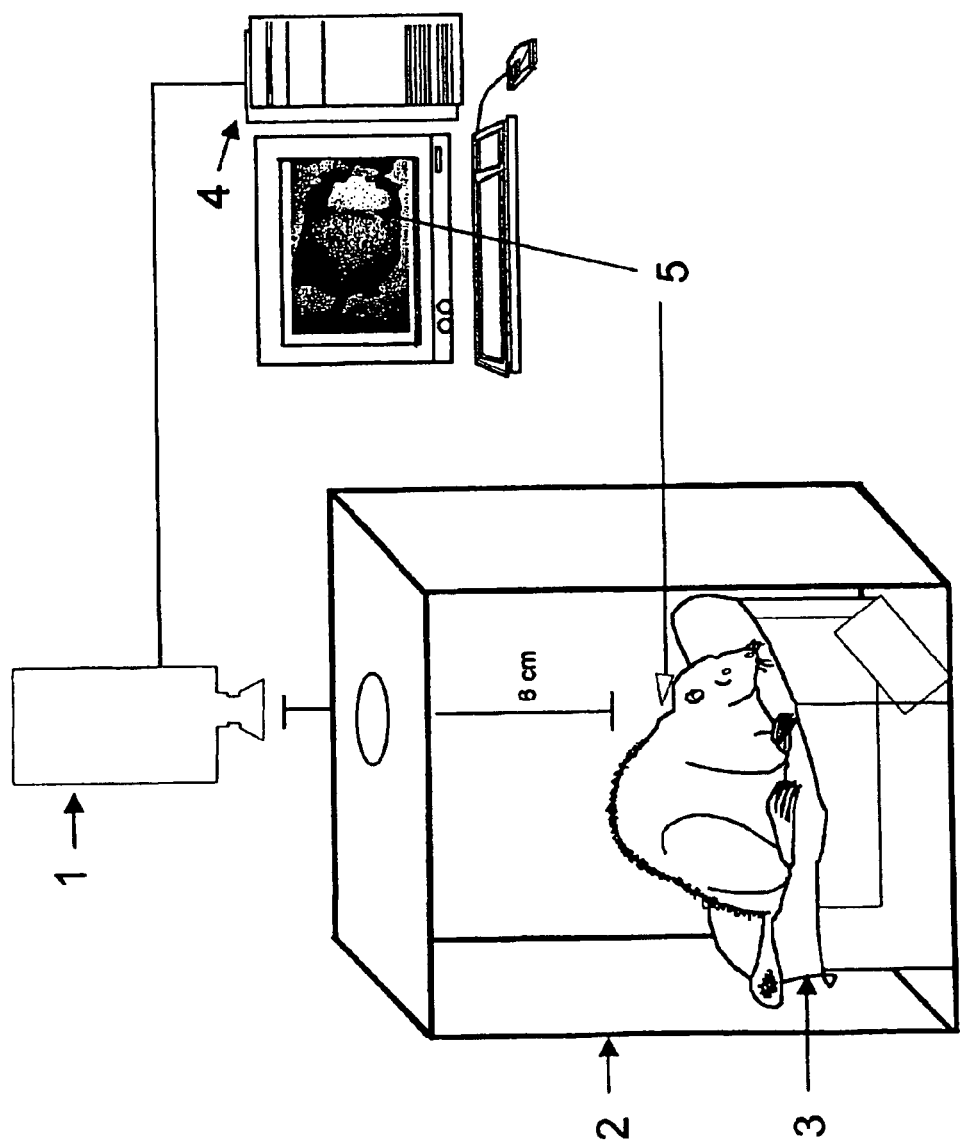
FIG. 2. Schematic of an infrared thermography device suitable for use in imaging thermogenesis in a living animal. 1=Infrared camera; 2=isothermal chamber; 3=heating pad (37° C.); 4=computer interface; 5=interscapular brown adipose tissue (IBAT).

In accordance with the invention, an infrared imaging system, advantageously, a high resolution infrared imaging system, is used to monitor real time heat output, for example, from cells or tissues in culture or from laboratory animals, with images provided by a central processing unit for data analysis (see FIGS. 1 and FIG. 2 and Examples that follow). An example of a suitable system is that produced by FLIR Infrared Systems (the AGEMA 900or QWIP SC3000). Similarly, the temperature can be measured using a non-contact infrared thermometer such as that produced by Linear Laboratories (the C-1600MP). Neither the AGEMA 900 nor the C-1600MP has heretofore typically been used in to practice a method of the present invention. However, these apparatuses can be adapted by techniques known to those skilled in the art to measure changes in temperature in the range of, for example, 5.0° C., or higher, to 0.000001° C. or lower, preferably, 1.0° C. to 0.00001° C. or 0.5° C. to 0.0001° C., more preferably, 0.3° C. to 0.0005° C. or 0.25° C. to 0.001° C., most preferably, 0.2° C. to 0.002° C. (see FIG. 1 and FIG. 2 and Examples that follow).

In one embodiment, the present invention relates to a method of monitoring the effect of an agent on thermogenesis in isolated cells, tissues, or in animals (including primates (e.g., humans)). The method comprises: i) measuring the heat produced by the cells, tissues, or a given surface area of animals before exposure to the agent using infrared thermography, ii) exposing the cells, tissues, or animal to the agent (e.g., by adding the agent to culture medium in which the cells or tissues are maintained/grown or by treating the animal with the agent using standard delivery techniques), iii) measuring the heat produced by the cells, tissues, or animals during and/or after treatment with the agent using infrared thermography, and iv) comparing the measurements obtained in steps (i) and (iii), wherein an agent that results in a lowering of the temperature of the cells, tissues or animals is an inhibitor of thermogenesis and an agent that results in an elevation of the temperature is a stimulator of thermogenesis.

Cells that can be monitored in accordance with the invention include isolated naturally occurring cells (including primary cultures and established cell lines) and engineered cells (e.g., isolated engineered cells). The cells can be in suspension or attached to a solid support either as a monolayer or in multilayers. Examples of suitable supports include plastic or glass plates, dishes or slides, membranes and filters, flasks, tubes, beads and other related receptacles. Advantageously, plastic multiwell plates are used, 96-well and 384-well microtiter plates being preferred. While preferred cell titers range between 100 to 100,000 cells/cm$^2$ for adherent cells and 100 to 1,000 cells/µl in the case of suspension cultures, potentially any cell number/concentration can be used.

Isolated naturally occurring cells that can be monitored in accordance with the present method include eucaryotic cells, preferably mammalian cells. Primary cultures and established cell lines and hybridomas (such as those available from the American Type Culture Collection) can be used. Specific examples include cells or tissues derived from fat (e.g., adipocytes and precursors thereof), muscle (e.g., myotubes, myoblasts, myocytes), liver (e.g., hepatocytes, Kupffer cells), the digestive system (e.g., intestinal epithelial, salivary glands), pancreas (e.g., αand β-cells), bone marrow (e.g., osteoblasts, osteoclasts, and precursors thereof), blood (e.g., lymphocytes, fibroblasts, reticulocytes, hematopoietic progenitors), skin (e.g., keratinocytes, melanocytes), amniotic fluid or placenta (e.g., chorionic villi), tumors (e.g., carcinomas, sarcomas, lymphomas, leukemias), brain (e.g., neurons, hypothalamus, adrenal and pituitary gland), the respiratory system (e.g., lung, trachea), connective tissue (e.g., chondrocytes), eye, kidney, heart, bladder, spleen, thymus, gonads, thyroid and other organs involved in endocrine regulation. There are no restrictions on the cell types that can be used. The present method is applicable to cells derived from plants, fungi, protozoans, and the monera kingdom (e.g., bacteria). The cells can be cultured using established culture techniques and culture conditions can be optimized to ensure viability, growth and/or differentiation, as appropriate.

Engineered cells that can be monitored in accordance with the present method include cells engineered to produce or overproduce proteins involved directly or indirectly in temperature regulation, energy balance and fuel utilization, growth and differentiation and other aspects of physiology or metabolism that alter heat generated by cells. Such cells can be engineered prokaryotic cells (kingdom monera: e.g., *E. coli*), engineered higher or lower eucaryotic cells, or cells present in or isolated from transgenic animals. Examples of higher eucaryotic cells (e.g., from the plant and animal kingdoms) include cell-lines available from the American Type Culture Collection (e.g., CV-1, COS-2, C3H10T½, HeLa, and SF9). Examples of lower eucaryotic cells include fungi (e.g., yeast) and protozoans (e.g., slime molds and ciliates). The cells or transgenic animals can be engineered to express any of a variety of proteins, including but not limited to nuclear receptors and transcription factors (e.g., retinoid receptors, PPARs, CCAAT-Enhancer-Binding Proteins (CEBPs), polymerases), cell surface receptors (e.g., transmembrane and non-transmembrane receptors, G protein-coupled receptors, kinase-coupled receptors), membrane transporters and channels (e.g., uncoupling proteins, sugar transporters, ion channels), signal transduction proteins, (e.g., phosphodiesterases, cyclases, kinases, phosphatases), and viruses (e.g., AIDS, herpes, hepatitis, adeno). Engineered cells can be produced by introducing a construct comprising a sequence encoding the protein to be expressed and an operably linked promoter into a selected host. Appropriate vectors and promoters can be selected based on the desired host and introduction of the construct into the host can be effected using any of a variety of standard transfection/transformation protocols (see Molecular Biology, A Laboratory Manual, second edition, J.

Sambrook, E. F. Fritsch and T. Maniatis, Cold Spring Harbor Press, 1989). Cells thus produced can be cultured using established culture techniques and culture conditions can be optimized to ensure expression of the introduced protein-coding sequence.

The present method can be used to identify, characterize, rank, and select agents (e.g., drugs or drug candidates) suitable for use in treating various diseases, disorders or conditions based on potency, selectivity, efficacy, pharmacokinetics and pharmacodynamics of the agent in various cell-free, cell, tissue, plant, animal, and human-based thermogenesis assays. For example, a test agent can be screened using infrared thermography for its potential as a catabolic or anabolic drug. Cultured cells (e.g., primary cells, such as adipocytes or yeast, or cell-lines, such as C3H10T½ mesenchymal stem cells, osteoblasts, or adipocytes), plants, animals, or humans (including patients in clinical studies during pharmaceutical development) can be treated with the test agent followed by infrared thermography to measure changes in heat signature. Agents that enhance thermogenesis (cellular heat production) are potentially useful as catabolic drugs and agents that suppress thermogenesis are potentially useful as anabolic drugs.

Additionally, the present invention can be used to diagnose lipodystrophy in a body region in a test subject in vivo, such method comprising measuring the temperature of the body region using infrared thermography, a raise in temperature relative to the same body region in a normal subject indicating the presence of lipodystrophy in the subject. In one particularly relevant embodiment, the body region is the face, and in another, it is the back of the neck. For this particular diagnosis, the subject can typically be HIV-positive. (see FIG. 31) Additionally, the subject will often have previously been treated with protease inhibitors.

The present invention can also be used to monitor the dyslipidemic effect of treatment with a drug therapy, such as a protease inhibitor, in a subject comprising monitoring the body temperature of the subject during drug therapy (e.g., protease inhibitor treatment or treatment with a nucleoside reverse transcriptase inhibitor) using infrared thermography, a raise in the temperature of the subject relative to an earlier measurement of the subject indicating a dyslipidemic effect. Often the relevant body region may be the face or the back of the neck.

Additionally, the present invention can be used monitor the diagnosis, progression and treatment of Psoriasis using infrared thermography. The method comprising measuring the temperature of the body region using infrared thermography, a unique heat signature relative to other body regions in a subject indicating the presence of a psoriatic lesion. (see FIG. 32)

The present invention can also be used to determine the temperature of internal tissues or organs of a subject comprising replacing a portion of the skin of the subject in a region of the body in proximity to the tissue or organ with an infrared-invisible polymer and measuring the temperature of the region of the tissue or organ using infrared thermography. (see FIGS. 26A and B). An infrared-invisible polymer can be any polymer that is an IR transmissive polymer. Examples of such an infrared-invisible polymer includes Bioclusive adhesive (Johnson&Johnson and plastic polymers such as Saran wrap). One can readily determine for any selected polymer whether It is IR transmissive by analyzing its IR transmission. This analysis can be done by measuring IR transmittance of the polymer, and comparing the quantitative measurement to that of IR transmittance in the absence of polymer, a desirable polymer having transmittance as similar as possible to that with no polymer present.

This present method can be used to measure the temperature before and after administration of a test agent to the animal, a difference in temperature resulting from the administration of a test agent indicating that the test agent had a thermodynamic effect on the tissue or organ. In addition, or alternatively, one or more dosages of the test agent can be tested by administering one or more dosages (either to different animals or to the same animal sequentially) and determining and comparing the temperature of the organ for each dose. Furthermore, effects over time can be determinined by measuring the temperature at one or more time points after administration of the test agent.

In addition to changes in metabolism, alterations in thermogenesis can reflect changes in growth and differentiation. Thus, the present method can be used to identify, characterize, rank, and select agents (e.g., drugs or drug candidates) suitable for use in treating or preventing diseases, disorder or conditions associated with changes in metabolism, toxicity, cellular growth, organ development, and/or differentiation.

Examples of pathophysiologies potentially amenable to treatment with anabolic agents identified with infrared thermography include anorexia, alopecia, auto-immunity, cachexia, cancer, catabolism associated with aging, diabetes, graft rejection, growth retardation, osteoporosis, pyrexia, bacterial and viral infections. Examples of diseases, disorders or conditions potentially amenable to treatment with catabolic agents identified with infrared thermography include diseases, disorders or conditions associated with obesity (e.g., hypertension, dyslipidemias, and cardiovascular diseases) and diseases, disorders or conditions associated with accelerated growth (e.g., cancer, gigantism, certain viral infections). The pathophysiologies amenable to treatment using agents identified with infrared thermography are not limited to those commonly associated with changes in anabolism or catabolism (e.g., metabolic diseases). The approach is also applicable to other diseases, disorders and conditions including male erectile dysfunction (MED), inflammation, hypertension, gastrointestinal diseases, behavorial disorders (CNS diseases), and diseases associated with changes in blood flow. There are no restrictions on the pathophysiologies that can be analyzed in accordance with the present invention in pharmaceutical research and development (e.g., analysis of drug potency, efficacy, toxicity, pharmacokinetics and pharmacodynamics).

In accordance with the present invention, the binding of a ligand (proteinaceous or nonproteinaceous (e.g., a nucleic acid)) to a binding partner (proteinaceous or nonproteinaceous (e.g., a nucleic acid)), where binding elicits a thermogenic response, can be monitored using infrared thermography. The ligand and/or binding partner can be in a cell or in a cell-free environment (e.g., a solution). The ligand and/or binding-partner can be a synthesized chemical entity that does not normally exist in nature, or the ligand and/or binding-partner can be a naturally occurring entity such as a naturally occurring protein, nucleic acid, polysaocharide, lipid, hormone, or other naturally occurring substance or cell. The effect of a test agent (e.g., potential ligand) on heat generated by its binding partner can be measured using infrared thermography. One suitable method comprises: i) measuring the heat produced by the binding-partner, ii) adding test agent to the binding-partner, iii) measuring heat produced after mixing the potential ligand (test agent) and binding-partner, and iv) comparing the measurements in (i) and (iii), wherein an agent that alters heat generation is a ligand for the binding partner. Additionally, test agents can be screened for their ability to after the thermogenic response resulting from the binding of the ligand to its binding-partner. Such agents can be allosteric regulators, agonists, or antagonists of the ligand and/or binding partner. Such a screen can comprise: i) measuring the heat produced upon addition of the first member of the binding pair (ligand or binding-partner) to the second member of the binding-pair using infrared thermography, and ii) measuring the heat produced upon addition of the first member of the binding pair, the second member of the binding-pair and test agent, and iii) comparing the measurement in (i) with that in (ii), wherein an agent that alters the heat generation observed upon addition of the ligand to its binding partner is a modulator of that interaction, for example, by binding to either or both members of the binding pair.

Further in accordance with the present invention, agents can be screened for their ability to modulate the rate of catalysis of a particular enzyme. The method can comprise measuring the heat produced upon addition of an enzyme to its substrate using infrared thermography and measuring the heat produced upon addition of a test agent, the enzyme, and its substrate, and comparing the results. An agent that alters heat production can be an enzyme inhibitor or activator. Controls that can be run in accordance with such a method include measuring the heat produced upon addition of the enzyme to the test compound (in the absence of substrate) and upon addition of the substrate to the test compound (in the absence of the enzyme). Such controls permit determination of the effects on heat production from the respective additions. Using such an approach, test agents can be screened for their ability to behave as substrates. Such agents can increase heat production when mixed with enzyme in the absence of any other known substrate.

In another embodiment, the present invention relates to agents identified using the above-described assays. The agents identified in accordance with the above assays can be formulated as pharmaceutical compositions. Such compositions comprise the agent and a pharmaceutically acceptable diluent or carrier. The agent can be present in dosage unit form (e.g., as a tablet or capsule) or as a solution, preferably sterile, particularly when it is to be administered by injection. The dose and dosage regimen will vary, for example, with the patient, the agent and the desired effect. Optimum doses and regimens can be determined readily by one skilled in the art.

In another embodiment, the present invention relates to a method of monitoring the effects of environmental changes (e.g., diet) and/or genetic background on thermogenesis in various organisms (animals, plants, tissues, and cells). The method can comprise: i) measuring heat produced either by an organism, using infrared thermography, under different environmental conditions (e.g., fed different diets: high or low fat, protein, or carbohydrate diets) or by organisms with different genetic backgrounds (e.g., inbred animals, populations), ii) exposing the organism(s) to various agents (e.g., placebos or thermogenic agents; including untreated controls), iii) measuring the heat produced by the organism (s) after treatment with the agent using infrared thermography, iv) comparing the measurements in steps (i) and (iii), to determine the influence of environmental changes and genetic background.

The present method can be used to identify, predict, characterize, rank, and select how different environments (e.g. diet) or genotypes can influence basal or agent-induced thermogenesis. There are no restrictions as to the population, species, strain, sex, or age of the organisms or the diet or environmental conditions that can be used. The organisms can be naturally occurring (e.g., house mouse), inbred (e.g., AKR/J mice), or engineered (e.g., transgenic mice). The method can comprise measuring the heat produced using infrared thermography upon changing the diet, circadian cycle, diurnal rhythm, altitude, barometric pressure, humidity, temperature, noise, sleep status, physical or mental stress and injury of the cell or organism. Diets can be poorly defined (e.g., cafeteria diets) or well characterized (e.g., laboratory chow). The organisms can be fed on scheduled diets or ad libitum. The agents that alter thermogenesis can be naturally occurring or synthetic, known or unknown, safe or toxic, and anabolic, catabolic, or without effect. Environmental (dietary or otherwise) changes, genotypes, or agents that enhance thermogenesis (body heat production) are potentially useful for identifying catabolic states. Environmental changes, genotypes, or agents that suppress thermogenesis (body heat production) are potentially useful for identifying anabolic states.

In another embodiment, the present invention relates to a method of monitoring drug-drug interactions in various organisms (humans, animals, plants, tissues, and cells). The method comprises: i) measuring the heat produced by the organism (cells, etc.), using infrared thermography, before exposure to the agent(s), ii) exposing the organism (cells, etc.) to a single agent and to multiple agents (e.g., by adding to culture medium or dosing by injection, gavage, topical application, etc.), iii) measuring the heat produced by the organism (cells, etc.) after treatment with a single agent and after treatment with multiple agents, using infrared thermography, iv) determining the differences in heat produced in steps (i) and (iii) and comparing the differences in heat produced after exposure to single agents with the heat produced after exposure to combined agents. A difference in the heat produced after exposure to multiple agents (as opposed to single agents) indicates that the agents interact or are eliciting a thermogenic response.

As indicated above, agents that result in a change in thermogenesis when used in combination, relative to when used singly, are proposed to be involved in pharmcodynamic drug-drug interactions. Such interactions can be potentially toxic or beneficial to the organism, tissue, or cells. As such, infrared thermography can be used to identify, predict, characterize, rank, and/or select how different agents (e.g., drugs) interact with each other. There are no restrictions to the type and number of agents, cells, tissues, and organisms that can be used. The agents can be naturally occurring, synthetic, agonists, antagonists, inhibitors, activators, safe, toxic, anabolic, catabolic, known, or unknown. The cells, tissues, and organism can be derived from plants, animals (e.g., man), fungi, protozoans, or monera. Infrared thermography can be used to measure the heat produced by cells, tissues, and/or organisms upon changing various pharmacokinetic and pharmacodynamic parameters, including altering the duration of exposure, the concentration of agent(s), pharmaceutical compositions, and number of agents used.

In a further embodiment, the present invention relates to a method of monitoring hair loss (alopecia) and regrowth. As such, infrared thermography can be used to identify, predict, characterize, rank, and/or select how different treatments or environmental stimuli alter hair growth. There is no restriction on the types of treatment or stimuli that may alter hair loss and growth. The types of treatments can include diet, exercise, pharmacological, radioactive, or surgical intervention and can be invasive or noninvasive. The stimuli for altering hair growth can be present naturally in the environment (e.g., radon gas) or a result of environmental contamination (pollution, such as pesticides). Thus, infrared thermography can be used to monitor the safety, potency, and efficacy of various treatments (natural or artificial) on hair loss and growth.

In another embodiment, the present invention relates to a method of evaluating safety profiles of pharmacologic agents. In accordance with this embodiment, various proteins (e.g., cytochrome P450s etc.), organelles (e.g., microsomes, etc.), cells, tissues, and organ types targeted by an agent can be isolated, treated with varying concentrations of the agent and heat production monitored using infrared thermography. This method can comprise: i) determining the potency and efficacy of an agent on stimulating or inhibiting heat production in the desired target (e.g., a protein, organelle, cell, tissue, or organ involved in the therapeutic effect of an agent), ii) determining the potency and efficacy of an agent on stimulating or inhibiting heat production in an undesirable target (e.g., a protein, organelle, cell, tissue, or organ involved in a toxic effect of an agent), iii) determining the selectivity of the agent by comparing the potency and efficacy in steps (i) and (ii). Pharmacological agents that show increased selectivity between the various targets (e.g., protein, organelle, cell, tissue, and/or organ), can be expected to have improved safety profiles. Consistent with this embodiment, the effects of varying the concentration of the test agent on heat generated by binding-partners and/or enzyme catalysis can be used to evaluate the selectivity and safety profile against multiple targets. Optimum selectivity between desirable and undesirable targets (e.g., cell types, binding-partners, or enzymes) can be determined readily by one skilled in the art.

In another embodiment, the present invention relates to a method of evaluating the physical state and/or amount of a compound(s). In accordance with this embodiment, the physical state of a compound can be determined using this method as it relates to a compound changing its physical properties of going from a solid (i.e. frozen liquid) to a liquid (i.e. melting), a liquid into a solid (i.e. crystallization), a liquid into a gas (i.e. evaporation, vaporization), a solid into a gas (i.e. sublimation). This embodiment can be applied but is not limited to compounds in open vessels, closed systems, pressurized vessels (i.e. inhalants). The amount of a liquid can be measured using the present invention. Consistent with this embodiment, each varying amount of the test agent generates a unique heat profile whereby the amount of agent present can be measured by its unique heat characteristics.

It will be appreciated from a reading of the foregoing that the invention has applicability in connection with virtually any animal or animal tissue. For example, the above-described methods can be applied to mammals, including primates (e.g. humans) and any of the commonly used laboratory animals (e.g., rats, mice, hamsters, guinea pigs and rabbits) as well as to birds, amphibians and reptiles and insects.

Certain aspects of the present invention are described in greater detail in the non-limiting Examples that follow.

EXAMPLES

The following experimental protocols and details are referenced, whole or in part, in the non-limiting Examples that follow.

Adipocytes

Human subcutaneous adipocytes were purchased from Zen-Bio, Inc. (Research Triangle Park, N.C.). C3H10T½ clone 8 fibroblasts were differentiated into adipocytes as previously described (Lenhard et al, Biochem. Pharmacol. 54:801–808 (1997), Paulik and Lenhard, Cell Tissue Res. 290:79–87 (1997)). After 7 days in culture, triglyceride accumulation was determined by adding lipoprotein lipase and GPO-Trinder reagent (assay kit 337-B, Sigma Diagnostics, St. Louis, Mo.) to the cells (50 $\mu l/cm^2$) and incubating the lysates at 37° C. for 2 hours. The optical density was measured using a spectrophotometer set at a wavelength of 540 nm. Lipolysis was measured as previously described (Lenhard et al, Biochem. Pharmacol. 54:801–808 (1997)).

Cloning of UCP2 and Yeast Transformation

Human skeletal muscle cDNA (#7175-1) was purchased from Clontech (Palo Alto, Calif.). UCP2 specific-sequences were PCR amplified from the sample using oligonucleotide primers that matched the 5'and 3'ends of a published sequence (GenBank U82819). Vent polymerase was used (New England Biolabs, Beverly, Mass.) in a standard reaction mixture with 2 mM $MgSO_4$ and 5% DMSO. The cycle parameters were 94° C. for 1 min., 55° C. for 1 min., and 72° C. for 1 min., repeated 29 times. The sample was passed over an S-400 spin column (Pharmacia, Piscataway, N.J.) prior to ligation in a vector for transformation of *E. coli*. The authenticity of the clone was confirmed by DNA sequence analysis. For the experiments in yeast, the UCP2 coding sequence was amplified by PCR using primers with the sequence AAAAAACCCCGGATCGAATTCATGGT-TGGGTTC AAGGCCA (SEQ ID NO:1) (sense) and CAT-TGTTCCTTATTCAGTTACTCGAGTTAG-MGGGAGCCTCTCGGGA (SEQ ID NO:2) (antisense) followed by a second PCR using primers with the sequence TTAACGTCMGGAGAAAAACCCCGGATCG (SEQ ID NO:3) (sense) and GAAAGGAAAAACGTTCATTGTTC-CTTATTCAG (SEQ ID NO:4) (antisense). The PCR product was cloned into pYX233 (R&D Systems) by homologous recombination in yeast strain W303 (a/a homozygous for ade2-1, his3-1, 15 leu2-3,112, trp1-1, ura3-1). Yeast transformants were selected on BSM-trp agar (Bio 101, Vista, Calif.). The correct UCP2 sequence was verified by sequencing plasmids back-extracted from yeast to *E coli*.

For analysis of UCP2 expression and thermogenesis, yeast containing the expression plasmids were propagated for 24 hours in BSM-trp broth, washed once and inoculated at $A_{600}$=0.001 into YP containing 2% DL-lactic acid, pH 4.5, 1% ethanol, 0.1% casamino acids and 40 mg/ml adenine. Cultures were induced 16 hours later by adding galactose to 0.4% (w/v). To assess UCP2 expression, yeast ($A_{600}$=0.1) were lysed in NuPAGE sample buffer (Novex, San Diego, Calif.) containing 5%β-mercaptoethanol and soluble proteins separated on 10% NuPAGE gels (Novex, San Diego, Calif.). A synthetic peptide using the UCP2 amino acid sequence LKRALMAAYQSREAPF (SEQ ID NO:5) was synthesized and used to generate antibodies [Zeneca, Wilmington, Del.]. Western blot analysis was performed following published methods (Paulik and Lenhard, Cell Tissue Res. 290:79–87 (1997)).

Experimental Animal Protocol

Age and weight matched male +ob/+ob mice (Jackson Labs, Bar Harbor, Me.) were housed 5 animals/cage at 72° F. and 50% relative humidity with a 12 hr light and dark cycle, and fed chow diet (NIH R&M/Auto 6F-Ovals 5K67, PMI Feeds® Inc., Richmond, Ind.). Animals starting at 41 days of age were orally gavaged once daily (8:00–9:00 AM) with 0.05M N-methylglucamine (control) and 5 mg/kg GW1929 in 0.05M N-methylglucamine. After 2 weeks of dosing, the animals were dosed (intraperitineal) with 1 mg/kg of CGP12177A, and the animals were anesthetized with isofluorane. Infrared thermographic images and temperature calculations were recorded using an Agema Thermovision 900 Infrared System. The data was calculated as the mean and standard error from experiments performed on ≧6 animals per treatment group. This research complied with the principles of laboratory animal care (NIH publication No. 86-23, revised 1985) and company policy on the care and use of animals and related codes of practice.

Male AKR/J, C57BL/6J, and SWR/J mice were purchased from 4–8 weeks of age from Jackson Laboratories (Bar Harbor, Me.). Mice were fed high and low fats diets containing high sucrose as defined by Surwit et al., (Metabolism 44(5):645–651 (1995)). After 14 weeks on these diets, the interscapular fur was shaved, the animals were dosed (intraperitineal) with 1 mg/kg of BRL37344, and the animals were anesthetized with isofluorane. Nude mice (BALB/C) were 6–8 weeks old and were dosed with inhalant two times before thermal profiling. The Lewis rat strain (200–250 g) were used for both the MED and inflammation experiments. Infrared thermographic images and temperature calculations were recorded using an Agema Thermovision 900 Infrared System.

Applications of IR Transmissive Polymer

All animals used for the IR transmissive polymer applications were anesthetized with isofluorane before surgically removing the dorsal skin to expose IBAT or opening the abdominal cavity to expose the liver. The exposed area of interest was covered with the IR transmissive polymer (Johnson & Johnson) and profiled thermally as described above. For IBAT studies, mice were dosed at either 0.0, 0.01, 0.1, 0.3, or 1 mg/kg BRL37344 in water vehicle (0.25 ml by oral gavage, n=20 per dose). The liver studies entailed using ob/ob mice fasted overnight and dosed with 0, 1, 10, 100 or 1000 mg/kg glucose in water vehicle (0.5 cc, oral gavage). Mice were anesthetized with isoflurane and their abdomens were surgically opened to expose the liver. The IR transmissive polymer was placed over the entire exposed area. IR images of the liver region were acquired and analyzed as described above. For LPS studies, ob/ob mice (n=4) were dosed at 0.0, 0.1, 0.3, or 1.0 mg/kg LPS in water vehicle (0.5 ml, i.p.) and anesthetized using isoflurane as described above 90 min after treatment. Blood was obtained by cardiac puncture for serological analysis and processed as described previously. Liver samples were fresh frozen in liquid nitrogen and stored at −80° C. for mRNA analysis. For ethanol studies, female Sprague-Dawley rats (n=6) were dosed at 0, 0.1, 0.5, 1.0 or 5.0 g/kg ethanol in saline vehicle (3.0 ml, oral gavage) twice daily for four days. On the fifth day, animals were anesthetized using isoflurane 1 h after the final treatment. Livers were imaged using the IR transmissive polymer as described above. Blood was obtained by cardiac puncture for serological analysis, and liver was fresh frozen in liquid nitrogen and stored at −80° C. for analysis of mRNA expression. For the d4T/antioxidant studies, AKR/J mice were dosed by oral gavage twice daily for two weeks with vehicle (0.5% methylcellulose with 0.1% Tween 80) or 50 mg/kg d4T in vehicle or 50mg/kg ascorbate/□-tocopherol, two antioxidants. On the fifth day, animals were treated and livers were imaged as described above.

Infrared Thermography

Heat generation was measured using a Stirling cooled Agema Thermovision 900 Infrared System AB (Marietta, Ga.) equipped with a SW Scanner and 40°×25° lens which detects a 2–5.4 micron spectral response. The scanner had an internal calibration system with an accuracy of 0.08° C. The focal distance was 6 cm. Images were captured using a recurs function set at 16 or an averaging function set at 32. The data was analyzed using OS-9 advanced systems and ERIKA 2.00 software according to the manufacturer's specifications (FLIR Infrared Systems AB, Danderyd, Sweden). Thermography of adipocytes was performed by maintaining the ambient temperature of the cultured cells at 37 ±0.02° C. using a Queue Systems Inc. (Parkersburg, W. Va.) incubator, model QWJ500SABA. Spectral analysis of yeast was performed at 30 ±0.02° C. using the same incubator system. After treating the cells with experimental agents (e.g., rotenone etc.), the temperature was equilibrated for 10 minutes in the incubator before measuring real time thermogenesis for all microtiter plate applications. Various color scales in the visible wavelength were used to depict the temperature fluctuations of the recorded images. Although temperature scales are constant, the color scale images are variable and can be adjusted with level and span controls.

Various infrared detection system parameters were optimized using both yeast and cultured adipocytes. Cell titer experiments using yeast revealed a lower detection limit at a density of $A_{600}$=0.01 and a maximal thermogenic response at a density of $A_{600}$=0.1–0.2. Whereas thermal activity of C3H10T½ cell suspensions was detected as low as $8 \times 10^3$ cells/well, the greatest signal was obtained at $1 \times 10^5$ cells/well. As expected, the maximal thermogenic response of adherent adipocytes was observed using confluent cells. A comparison of microtiter plates revealed 384-well formats were best for measuring thermogenesis of yeast suspensions while 96-well formats were most suitable for culturing adherent adipocytes. The outer wells of the culture plates were omitted from the detection system because increased thermal conductance occurred at the edge of the plates. Larger diameter wells (i.e., >1 cm) were less satisfactory because a meniscus effect was observed that resulted in uneven thermal conductance. Further, the amount of media per well was critical, since too much media decreased the signal and too little media created a meniscus resulting in increased background noise. The best results were obtained using 50 $\mu$l/well using both 96-well plates containing adherent adipocytes and 384-well plates containing yeast suspensions. Enclosure of the detection system and objects that were being profiled was essential for minimizing changes in temperature and reflectivity (ie., thermal noise) which result from air currents and light, respectively. Materials that exhibited low reflective properties (e.g., anodized aluminum), especially those materials that were in view of the infrared detector, were ideal for minimizing extraneous thermal noise during thermal profiling (e.g., chamber plates, etc.). Finally, increasing the temperature equilibration time (i.e., >10 min) improved the signal to noise ratio.

Example 1

Design of an Apparatus for Infrared Thermography

The methods of the present invention utilize an apparatus that, advantageously, consists of a high resolution infrared imaging system and a central processing unit with appropriate software for data analysis. An example of a suitable system is that produced by FLIR Infrared Systems (the AGEMA 900) or the non-contact infrared thermometer (C-1600MP) produced by Linear Laboratories. FIG. 1 shows a schematic diagram of such an apparatus for infrared thermography of cell-free systems or cell culture. The isothermal chamber, constructed from a non-reflective material that provides a heat sink to dampen out temperature fluctuations (e.g., anodized aluminum) minimizes thermal noise (e.g., reflection and air currents) from the culture plates and surrounding environment. A plate holder can be placed within the isothermal chamber to maintain thermal uniformity across the plate. Use of an incubator also prevents fluctuations in the surrounding temperatures and improves cellular responses and viability. In the schematic shown in FIG. 1, the camera monitors real time heat production from the cells in culture with images recorded by a central processing unit for data capture and software analysis tools for further data analysis. FIG. 2 shows a schematic diagram of an apparatus designed for infrared thermography of the interscapular region of mice. This apparatus shares features with the apparatus in FIG. 1, including the infrared camera, isothermal chamber and computer interface. It can also include an infrared screening platform with anesthetic manifolds for maintaining the animals under anesthesia, a tightly regulated heating block, for example, made out of anodized aluminum, and an isothermal chamber to maintain air currents at a minimum.

Figure 3A:
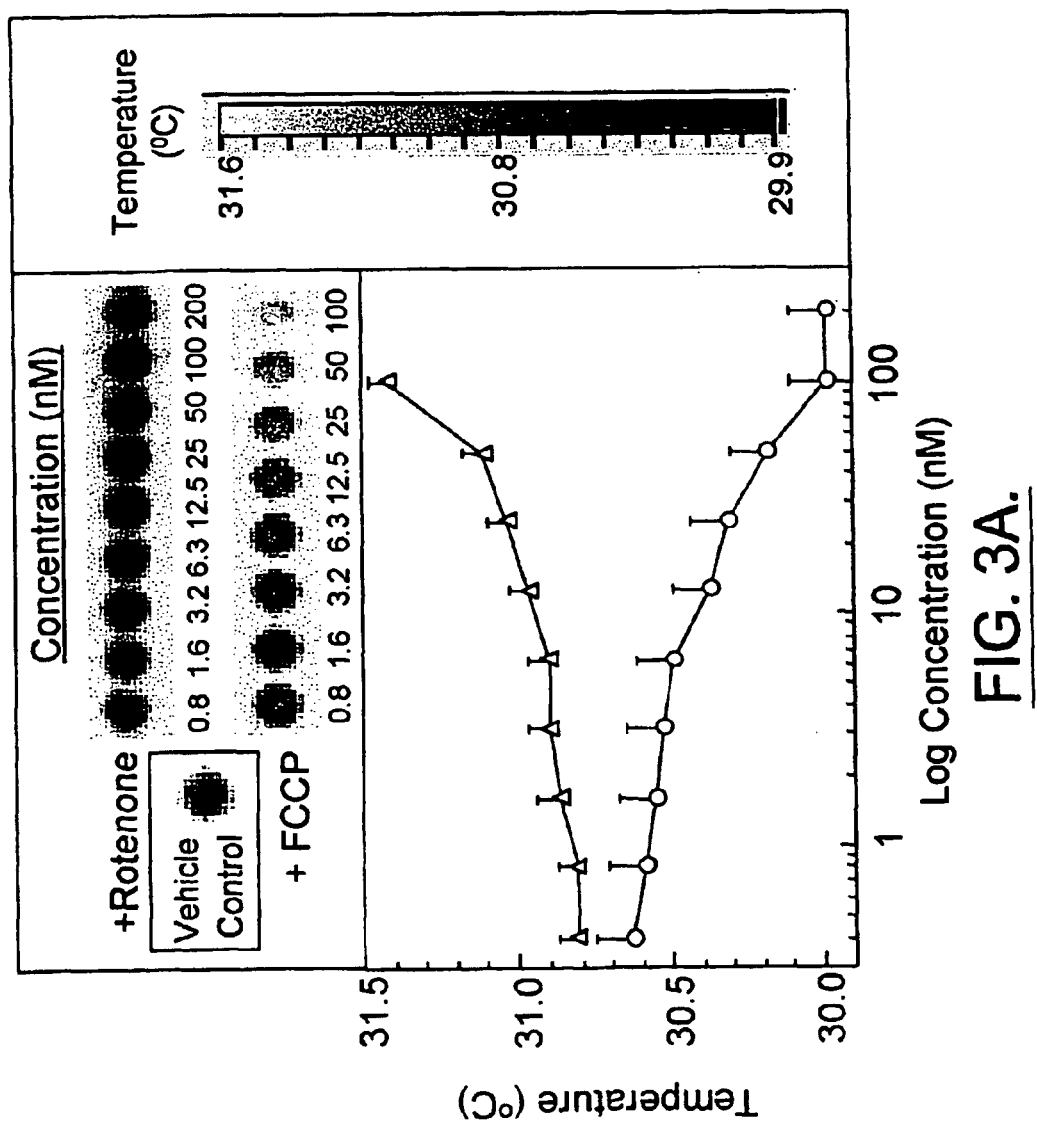
FIGS. 3A and 3B. Infrared thermography data of yeast (FIG. 3A; 384-well plate) and human adipocyte cultures (FIG. 3B; 96-well plate) treated with rotenone and FCCP presented using a gray scale index or using graphical numerical axes (Rotenone=-o-; FCCP=-Δ-).
Figure 3B:
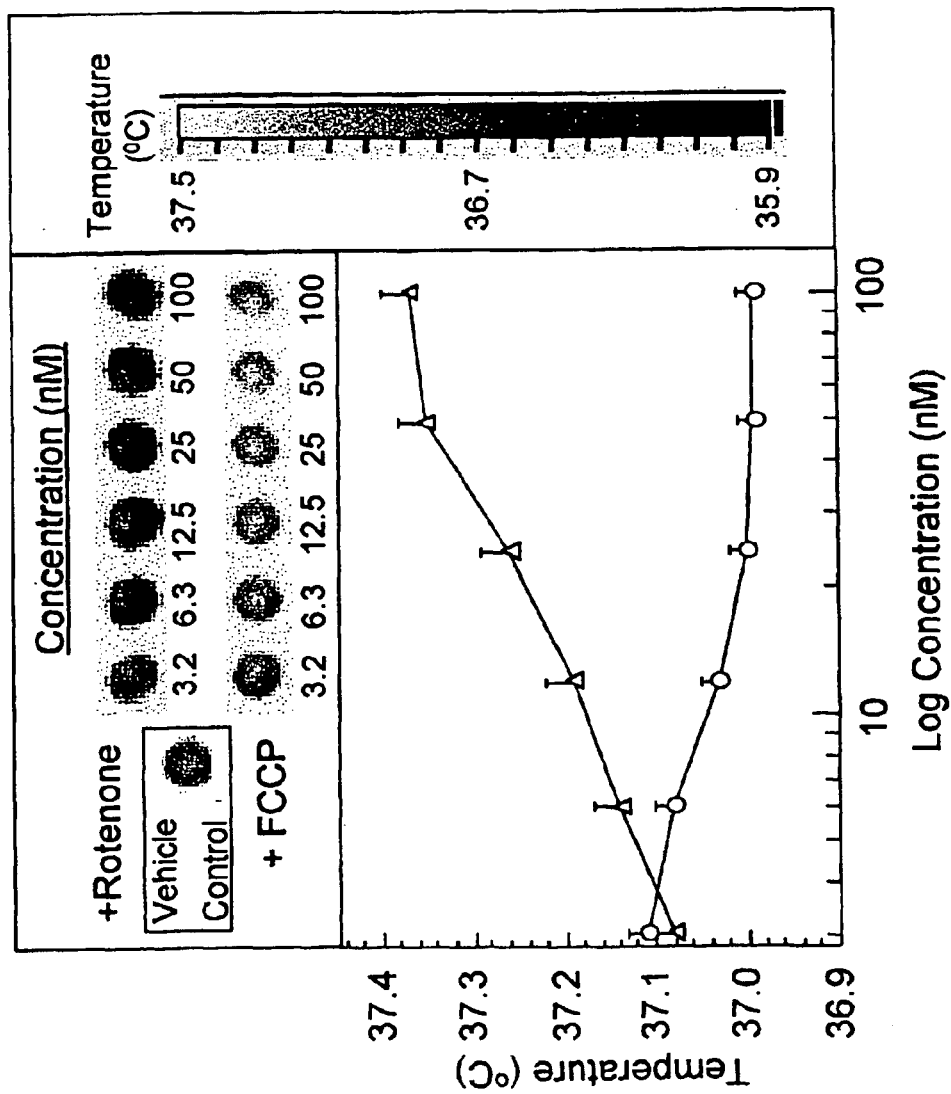

Example 2
Infrared Thermography in Cultured Cell Systems (e.g., Adipocytes and Yeast):
Effect of Small Molecules on Thermogenic Activity As part of the initial effort to validate the use of infrared thermography to monitor mitochondrial heat production, human adipocytes cultured in 96-well. microtiter plates and yeast suspended in 384-well microtiter plates were treated with rotenone or carbonyl cyanide p-(trifluoromethoxy) phenylhydrazone (FCCP). Rotenone is an inhibitor of mitochondrial electron transport (Ahmad-Junan et al, Biochem. Soc. Trans. 22:237–241 (1994)) while FCCP is an uncoupler of mitochondrial respiration (Terada, Biochem. Biophys. Acta 639:225–242 (1981)). Subsequently, the heat produced from the cells was measured using an Agema Thermovision 900 Infrared Imaging System (FIG. 1). As shown in the dose response assays in FIG. 3, rotenone treatment inhibited thermogenesis in yeast (FIG. 3A) and human adipocytes (FIG. 3B). In contrast, FCCP stimulated heat production in both cell types relative to untreated cells. Kinetic analysis revealed that changes in heat production were detectable 10 minutes after treating the cells with either agent. These results validate the use of infrared thermography for measuring the dose-dependent thermogenic effects of small molecules (e.g. FCCP, rotenone) on cells in culture or in cell-free systems.

Example 3
Effect of Protein Overexpression on Thermogenesis

In rodents, interscapular brown adipose tissue (IBAT) is an important site for adaptive thermogenesis (Himms-Hagen, Proc. Soc. Exp. Biol. Med. 208:159–169 (1995)) and is located in the interscapular region of rodents. This tissue contains abundant mitochondria which express the anion transporter, uncoupling protein (UCP1, formerly known as UCP; Ricquier et al, FASEB J. 5:2237–2242 (1991)). UCP1 uncouples oxidative phosphorylation from respiration in IBAT resulting in generation of heat instead of ATP. Although UCP1 is not abundant in Homo sapiens, UCP2 (Fleury et al, Nat. Genet. 15:269–272 (1997)) is abundantly expressed in humans. UCP2 mRNA is ubiquitously expressed and its expression is altered in obesity (Enerback et al, Nature 387:90–94 (1997)). Further, the antidiabetic thiazolidinediones (e.g., troglitazone) increase UCP2 expression, possibly by activating the nuclear. receptor PPARγ, suggesting UCP2 plays a critical role in regulating energy balance (Shimabukuro et al, Biochem. Biophys. Res. Commun. 237:359–361 (1997)).

Figure 4A:
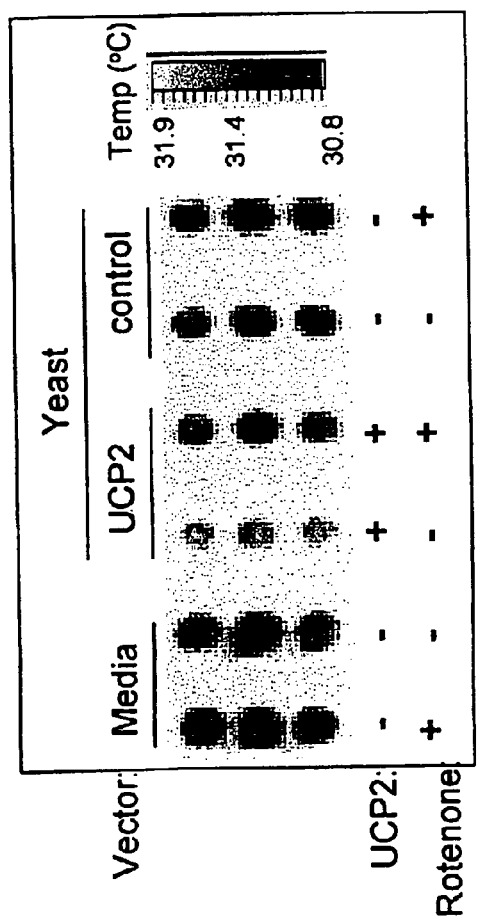
FIGS. 4A–4C. Presentation of thermographic analysis of yeast cells expressing uncoupling protein 2 (UCP2) (FIGS. 4A and 4B) and molecular analysis of UCP2 expression in the yeast cells (FIG. 4C).
Figure 4C:
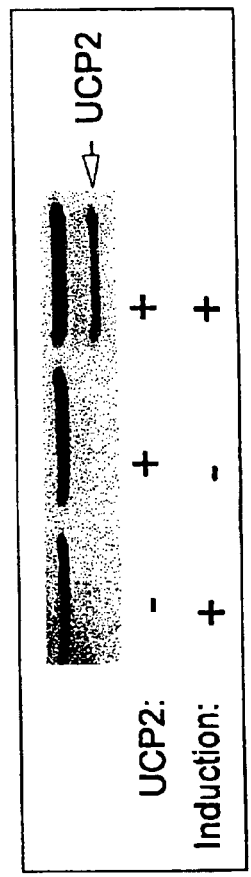
Figure 4B:
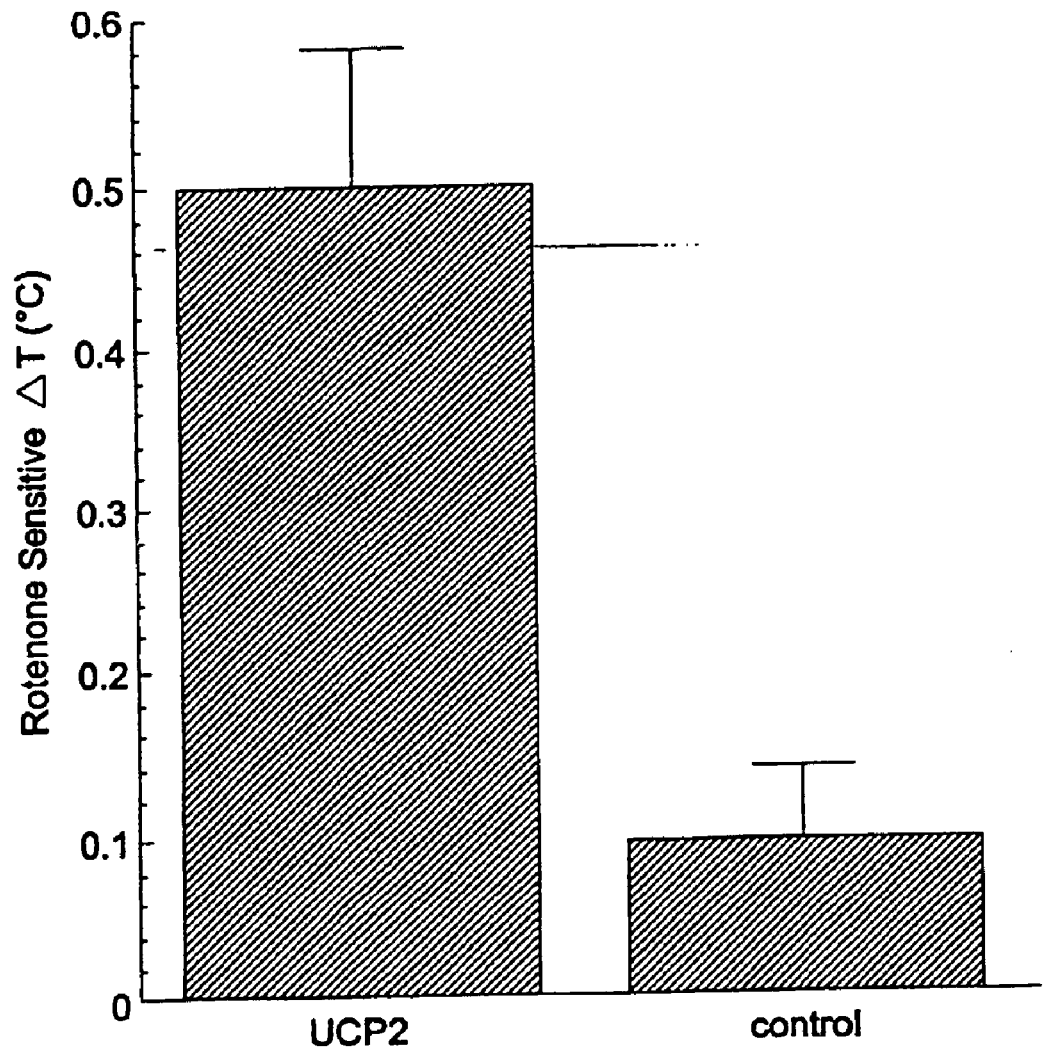

Although UCP1 regulates mitochondrial-mediated thermogenesis in rodents, there is no direct evidence that UCP2 plays a similar role. In order to evaluate UCP2's role in thermogenesis and validate the use of infrared thermography to detect physiological changes in cells engineered to express foreign proteins, the UCP2 gene was cloned from a human cDNA library and expressed in yeast using a galactose-inducible expression system. As shown in FIG. 4A, expression of UCP2 in yeast resulted in increased thermogenesis relative to cells lacking UCP2. As expected, treatment of the cells with rotenone inhibited UCP2-mediated thermogenesis (FIGS. 4A and 4B). For reference, it was confirmed that UCP2 was expressed in these cells by Western blot analysis (FIG. 4C). Peak expression and thermogenesis was observed 3–4 hours after inducing UCP2 synthesis with galactose. The results validate the use of infrared thermography as a tool to measure the effects of various molecules (e.g., reporter genes such as UCP2) on mitochondrial-mediated thermogenesis in cell models (e.g. fungi (e.g., yeast), SF9, CHO, Neurospora, etc) engineered to express foreign proteins.

Figure 5:
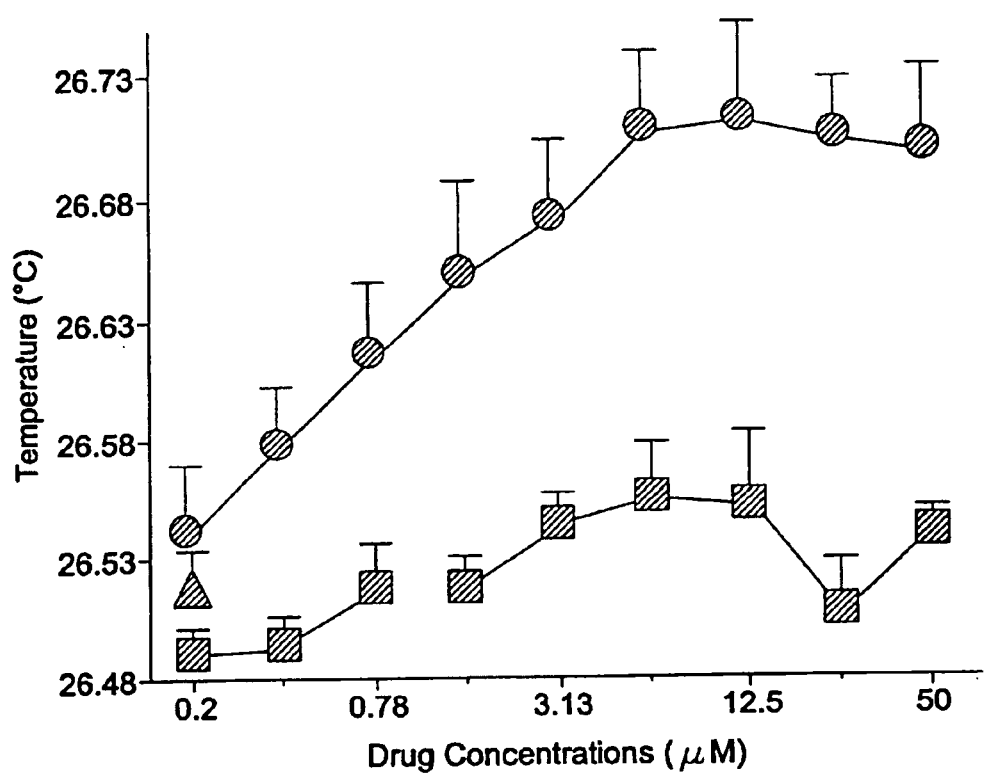
FIG. 5. Infrared thermographic analysis of thermogenesis in chinese hamster ovary cells (CHO) overexpressing the $\beta_3$-AR receptor in the presence of forskolin (-□-) or isoproterenol (-o-) (blank=-Δ-).

In order to further validate the use of infrared thermography to detect physiological changes in cells engineered to overexpress foreign proteins, the beta 3 adrenergic receptor receptor ($\beta_3$AR) was cloned from a human cDNA library and expressed in Chinese Hamster Ovary (CHO) cells. The engineered CHO cells overexpressing the $\beta_3$AR receptor were profiled thermally for their responsiveness to the well characterized $\beta_3$-AR agonist, isoproterenol (FIG. 5). As shown in FIG. 5, CHO cells were responsive in a dose-dependent manner to isoproterenol, indicating infrared thermography can be used to evaluate, identify and rank order ligands for cell surface receptors (e.g.$\beta_3$AR). These results further validate the use of infrared thermography as a non-invasive tool that can be used to rank, select and identify compounds for drug discovery using engineered cell models overexpressing foreign proteins or can be extended to antisense expression. Furthermore, infrared imaging can be used to monitor the activity of intracellular kinase activity as exemplified by the dose-dependent response of CHO cells when administered the well-characterized Protein Kinase A (PKA) agonist,forskolin (FIG. 5). Thus, infrared thermography can be used to monitor agents that affect intracellular enzymes.

Figure 6:
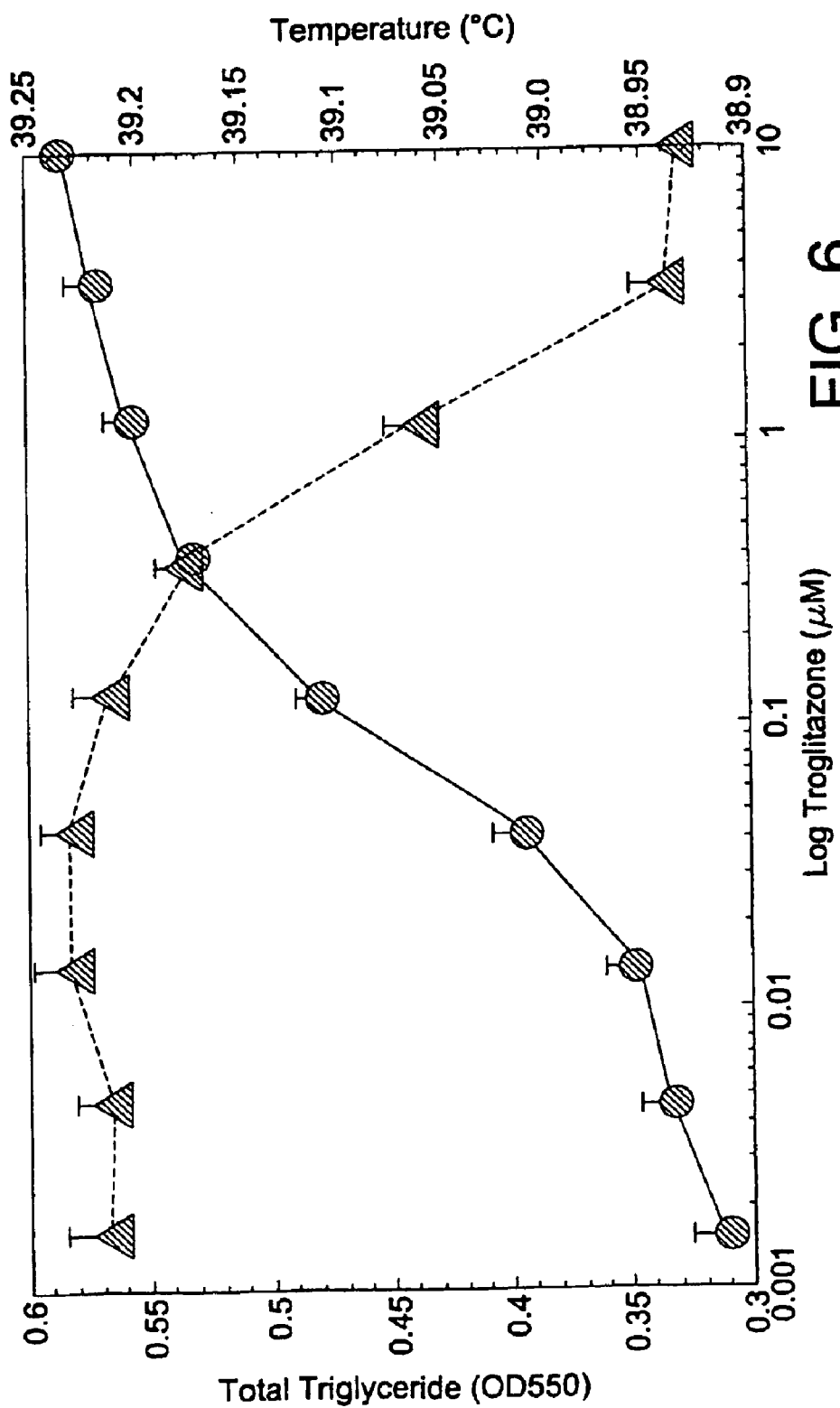
FIG. 6. Analysis of triglyceride accumulation (-o-) and heat production (-Δ-) in adipocytes.
Figure 7:
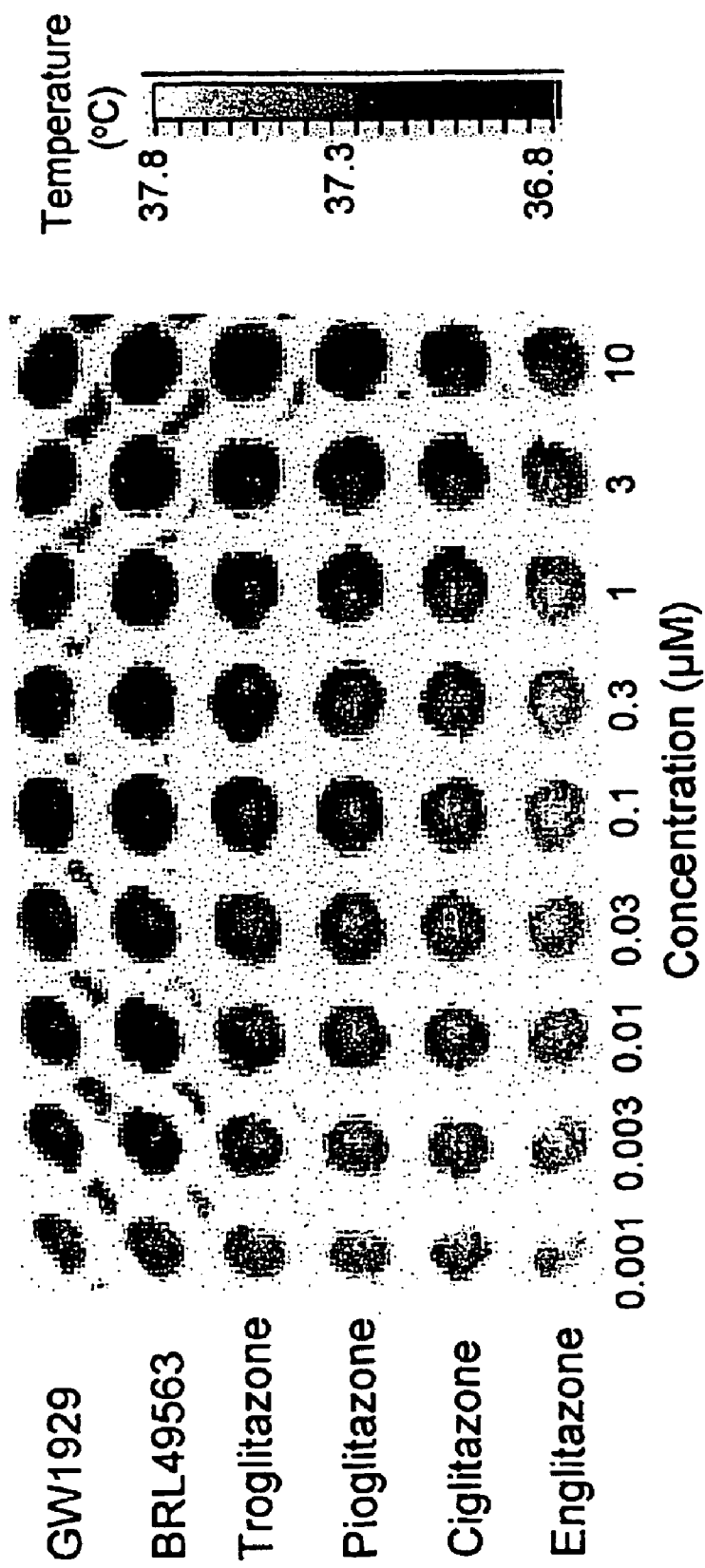
FIG. 7. Infrared thermographic image of differentiating adipocytes representing a dose response curve for several peroxisome proliferator activated receptor γ (PPARγ agonists in the presence of insulin and 9-cis retinoic acid.

Example 4
Infrared Analysis of Cells Treated with PPARγ and β-AR Agonists:
Effects on Cell Growth and Differentiation It was of interest to determine if infrared thermography could be used to analyze the pharmacological effects of drugs which alter fuel metabolism. Troglitazone is an antidiabetic agent that increases anabolism (e.g., lipogenesis and mitochondrial mass) and decreases catabolism (e.g., basal lipolysis and aerobic respiration) in C3H10T½ cells (Lenhard et al, Biochem. Pharmacol. 54:801–808 (1997)). The effects of troglitazone on these cells is a result of activation of the transcription factor PPARγ/RXR which, in turn, induces differentiation of the stem cells into adipocytes (Lenhard et al, Biochem. Pharmacol. 54:801–808 (1997), Paulik and Lenhard, Cell Tissue Res. 290:79–87 (1997), Lehmann et al, J. Biol. Chem. 270:12953–12956 (1995)). Thus, infrared thermography was used to test the affects of troglitazone and 5 structurally related agonists on heat production in C3H10T½ cells; the effect of these agents on cellular triglyceride accumulation was also measured as a marker for adipogenesis (FIGS. 6 and 7). As shown in FIG. 6, troglitazone treatment increased triglyceride accumulation in these cells, consistent with the observation that this drug promotes adipogenesis (Lenhard et al, Biochem. Pharmacol. 54:801–808 (1997), Lehmann et al, J. Biol. Chem. 270:12953–12956 (1995)). In contrast, heat production decreased in cells treated with increasing concentrations of troglitazone or the other related PPARγ agonists (FIG. 7), suggesting thermogenesis is suppressed as these cells differentiate into adipocytes. Further, the rank order potencies of the various PPARγ agonists tested in the thermogenesis and lipogenesis assays were BRL49653 ($EC_{50}(\mu M)$=0.063)⁻GW1929 ($EC_{50}(\mu M)$=0.052)>troglitazone ($EC_{50}(\mu M)$=0.316)⁻pioglitazone ($EC_{50}(\mu M)$=0.389)>ciglitazone ($EC_{50}(\mu M)$=0.123)>englitazone ($EC_{50}(\mu M)$=>10.0) (FIG. 7). Since UCP expression increases as stem cells differentiate into adipocytes (Paulik and Lenhard, Cell Tissue Res. 290:79–87 (1997), Tai et al, J. Biol. Chem. 271:29909–29914 (1996)), these observations suggest that increased UCP expression is not sufficient for stimulation of thermogenesis in adipocytes. This finding is in agreement with the suggestion that in addition to increased UCP expression other signals (e.g., $β_3$-AR stimulation) are needed to stimulate thermogenesis in adipocytes (Lenhard et al, Biochem. Pharmacol. 54:801–808 (1997), Paulik and Lenhard, Cell Tissue Res. 290:79–87 (1997)). Moreover, these results indicate infrared thermography can be used to study the pharmacological effects (i.e. efficacy, potency, kinetics, etc) of agents that affect cell growth and/or differentiation, such as troglitazone and other nuclear receptor ligands, on heat production.

Example 5
Interscapular Thermogenesis and Minimum Effective Dose Correlate in ob/ob Mice Treated with PPARγ Agonists Reagents that activate the transcription factor PPARγ/RXR have pharmacological potential as antidiabetic agents. Infrared thermography, using the method described herein can be used to monitor the effects of such drugs in animal model systems. This application has significant importance in drug development and testing.

Figure 8B:
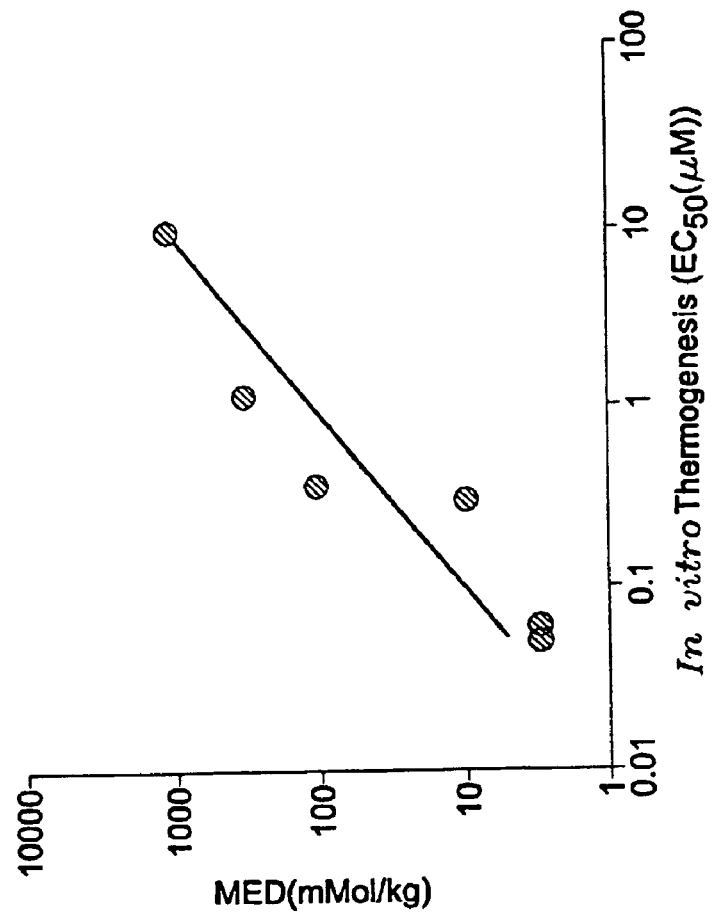
FIGS. 8A and 8B. Presentation summarizing the infrared thermographic analysis of the interscapular area of ob/ob mice treated with a PPARγ agonist, GW1929 (FIG. 8A), and the correlation between thermographic signal and the minimal effective dose (MED) of various PPARγ agonists in mice (FIG. 8B) ($r^2$=0.954).
Figure 8A:
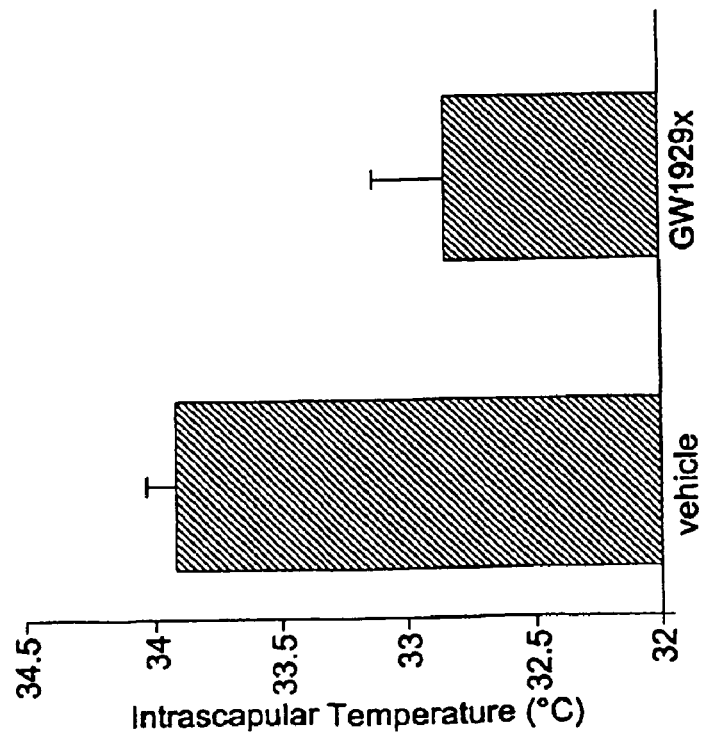

Mice with the genotype ob/ob are used as an animal model for diabetes. These animals can be used to test the activity of the antidiabetic PPARγ agonist GW1929x. FIG. 8A shows the thermogenic effect of GW1929x treatment of a group of ob/ob mice. Control mice were treated in the same manner as the experimental group but with the drug vehicle lacking the drug. As expected, treatment with the antidiabetic agent for a period of two weeks prior to assay causes a reduction in IBAT thermogenesis in the treated mice compared to the control animals (FIG. 8A). This thermogenic assay in whole animals also has quantitative value for determining drug effectiveness. The minimal effective dose (MED) for a group of PPARγ agonists in whole animals (Henke et al. J. Med Chem. 41, 5020–5036 (1998)) correlates directly with the ability of the drug to suppress thermogenesis as detected by infrared thermography in cell culture (FIGS. 8B and FIG. 7 described in Example 4). Thus, the rank order potency of the PPARγ agonists tested in cell culture plates (BRL49653⁻GW1929 >troglitazone⁻pioglitazone>ciglitazone>englitazone) corresponds to the rank order of MED in animal tests ($r^2$=0.95). These results indicate that infrared thermography can be used to study, identify, rank, and select compounds depending on their ability to alter thermogenesis or heat dissipation in animals.

Example 6
$β_3$-AR-Mediated Catabolism and Thermogenesis: Measuring Metabolically-Mediated Thermal Activity Catecholamines are postulated to regulate body temperature and composition (Blaak et al, Int. J. Obes. Relat. Metab. Disord. 17 Suppl 3:S78–S81 (1993)), possibly by regulating UCP expression (Rehnmark et al, J. Biol. Chem. 265:16464–16471 (1990)) or activity. In adipocytes, catecholamines activate β-adrenoceptors β-ARs) resulting in stimulation of the intracellular cAMP pathway (Lafontan and Berlan, J. Lipid Res. 34:1057–1091 (1993)). Stimulation of the β-AR pathway by norepinephrine injection in animals mimics cold-induced increases in UCP1 mRNA expression in IBAT (Silva, Mol. Endocrinol. 2:706–713 (1988)). Similarly, norepinephrine (Rehnmark et al, Exp. Cell Res. 182:75–83 (1989)) and $β_3$-AR-agonists (Champigny and Ricquier, J. Lipid Res. 37:1907–1914 (1996)) directly stimulate UCP1 expression in cell culture. Thus, it is often assumed that the thermogenic effects of catecholamines and $β_3$-AR-agonists are mediated by increased UCP expression. However, it has yet to be determined if $β_3$-AR-agonists induce thermogenesis in the absence of increased UCP expression.

Figure 9:
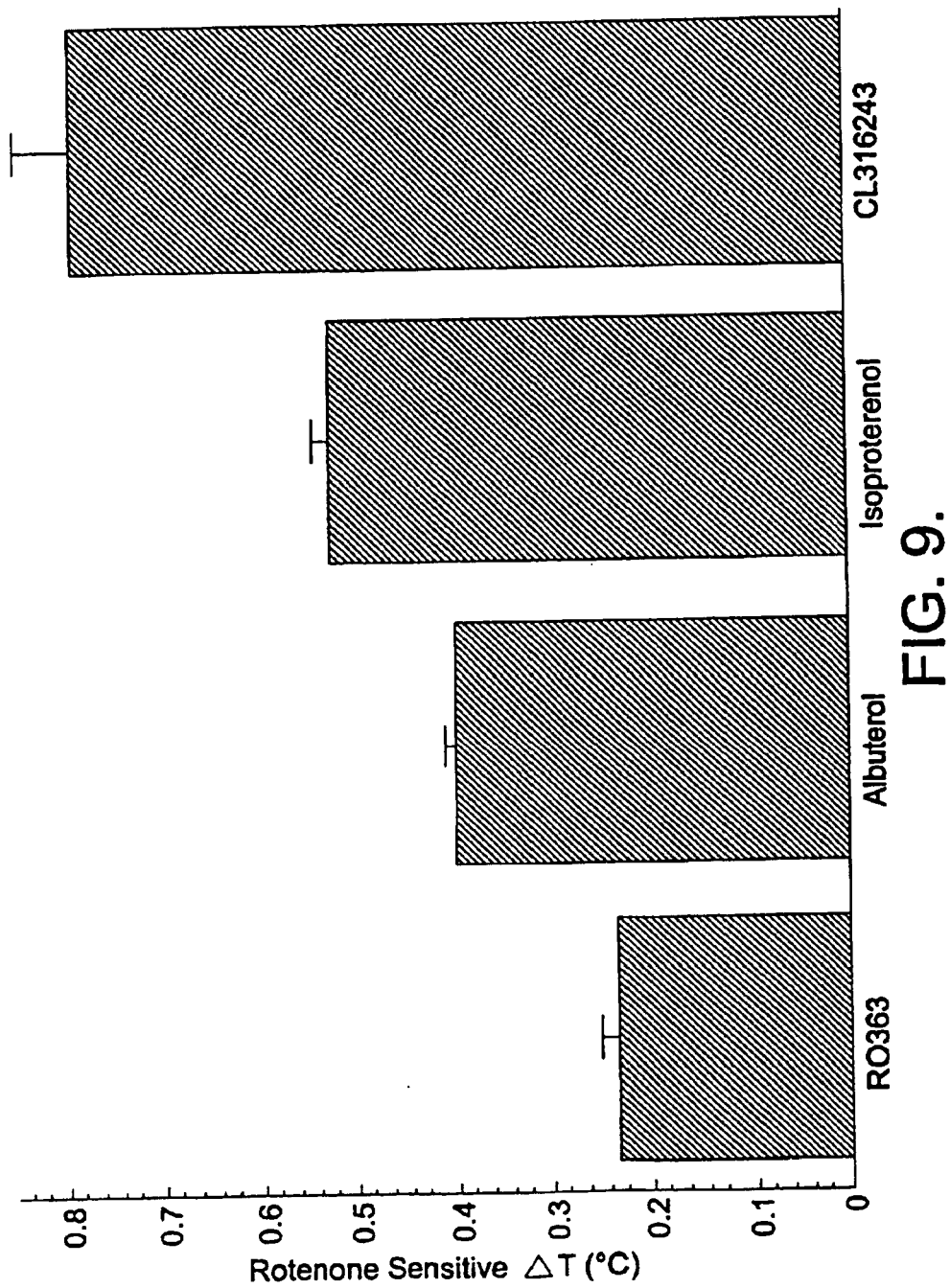
FIG. 9. Presentation showing rotenone sensitivity of β-AR agonist (50 nM)-induced thermogenesis in adipocytes.

The $β_3$-AR-agonists are candidate therapeutic agents for the treatment of diabetes and obesity. Although, the mechanism of action for these agents is thought to involve increased metabolic rate (Scarpace, Ann. N.Y. Acad. Sci. 813:111–116 (1997)), it has yet to be shown that β-AR-agonists increase heat output by adipocytes. Therefore, it was determined whether infrared imaging could be used to monitor the effects of $β_3$-AR-agonists on thermogenesis in cultured adipocytes. Thermogenesis in C3H10T½ adipocytes was stimulated by treatment with the selective $β_3$-AR-agonist, CL316243, and the non-selective $β_3$-AR-agonist, isoproterenol. The $β_1$-AR agonist, RO363, and $β_2$-AR-agonist, albuterol, were less effective than CL316243 or isoproterenol at stimulating thermogenesis in these cells, indicating that infrared thermography can be used to determine the selectivity and efficacy of multiple ligands. In contrast to β-AR-agonists, the mitochondrial electron transport inhibitor, rotenone, inhibited thermogenesis of cells treated with 50 nM of the various β-AR-agonists (FIG. 9). An inhibitor of protein synthesis, cycloheximide (100 $\mu M$), had no effect on $β_3$-AR-mediated thermogenesis in these cells. Furthermore, thermogenesis was greater after 15 min than after 18 hours treatment with CL316243 (there was a dose dependent thermogenic effect of CL316243 (dose range used was 0.8–100 nM)). Thus, $β_3$-AR-induced thermogenesis may be an acute response that does not require increased protein (e.g., UCP) synthesis. However, as suggested by others, these results do not preclude a role for $β_3$-AR in regulating UCP synthesis (Rehnmark et al, J. Biol. Chem. 265:16464–16471 (1990), Lafontan and Berlan, J. Lipid Res. 34:1057–1091 (1993), Silva, Mol. Endocrinol. 2:706–713 (1988)).

As a control, the effects of β-AR-agonists on lipolysis was also measured. Dose response analysis revealed the various β-AR-agonists had similar $EC_{50}$s in both the thermogenesis and lipolysis assays (Table 1). A correlation coefficient of 0.99 was observed when the potencies of the various β-AR-agonists were compared in both assays suggesting the same β-AR signaling pathways mediate lipolysis and thermogenesis in adipocytes. Taken together, these results validate using infrared thermography to monitor ligand-altered metabolic activities in cells. In general, this expands to measuring thermogenic activity of both catabolic and anabolic mediated-effects of potential drug candidates.

TABLE 1

| Treatment | β-AR Receptor | $EC_{50}$ (nM) Lipolysis | Thermogenesis |
|---|---|---|---|
| Oligomycin | — | — | 9.2 |
| Rotenone | — | — | 8.5 |
| RO363 | $β_1$ | 1000 | 956 |
| Albuterol | $β_2$ | 47.8 | 43.2 |
| Isoproterenol | $β_1, β_2, β_3$ | 27.1 | 28.0 |
| CL316253 | $β_3$ | 7.9 | 8.9 |

Figure 10:
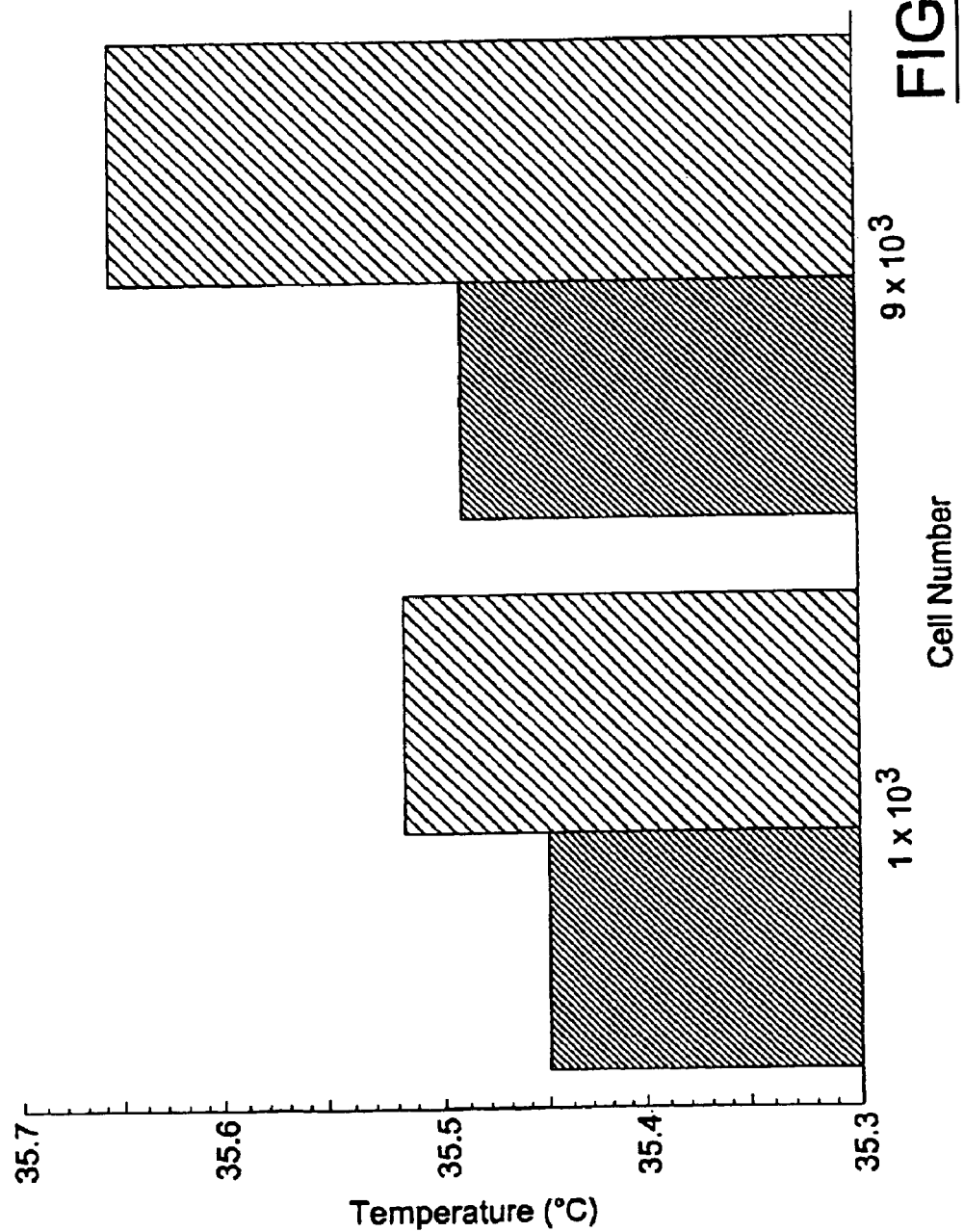
FIG. 10. Presentation of infrared thermographic analysis at 10 minutes of primary human epithelial cells (HUVEC cells) in the presence (solid gray bar) and absence (hatched bar) of vascular endothelial growth factor (VEGF).

Example 8
Effect of Peptides on Cell Surface Receptors; Measuring Enzymatic Reactions Vascular endothelial growth factor (VEGF) is a dimeric hormone that controls much of vascular development through binding and activation of its kinase domain receptor (KDR). In response to VEGF, cells rapidly activate a cascade of signal transduction molecules such as mitogen-activated protein kinases (e.g. MAPKKK, S6 kinase (p90rsk)). VEGF also causes phosphorylation and activation of transcription factor 2 in cardiac myocytes. (Ferrara, N., Davis-Smyth T, Endocr Rev 1997 Feb;18(1):4–25). The current available methods of analyzing this pathway cannot capture acute responses to VEGF. Since VEGF activation entails acute kinase/phosphatase activity, which ultimately entails bond hydrolysis and formation, heat generated from these enzymatic reactions may be measurable providing there is enough sensitivity of the instrument being used. To test this hypothesis, infrared thermography was used to measure the heat generated by human epithelial vascular cells (HUVEC) cells treated with VEGF. As shown in FIG. 10, VEGF induced thermogenesis in HUVEC cells, indicating infrared thermography may be used to monitor enzymatic reactions (e.g., kinase/phosphatase activity) in cell culture. Thus, infrared thermography can be used to evaluate the efficacy and potency of compounds on enzymatic reactions.

Example 9
Monitoring Chemical Reactions (e.g. Ligand/Binding-Partner Interactions)

Figure 11:
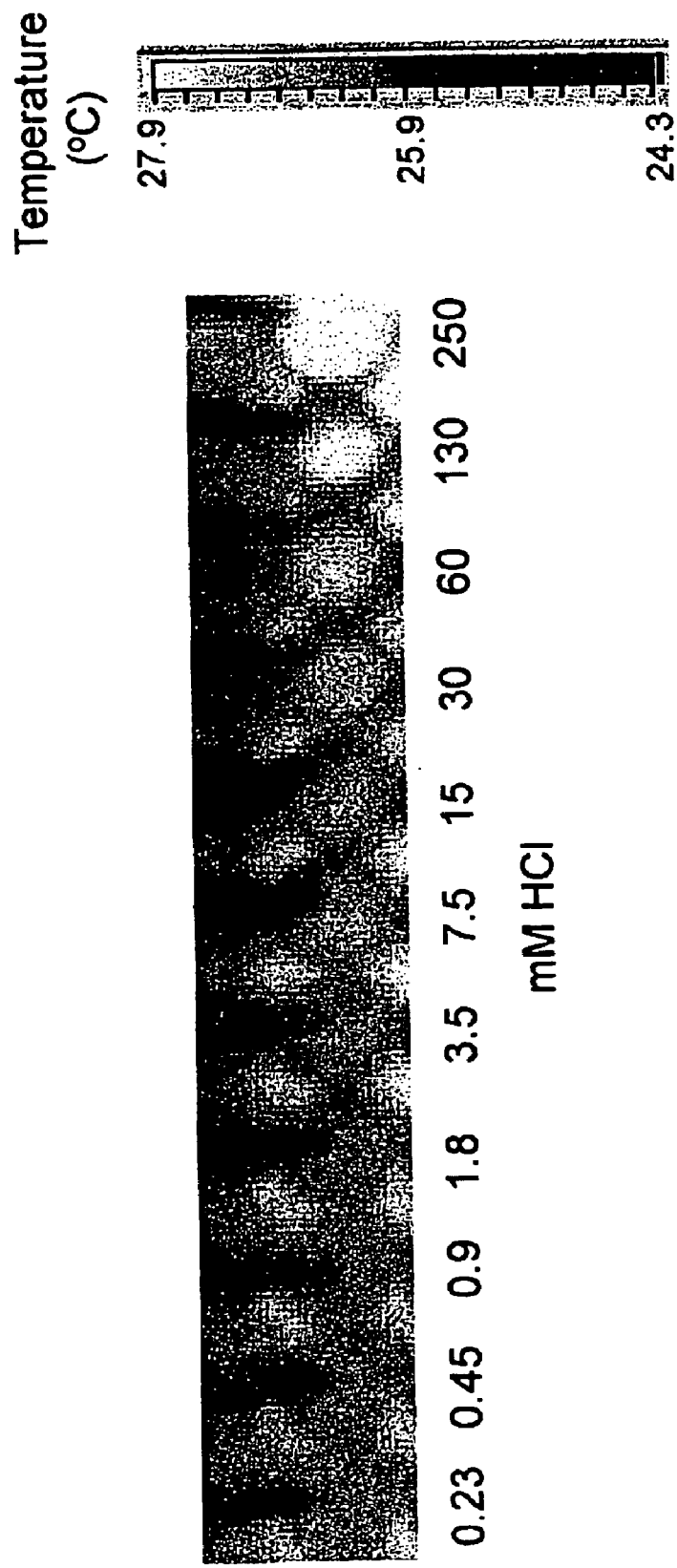
FIG. 11. Infrared thermographic analysis of a chemical reaction following NaOH addition to HCl.

The formation and hydrolysis of bonds is a process intrinsic in receptors binding to their respective ligands. This process usually entails an exothermic reaction and to date has only been measured by utilizing microcalorimetry (Koenigbauer, Pharm. Res. Jun;11(6):777–783 (1994)). These measurements are the basis for establishing binding isotherms for receptor/drug interactions. Since the mixing of acid and base elicits an exothermic response generated from the process of bond hydrolysis/formation, an acid/base titration was used to determine whether or not infrared imaging could be used to measure intrar/inter-molecular bond dynamics. As shown in FIG. 11, the mixing of 0.25 mM NaOH with varying concentrations of HCl exhibited a dose-dependent thermogenic response when measured by infrared thermography. These data validate the utility of infrared thermography in measuring molecular events such as ligand (e.g., drug) interactions with binding partners (e.g., receptors). Further examples include using infrared thermography to monitor drug-receptor, protein-protein, protein-DNA, DNA-DNA, DNA-RNA and protein-carbohydrate interactions.

Example 10
Monitoring Catalysis on Inert Solid Surfaces (e.g. Combi-Chem Beads)

Figure 12A:
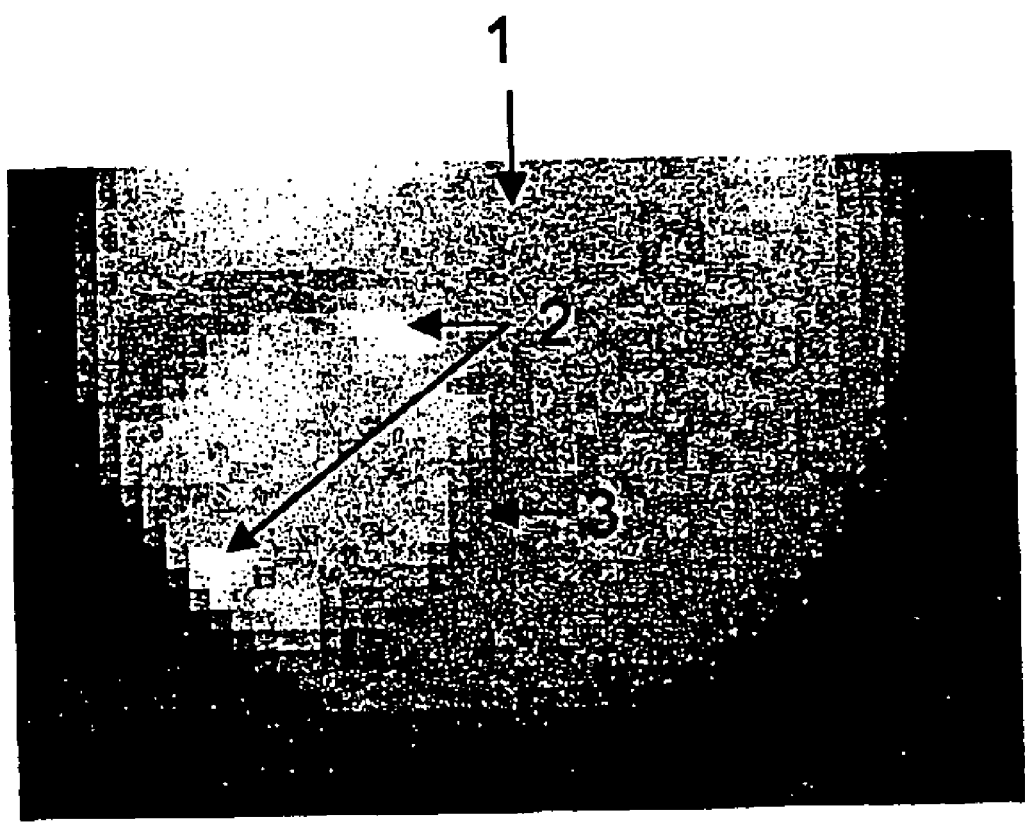
FIGS. 12A and 12B. Infrared thermographic analysis of catalytic reactions on combi-chem beads in a 25 ml beaker (FIG. 12A) (1=bulk solvent); 2=active beads; 3=O-ring) or in a 96 well microtiter plate (FIG. 12B; inactive and active beads).
Figure 12B:
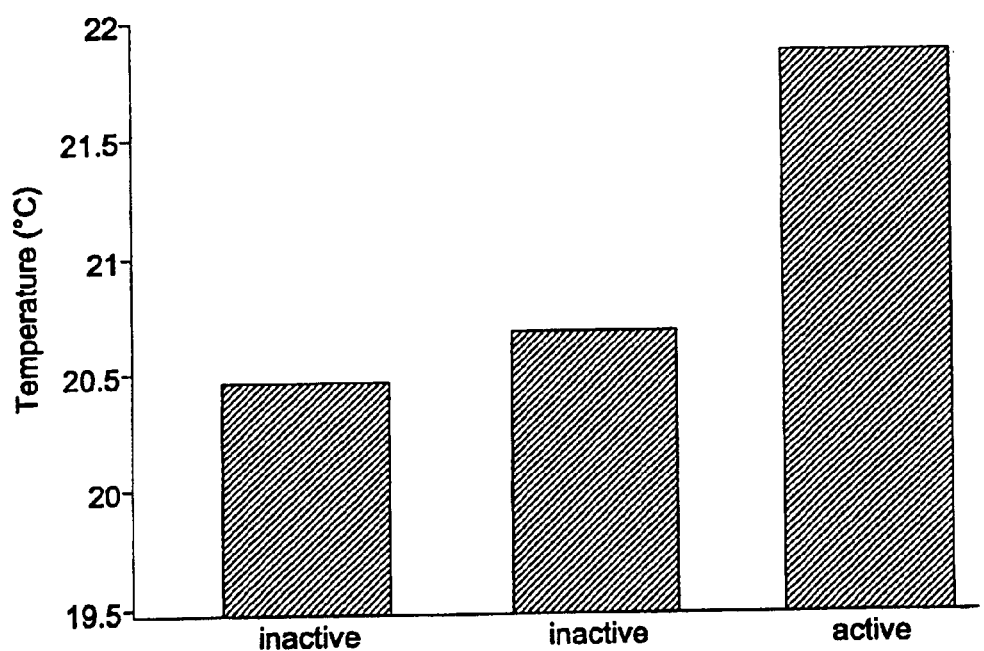

Infrared thermography as presented in this invention can also be used to measure thermogenesis in highly defined cell-free systems. Catalytic agents are often characterized while immobilized by attachment to inert solid surfaces such as combi-chem beads (Borman, Chem. Eng. News 74:37 (1996)). Thermal analysis of catalyst reactions on combi-chem beads was therefore tested using the present invention. Catalytically active combi-chem beads were analyzed while immersed in solvent in a 25 mL beaker or in a 96 well microtiter plate. FIG. 12 shows that thermogenic output localized to the area of the beaker containing the beads (FIG. 12A, arrows) (0.3° C. temperature difference) or to the wells of the microtiter plate that contain active but not inactive beads (FIG. 12B). Thus, infrared thermography can be applied to measure real-time catalyst activity in a non-invasive and non-destructive manner.

Example 11
Thermographic Analysis of Aerosol-Induced Cooling

Figure 13A:
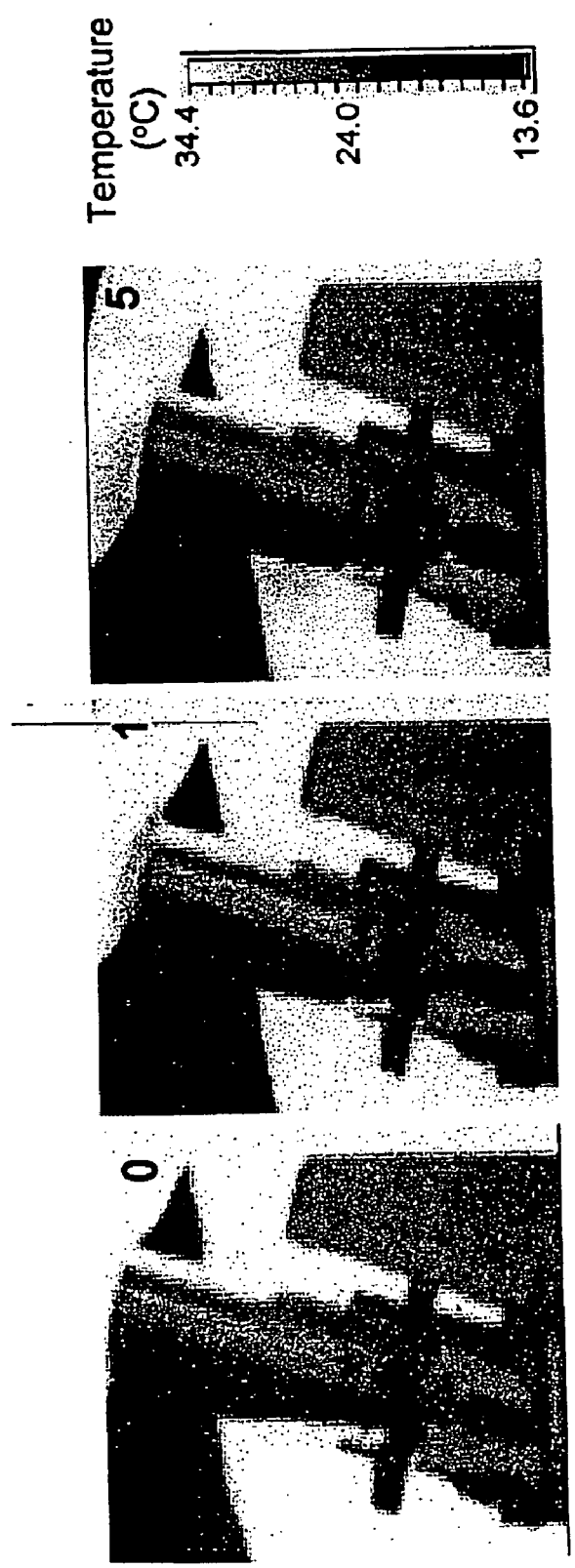

Aerosol systems, metered dose inhalers (MDI), used in drug delivery are associated with decreased temperature in the apparatus chamber during delivery. This effect has significant implications for the efficiency of drug delivery. A decrease in chamber temperature often causes drug crystallization within the MDI chamber and stem, ultimately, resulting in inefficient delivery of the drug. Infrared thermal imaging can be used to monitor the temperature loss during drug delivery and to test modified devices that alleviate or ameliorate the problem. Thus, infrared thermography was tested as a measure of actuation-induced chamber cooling of a MDI. FIG. 13A shows a thermal profile in real time of an MDI after 0, 1 or 5 consecutive actuations. The thermal image was analyzed for temperature fluctuation in the three following areas: area 1—the surface of valve stem/expansion chamber; area 2—the surface of the middle of the canister; area 3—the canister head inside which sits the metering chamber. The graphical representation of area temperature over time shown in FIG. 13B indicates that an actuation-dependent temperature decrease occurs specifically in the valve stem/expansion chamber. Iterative drops in temperature occur with each actuation.

Figure 13C:
Figure 13D:
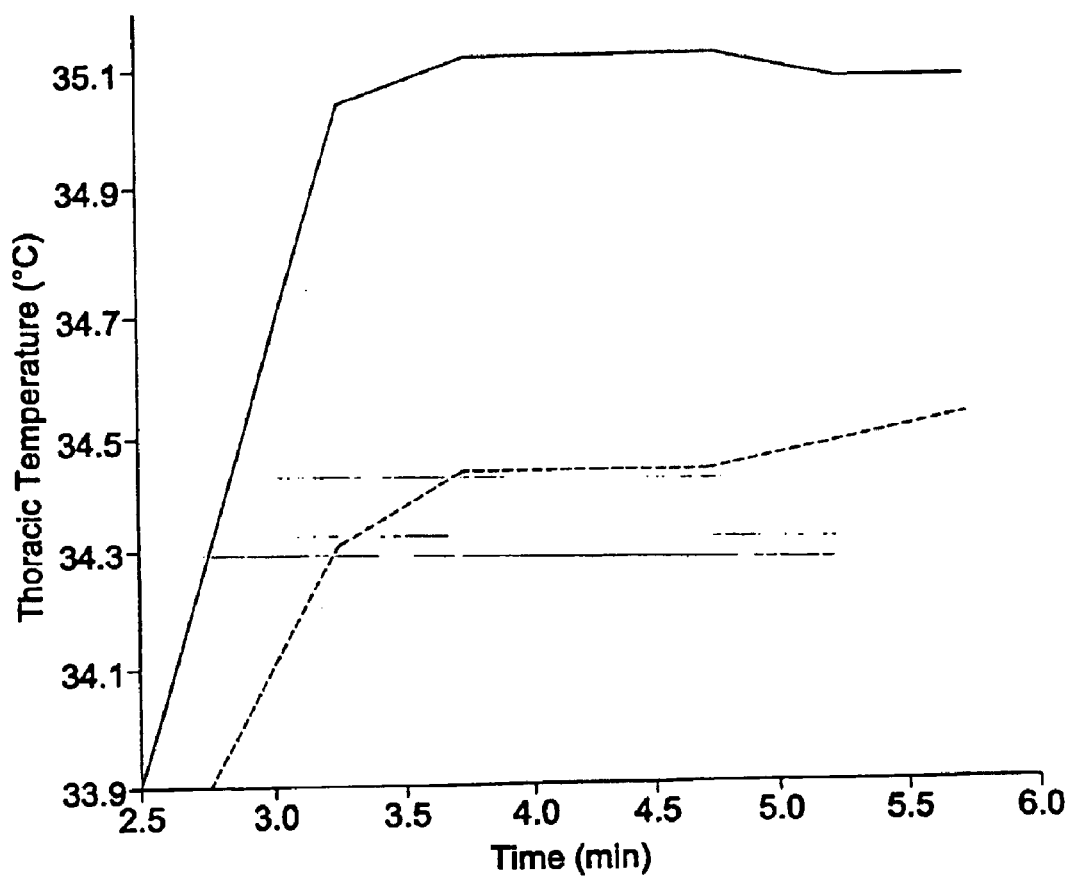

Furthermore, the bioavailability and bioactivity of inhalants in animals and man is often difficult to measure and quantitate. Assays available for measuring bioavailabilty of inhalants involve measuring the uptake of radiolabeled inhalant in selected tissues (eg. lung). Infrared thermography provides a non-invasive method for measuring the bioavailibilty/bioactivity of inhalant compounds. Thus, infrared thermography was used to measure the thermal activity induced by an inhalant in the thoracic area of nude mice. FIG. 13C shows a thermal profile of nude mice that were treated with inhalants containing either vehicle or albuterol. The graphical representation of the torso area temperature indicates that the torso temperature increases after 2.5 minutes of dosing with inhalant (FIG. 13D). Taken together, these results indicate that infrared thermography can be used to non-invasively measure the delivery of inhalants in the devices as well as the bioavailability/bioactivity of inhalants in animal models.

Figure 14A:
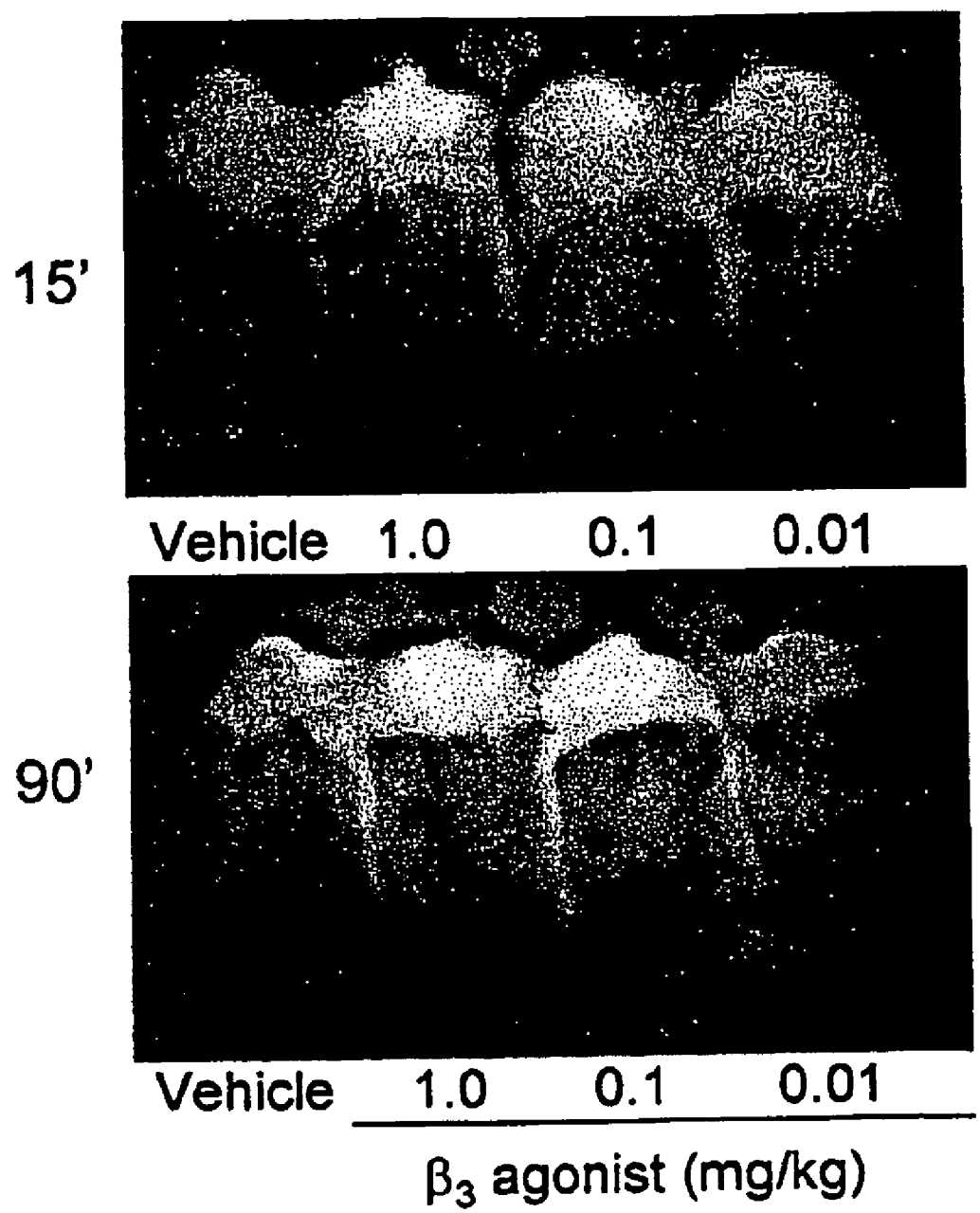
FIGS. 14A and 14B. Presentation of infrared thermography analysis of interscapular thermogenesis of mice showing a dose-response curve and kinetic data after treatment with a $\beta_3$-AR agonist (1.0 mg/kg=-○-; 0.1 mg/kg -□-; 0.01 mg/kg=-Δ-).
Figure 14B:
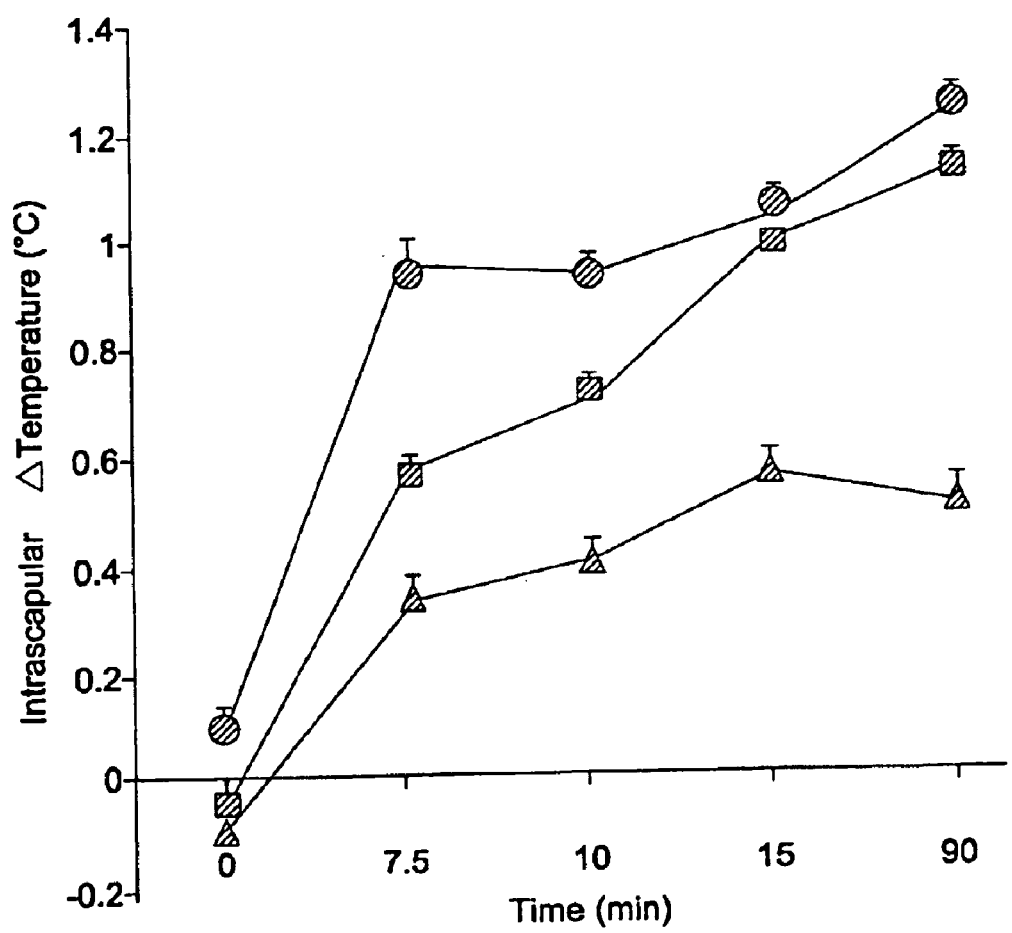

Example 12
Infrared Thermography Can Be Used to Measure IBAT Thermogenesis in Mice Treated with $\beta_3$-AR-Agonists The ability of $\beta_3$AR-agonists to stimulate thermogenesis in cultured adipocytes and CHO cells was shown and discussed in Examples 3 and 6 and FIGS. 5, 8 and 9 above. Since there are potential clinical applications for the use of catabolic agents (e.g., $\beta_3$AR-agonists) in the treatment of diabetes and obesity, it is important to show that infrared thermography can measure $\beta_3$AR-agonist-induced effects in whole animals. FIGS. 14A and 14B show that infrared thermography can be used to measure a dose-dependent and time-dependent increase in the interscapular brown adipose tissue region (IBAT) thermogenesis in animals challenged with a $\beta_3$AR-agonist. The hypothesis that $\beta_3$AR agonist-induced thermogenesis reflects increased catabolic activity was tested by direct measurement of serum glycerol in treated animals. $\beta_3$AR agonist-induced thermogenesis correlates with increased serum glycerol in treated mice (correlation coefficient=0.92). Thus, this validates the use of infrared thermography to monitor the in vivo effects of catabolic agents in animals.

Figure 15B:
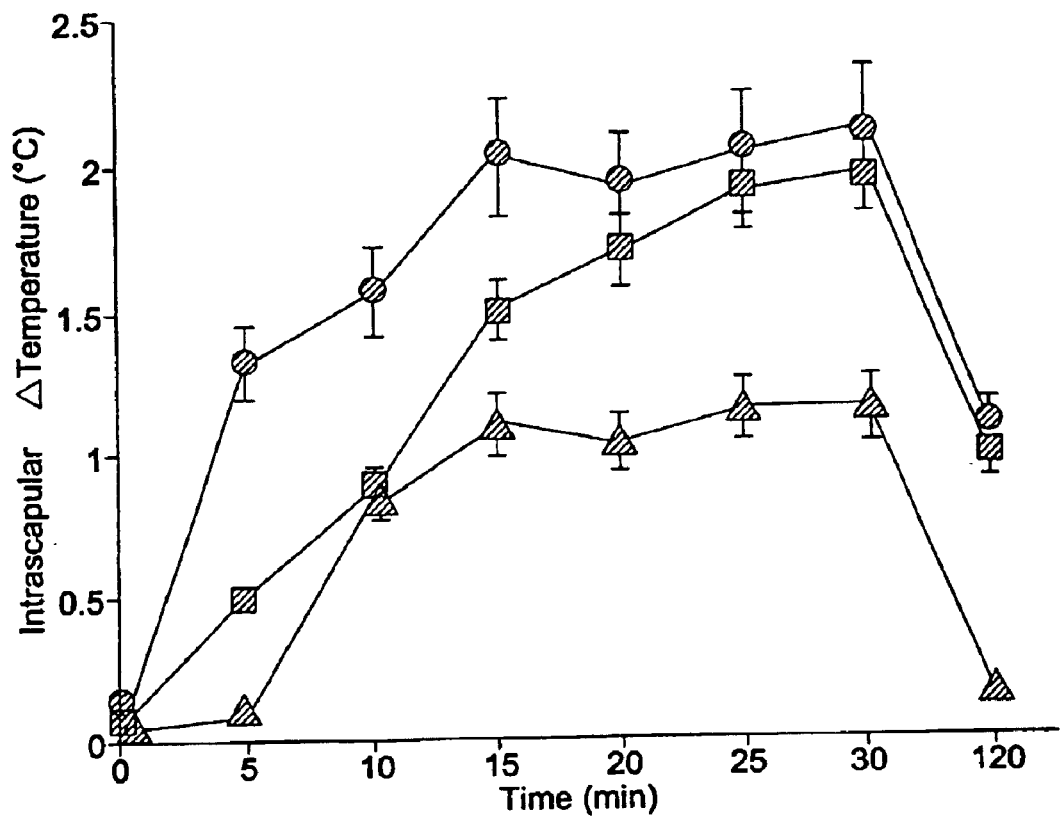

Example 13
Thermographic Analysis of ob/ob Mice Treated with a Monoamine Reuptake Inhibitor Over Various Time Points and Drug Concentrations Monoamine reuptake inhibitors are a class of drugs that stimulate catabolic activity (Stock, Int. J. Obesity 21:525–29 (1997)). The effect of a representative monoamine reuptake inhibitor, GW473559A was monitored by infrared thermography of treated mice. FIG. 15 shows that infrared thermography measures a dose-dependent (FIG. 15A) and a time-dependent (FIG. 15B) increase in IBAT thermogenesis in ob/ob mice treated with GW473559A. Thus, infrared thermography provides a non-invasive, sensitive, and robust surrogate assay for the bioavailability and activity of compounds.

Figure 16:
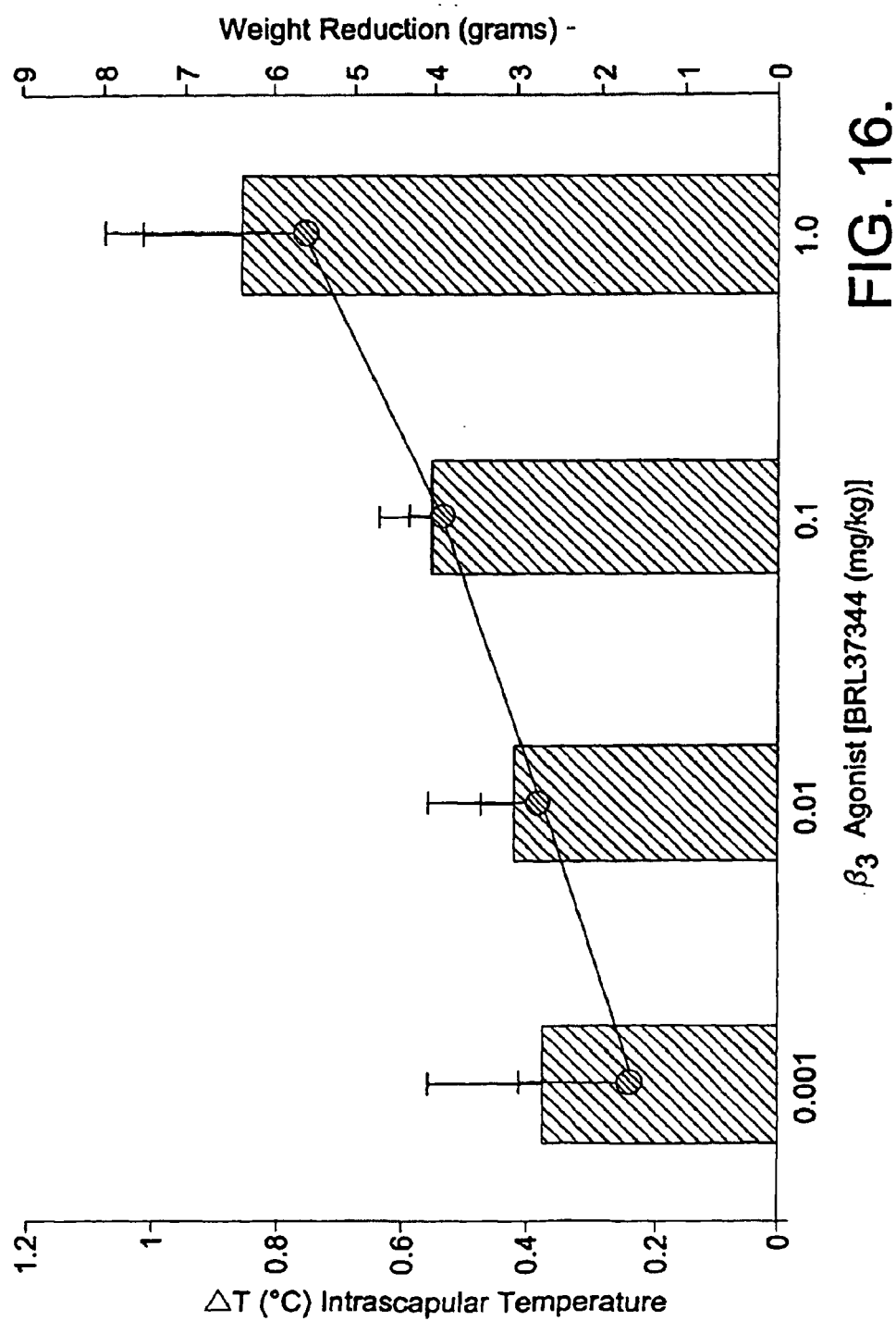
FIG. 16. Graph correlating interscapular thermogenesis and weight reduction in mice treated with a $\beta_3$-AR agonist (IBAT thermogenesis=bar, 2-week weight reduction=-○-) (r=0.97).

Example 14
Thermographic Analysis as a Surrogate Assay to Predict Body Weight Changes Treatment with $\beta_3$AR-agonists to control diabetes or obesity can require therapy that spans extended time periods (weeks or months). One desired outcome of $\beta_3$AR-agonist treatment can be weight loss. Data shown in FIG. 16 demonstrate that infrared thermography can be used to predict weight loss resulting from drug treatment. AKR mice were placed on a high fat diet and treated with either placebo or $\beta_3$AR agonist (twice daily) for 2 weeks. During the study both thermogenic activity as measured by infrared thermography of the interscapular area and weight loss were measured. Weight loss after two weeks correlated with the interscapular area thermogenesis (r=0.97). Thus, infrared thermography can provide a non-invasive surrogate assay for both preclinical and clinical use for compound selection, and evaluation of efficacy and potency.

Drug treatments for weight reduction in diabetic and obese patients is often a long-term therapy. Infrared thermography detects the drug induced metabolic change whenever the drug is administered. Changes in IBAT thermogenesis recorded by infrared thermography after animals were treated with monoamine reuptake inhibitors provide a valid correlation for % reduction in weight gain for both acute (treatment=2 hrs; r=0.92) and chronic (treatment =14 days, 2 hrs post-dosing; r=0.94) treatment protocols. Infrared thermography provides a non-invasive surrogate assay for predicting weight loss, thus, precluding labor intensive, long-term and expensive weight loss studies.

Example 15
Genetic Influence on Diet-Induced Thermogenesis

Considerable evidence indicates that metabolism is influenced by genetic and environmental factors. One environmental component that alters the metabolic rate in individuals with a genetic predisposition towards diabetes, dyslipidemia, or obesity is diet. It was unknown if thermography could be used to measure the effects of diet on drug-induced changes in heat production in animals with different genotypes. Thus, three different inbred strains of mice, AKR/J, C57BL/6J, and SWR/J, were maintained on high and low fat diets for 14 weeks before treating with the $\beta_3$-adrenoceptor agonist, BRL37344. The heat produced in the interscapular region was measured before and after 60 min treatment using infrared thermography. As shown in FIG. 17, the obesity prone mice, AKR/J, had a greater thermogenic response to BRL37344 when fed the higher fat diet. In contrast, the obesity resistant mice, SWR/J, had a greater thermogenic response when fed the lower fat diet. There was little difference in the thermogenic response of C57BL/6J mice on a high or low fat diet. These results validate using infrared thermography to measure how genotype and environmental changes (e.g., diet) effect drug-induced changes in heat output. Thus, this technique may be used to select, rank order for the efficacy and potency of compounds with the desired properties for a given environment or genetic background. Similarly, this technique can be used to identify, rank, and select animals and environmental factors with the desired properties for a given drug candidate.

Example 16
Infrared Thermography of Diet-Induced Thermogenesis in Humans

Caloric uptake has a dramatic and acute influence on metabolic activity in humans. Thus, the thermogenic output of the dorsal area of a human subject will vary as a function of the time of day and the subject's pattern of food intake. This is demonstrated in a profile of a patient whose dorsal temperature is monitored by infrared thermography at time points before and after a meal. FIG. 18A shows quantitative analysis of the thermographic profile for time points before and after lunch. FIG. 18B shows a graph summarizing similar measurements made in 2 male subjects and 1 female subject before and after lunch (Torso Delta T) on three separate occasions. This data set is consistent and reproducible, and indicates that infrared thermography of humans is possible for monitoring thermogenesis. This method may be useful to monitor many situations applicable to human patients, such as diet modulation, drug treatment, drug/drug and drug/environment interactions. Based on the results using infrared thermography, changes in diet and environment and drug use can be prescribed.

Example 17
Infrared Thermography of Drug-Induced Thermogenesis in Humans

The sympathomimetic agent ephedrine has been reported to have potent thermogenic and anti-obesity properties in rodents (Astrup et al, Am. J. Clin. Nutr. 42:183–94 (1985)). Weight loss and body composition measurements are markers primarily used to determine the efficacy of pharmological treatments for obesity. However, studies utilizing these markers tend to be time consuming, large and costly. In order to circumvent these problems, surrogate markers have been developed. Indirect calorimetry is used to determine resting metabolic rate but due to its complexity, it is not widely used. Biochemical markers such as glucose, glycerol, nonesterified fatty acids, triglycerides have been used but are invasive. However, thermogenic imaging has never been used to measure the properties of ephedrine in humans.

Figure 19:
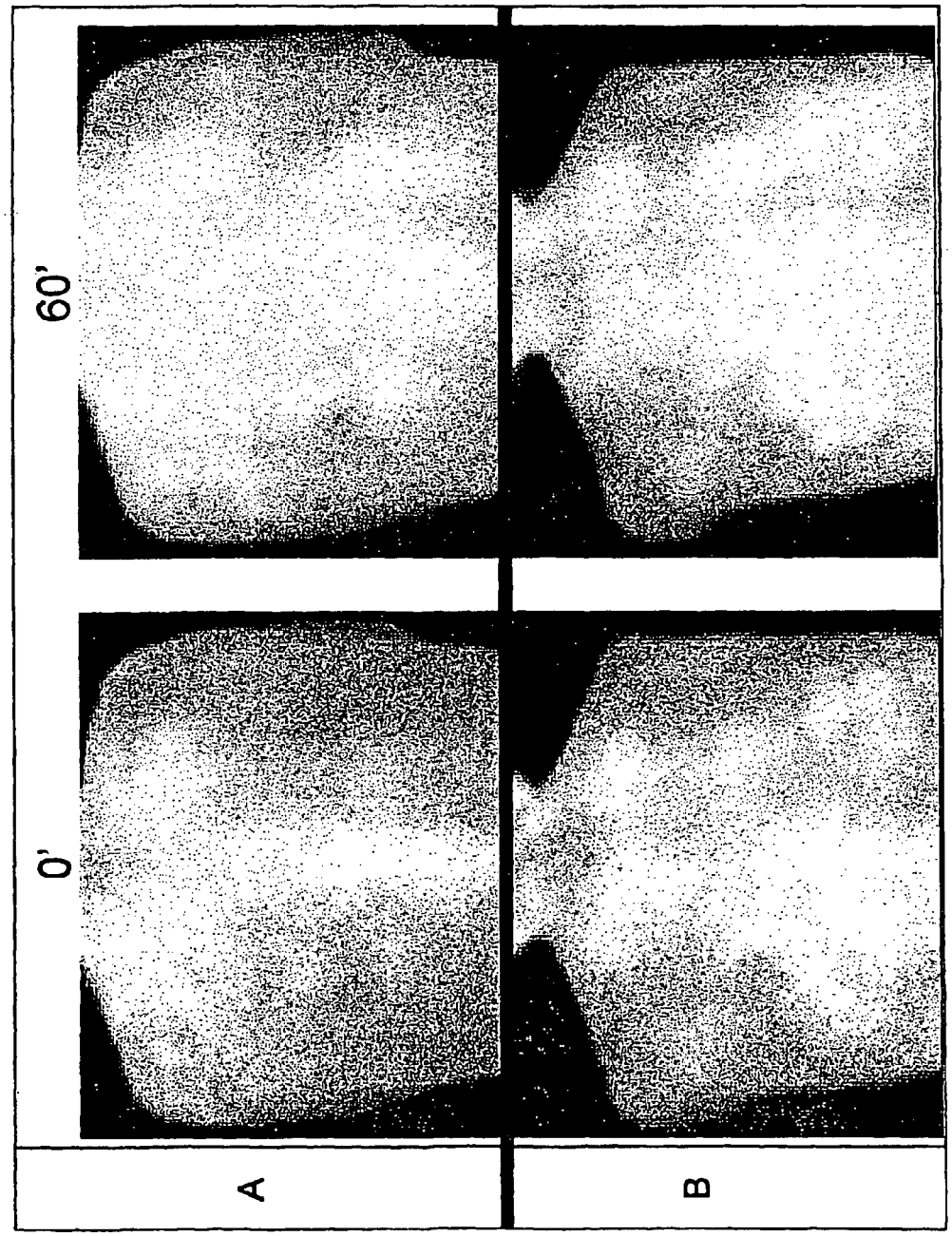
FIG. 19. Presentation of infrared thermographic analysis of drug-induced thermogenesis in humans (subject A and subject B) treated with ephedrine (left=0 minutes; right=60 minutes) (dose=0.6–0.7 mg/kg - delta T° C. (whole back= 0.63 for subject A and 0.46 for subject B)).

The effect of ephedrine on thermogenesis in two human subjects was detected by infrared imaging 60 minutes after treatment with ephedrine at a dose of 0.6–0.7 mg/kg. FIG. 19 is a thermal image demonstrating the thermogenic response induced by ephedrine in subjects A and B (Delta T° C.=0.63 and 0.46, respectively). Thus, infrared thermography can be used as a non-invasive surrogate assay to evaluate the efficacy, potency, pharmacokinetics, pharmocodynamics of drugs in clinical studies.

Example 18
Infrared Thermography of Drug-Drug Interactions in db/db Mice

The outcomes of pharmacodynamic drug-drug interactions are diverse and may range from potentially life-threatening situations to life saving therapies. As such, there is a great need to identify methods for rapid evaluation of drug interactions. Given a number of drugs alter metabolic rate, it was postulated there may be additive, subtractive, and/or synergistic effects of various agents on heat production in cell culture and/or in animals. Thus, it was of interest to determine if infrared thermography could be used to analyze the effects of mixing different agents on thermogenesis in vivo. Again, infrared thermography can be used to identify, rank order the efficacy, potency and toxicity of combination therapies in both pre-clinical and clinical studies.

Figure 20:
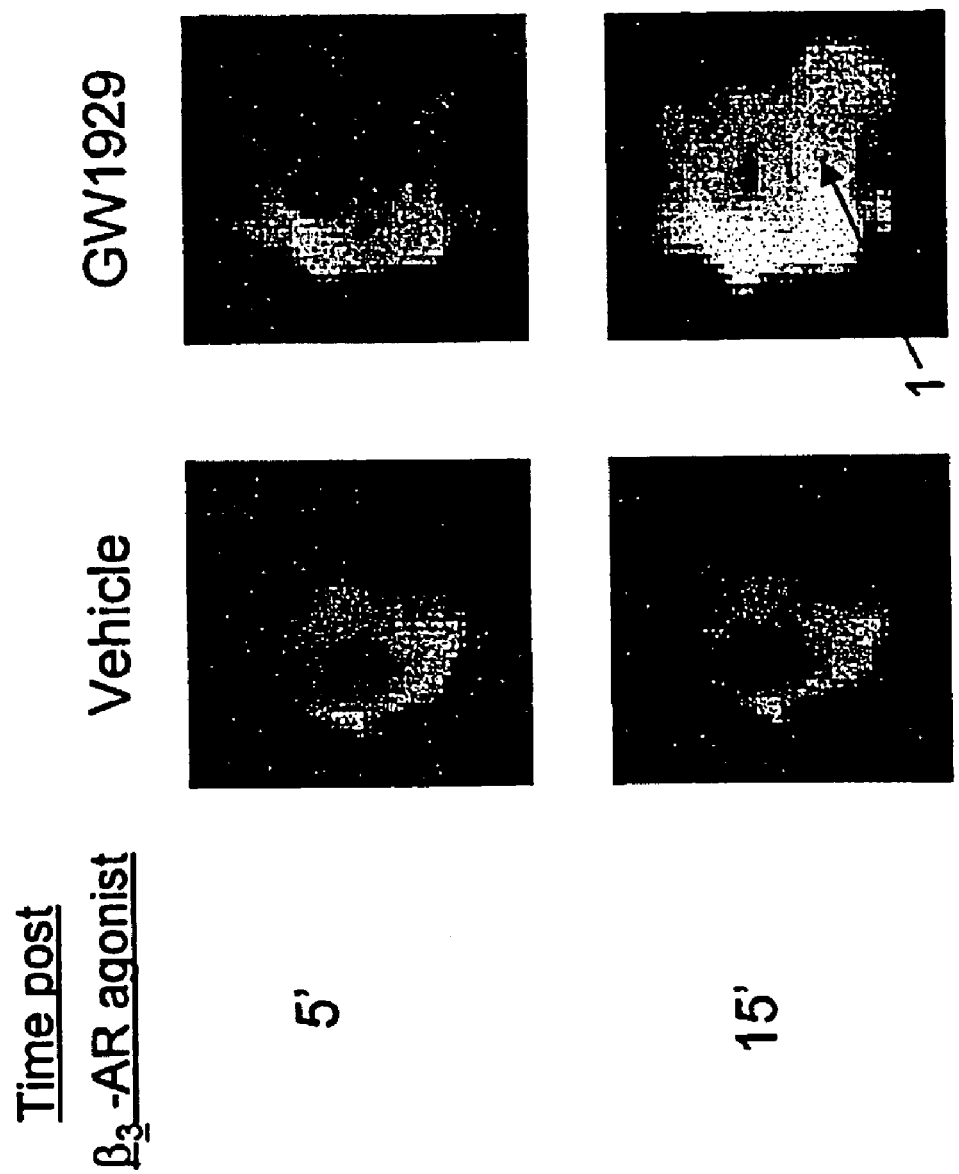
FIG. 20. Infrared thermographic characterization of interactions between two drugs, the β3-AR agonist CGP12177 (1 mg/kg-I.P.) and the PPARγ agonist GW1929, that influence interscapular thermogenesis in ob/ob mice (1=interscapular region).

GW1929 is an agent that improves glycemic control in diabetic animals by activating transcriptional activity of the ligand-activated nuclear receptor PPARγ. CGP12177A is an anti-obesity agent that acts via stimulation of the cell-surface $\beta_3$-adrenoceptor (Kenakin, Lenhard and Paulik, Curr Prot Pharm; 1(unit 4.6):1–36 (1998)). Since many diabetic patients are obese, it was of interest to determine if these two agents (i.e., GW1929 and CGP12177A) had any pharmacodynamic interactions. Thus, db/db mice were treated for 2 weeks with or without GW1929. At the end of the study, the animals were treated with or without CGP12177A and the heat produced in the interscapular region was measured using infrared thermography. As shown in FIG. 20, there was a greater thermogenic response in animals treated with both GW1929 and CGP12177A than either agent alone. Thus, these results validate using infrared thermography to measure how pharmacodynamic drug-drug interactions alter heat production.

Example 19
Thermographic Analysis of Tissue Vascularization by VEGF

Tumors are actively growing and metabolizing regions of tissue supported by local vascularizaton that enhances the tumor growth potential. Thermography can detect tumor-associated increases in thermogenesis, including those associated with tissue vascularization. Vascular endothelial growth factor (VEGF) is found in tumor tissue and its presence is associated with increased thermogenesis in the tissue in which it is localized. Thus, a nude mouse model was used that has its epidermal vasculature exposed to demonstrate the usefulness of thermography in tumor detection and vascularization. Nude mice were injected with either VEGF peptide or a control followed by themographic imaging of both injection sites. FIG. 21 shows thermographic images that demonstrate enhanced thermogenesis in the local area of the VEGF injection, but not in the local area of the control injection. Thus, infrared imaging can be used to monitor the effects of agents that alter tissue vascularization.

Example 20
Monitoring Tumor Temperature by Infrared Thermography

Tumor temperature is an indicator of the metabolic rate in the tumor. Tumors are dependent on the presence of VEGF for maximum metabolic activity and tumor temperature reflects changes in the availability of VEGF. This relationship is demonstrated by thermographic analysis of tumor-bearing mice treated with either an anti-VEGF antibody or a nonspecific anti-IgG antibody. FIG. 22 shows quantitative thermographic analysis demonstrating that tumor temperature decreases when VEGF is neutralized by the presence of anti-VEGF antibody. Thus, infrared imaging can be used to monitor the effects of anti-cancer therapies and as an aid in anti-cancer drug development.

Example 21
Monitoring Alopecia (Hair-Loss) by Infrared Thermography

Figure 23A:
FIGS. 23A and 23B. Infrared thermographic analysis of the effect of etoposide treatment (6 mg/kg) in utero on hair loss in newborn mouse pups.
Figure 23B:
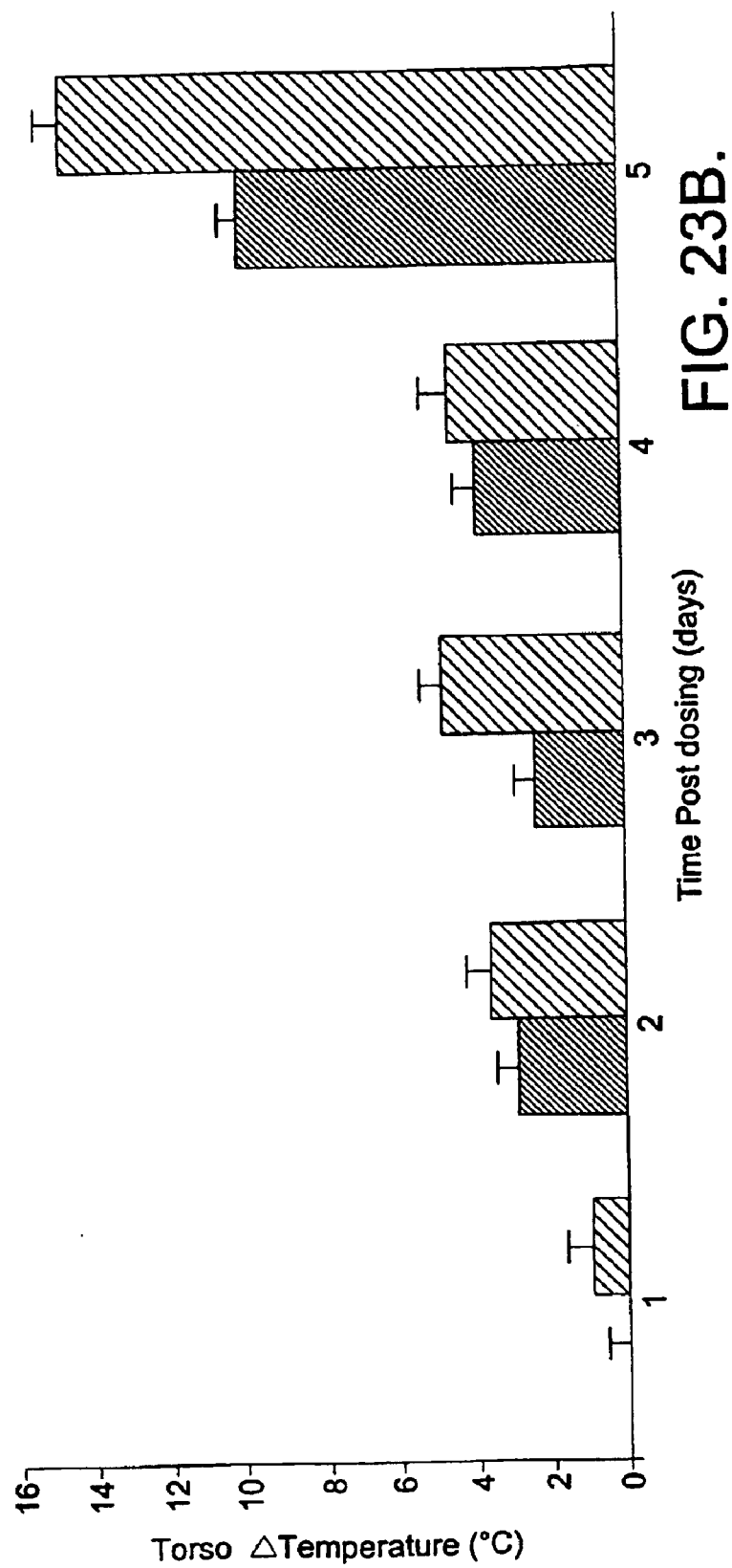

Hair loss can result from undesirable side-effects of various therapies (e.g., radiation treatment of cancer patients, surgery etc.) and can occur naturally with age, whereas surgical or pharmacological intervention can restore hair growth. Since hair provides insulation against heat loss and aids in the maintenance of a constant body temperature, it was of interest to determine if infrared thermography can be used to measure hair loss. The lack of progress in the treatment and prevention of chemotherapy-induced alopecia is in part due to the lack of a reproducible animal model as well as a quantitative method to measure hair-loss. To determine if infrared imaging can be used to quantitatively measure chemotherapy induced hair-loss, newborn rat pups that were treated in utero with the known cancer agent, etoposide, were thermally profiled for hair-loss. FIG. 23 shows thermal images (FIG. 23A) and quantitative analysis (FIG. 23B) demonstrating increased thermal activity in both the fronts and backs as a result of hair-loss. Thus, these results validate using infrared thermography to measure hair-loss as a method to aid in identifying therapies for alopecia and hair-loss in general or to identify agents that can cause hair-loss as an adverse reaction (e.g. a toxicity screen).

Example 22
Thermography After Drug Treatment for Male Erectile Dysfunction

Figure 24:
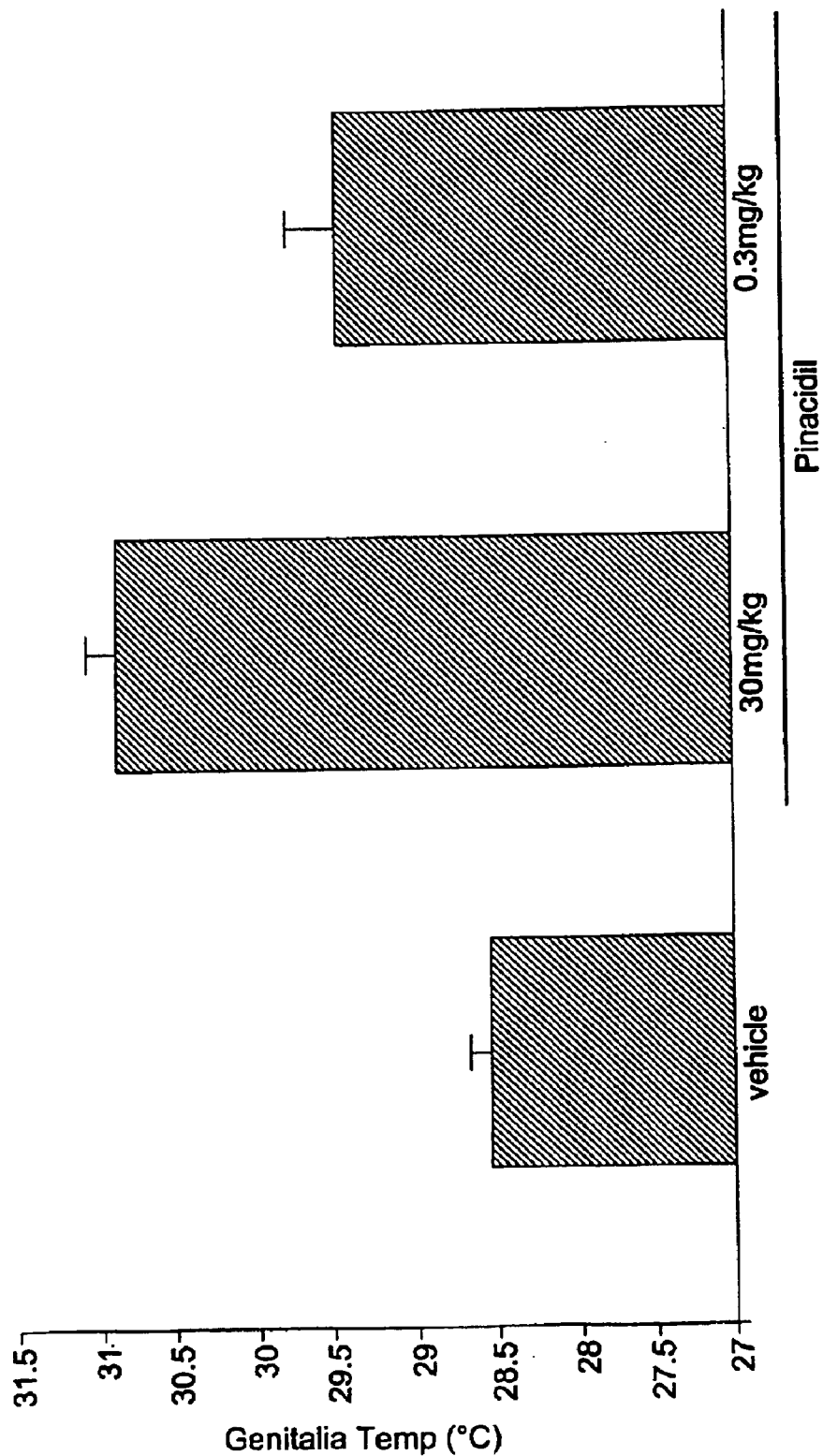
FIG. 24. Infrared thermographic analysis of Pinacidil-induced changes in thermogenesis in rat genitalia (2 hours post PO dosing).

Male erectile dysfunction (MED) is treatable with drugs that increase blood flow to the genitalia. Increased local thermogenesis is associated with increased local blood flow. One drug that acts in this manner and treats MED is Pinacidil. FIG. 24 shows that infrared thermography detects a Pinacidil-induced increase in thermogenesis in the genitalia of rats 2 hours after dosing with either 3.0 or 0.3 mg Pinacidil/kg. Thus, infrared thermography provides a quantitative and non-invasive method for identifying and evaluating drug candidates for the MED indication as well as identifying candidates that can cause erection as a side effect.

Example 23
Monitoring the Effect of Antiinflammatory Agents by Thermography

Figure 25A:
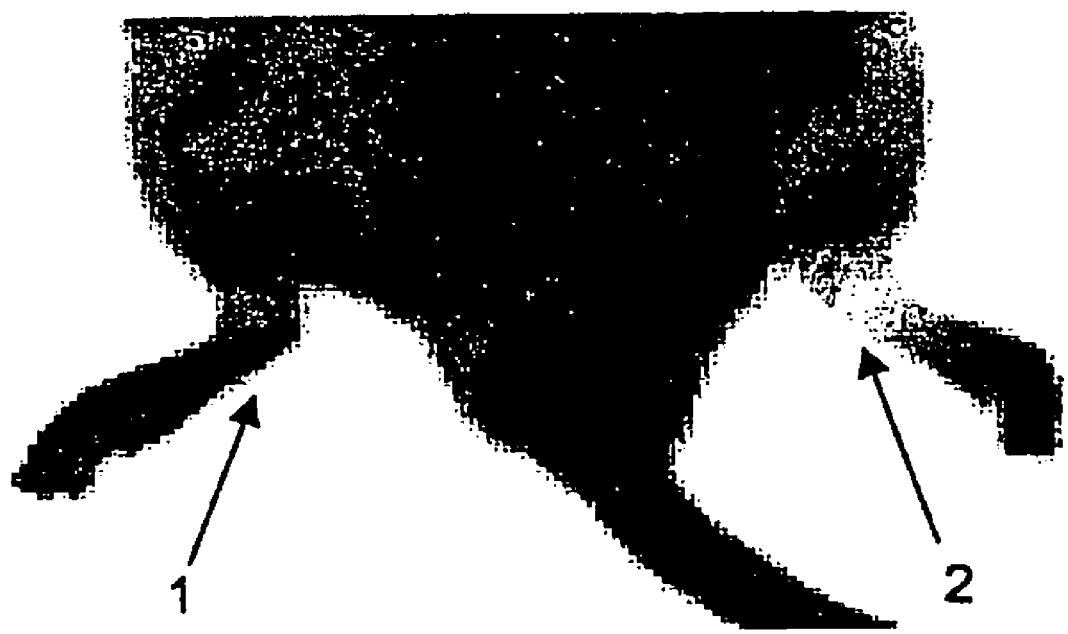
FIGS. 25A and 25B. Infrared thermographic analysis of limb inflammation induced by proteoglycan polysacharride (PGPS) (FIG. 25A; 1=non-arthritic limb; 2=arthritic limb) and reduced by 6 mg/kg p.o. prednisolone (FIG. 25B) (Vehicle=HPMC+0.1% TW80; p.o.).
Figure 25B:
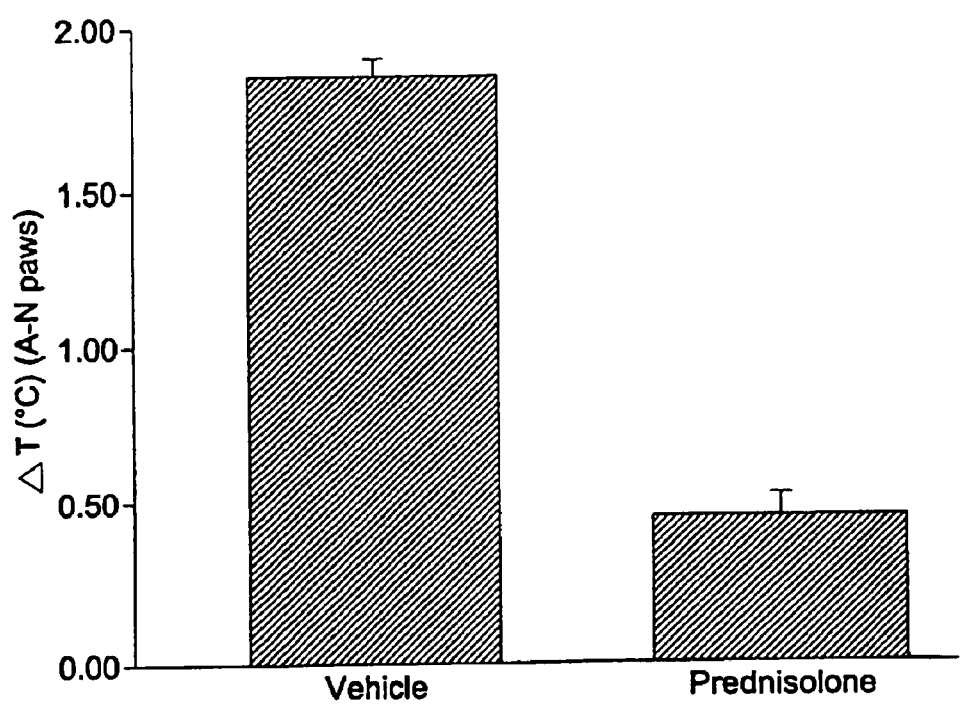

Arthritis is a disease characterized by inflammation of the joints and can be treated with antiinflammatory agents. Because inflammatory responses are associated with increased thermogenesis at the site of the response, arthritis and the efficacy of arthritis drugs can be monitored by thermography. To demonstrate this application, an arthritis model was established by injecting one limb of a normal animal with peptidoglycan polysaccharide (PGPS) for two weeks. The other limb was not treated. Infrared thermography on both limbs after the arthritis-inducing treatment demonstrates a higher level of thermogenesis in the treated limb than in the untreated limb (FIG. 25A) indicating infrared thermography can be used to monitor the ability of agents to cause inflammation. Subsequent treatment with the antiinflammatory agent prednisolone reverses the elevation in thermogenesis, such that both limbs have similar thermographic profiles after treatment (FIG. 25B). Thus, infrared thermography is a useful tool for monitoring inflammatory responses and the efficacy of antiinflammatory agents as well as providing a method for screening, selecting and evaluating the effectiveness of drug candidates for treating arthritic indications.

Example 24
IR Analysis of Internal Organs Utilizing an IR Transparent Polymer

Figure 26A:
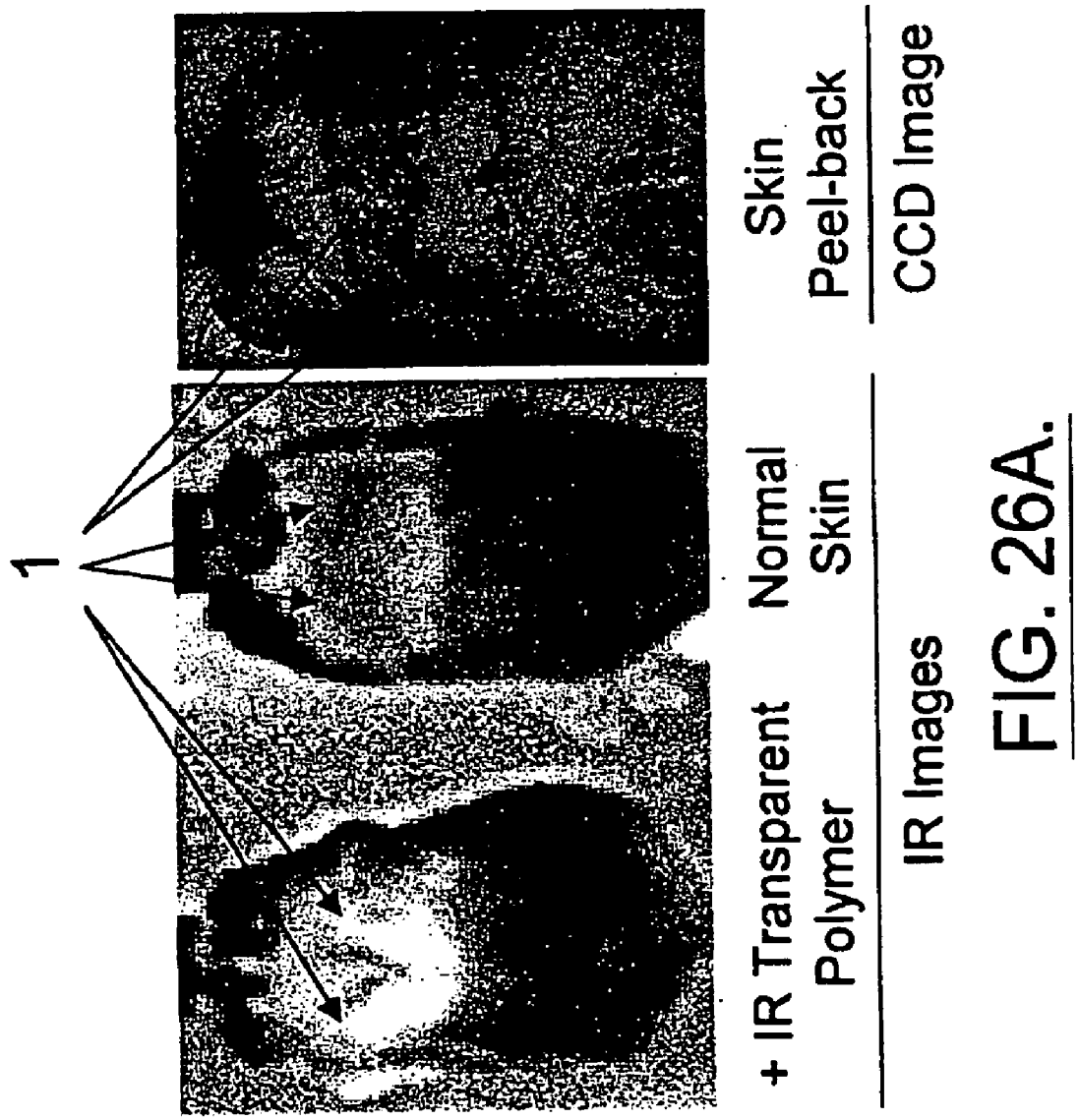
FIGS. 26A and 26B. Infrared thermographic analysis of the interscapular regions of mice whose skin was removed and IR transparent polymer placed over the IBAT after treatment with the $\beta_3$-adrenoceptor agonist (FIG. 26A).
Figure 26B:
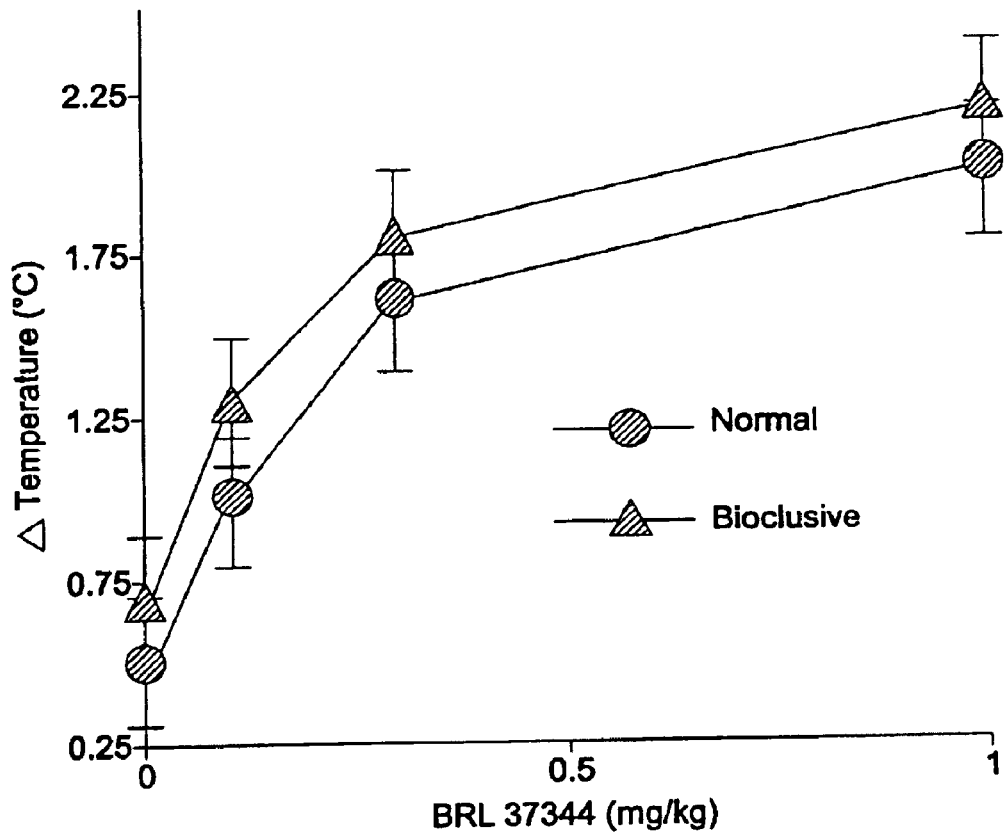

Since IR thermography measures surface temperatures, theoretically removing the skin covering IBAT should enable direct subcutaneous measurements. However, removal of skin exposes tissue to environmental influences resulting in uncontrolled evaporation and heat dissipation. In order to overcome these undesirable effects, exposed tissue was covered with an IR transparent polymer. FIG. 26A shows that the replacement of skin with an IR transparent polymer improved the resolution of the butterfly-shaped IBAT compared with shaved mice where measurements were made transdermally ("Normal Skin"). Importantly, mice with the IR transparent polymer and "Normal Skin"

mice demonstrated nearly identical dose-responses to the β$_3$-AR agonist BRL37344 (r$^2$=0.99, p<0.003) (FIG. 26B). These results support the hypothesis that subsurface thermal imaging of internal organs using an IR transparent dressing provides increased tissue delineation (IR image vs. CCD image) without affecting physiological responsiveness.

Example 25

Figure 27A:
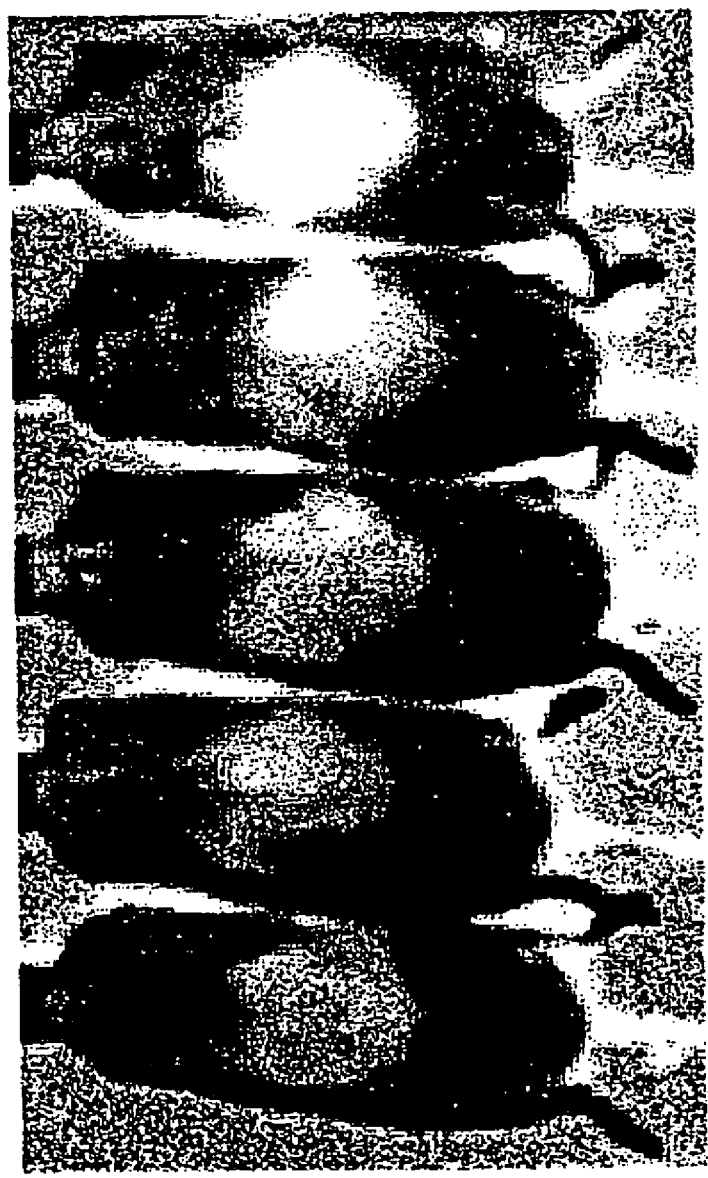
FIGS. 27A, 27B and 27C. Infrared analysis visualized with the IR transparent polymer of liver thermogenesis in ob/ob mice 90 min after glucose treatment (FIG. 27A).
Figure 27B:
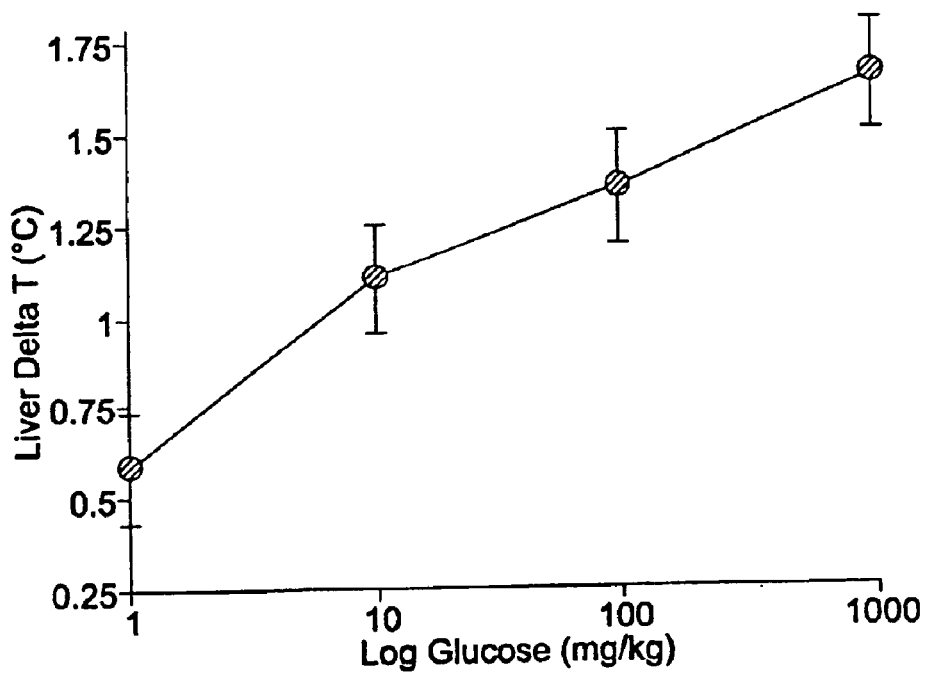
Figure 27C:
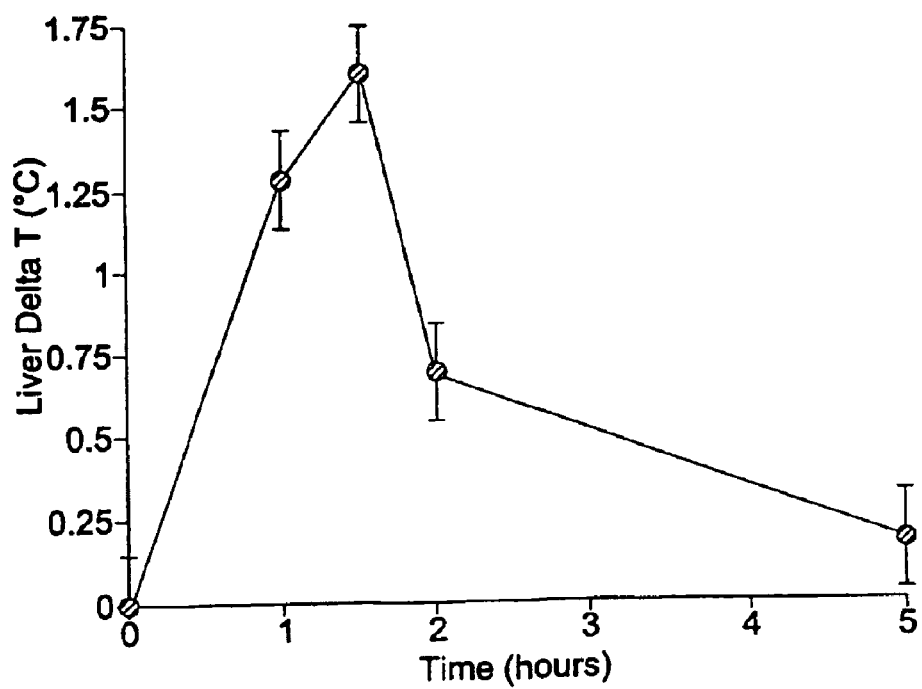

Metabolism-Induced and Drug-Induced Changes in Liver Thermogenesis can be Measured using IR Thermography To determine if the IR transparent polymer could be used to thermally image internal organs, glucose was administered to stimulate hepatic metabolism in fasted ob/ob mice. The IR polymer was placed over the surgically exposed liver 90 min after treatment. As shown in FIG. 27A, mice orally dosed with glucose demonstrate a dose-dependent increase in liver thermogenesis 90 min after treatment (FIGS. 27A and 27B). Moreover, treatment with 1 g/kg glucose resulted in a time-dependent increase in liver thermogenesis, which peaked at 90 min and returned to control levels 5 h after treatment (FIG. 27C). Measurements of body core temperature using rectal probes revealed only slight increases in body core temperature in glucose-treated animals (0.25° C., p=0.4 (ANOVA)), indicating that most of the increase in thermogenesis was liver-specific. These data demonstrate the effectiveness of an IR transparent polymer for measuring basal metabolic activities in the liver.

Figure 28A:
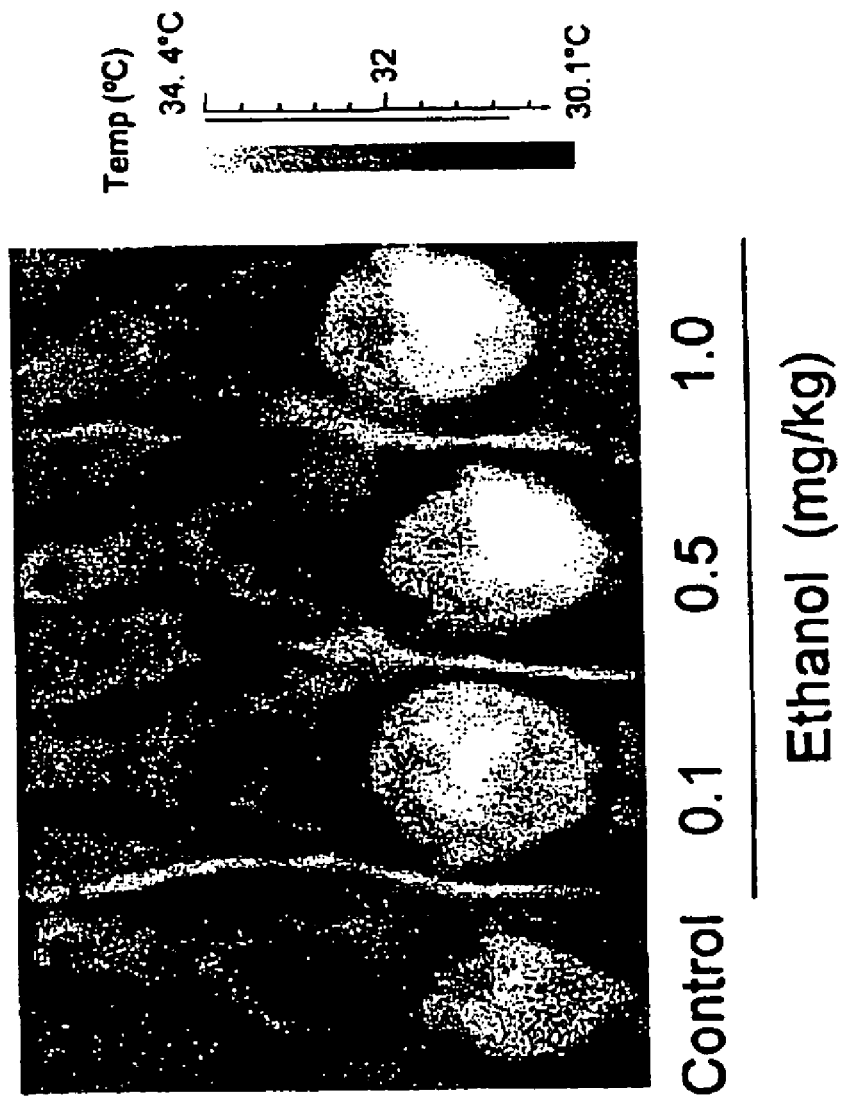
FIGS. 28A and 28B. Liver thermogenesis detected by IR thermography using the IR transparent polymer in rats treated with ethanol for 5 days.
Figure 28B:
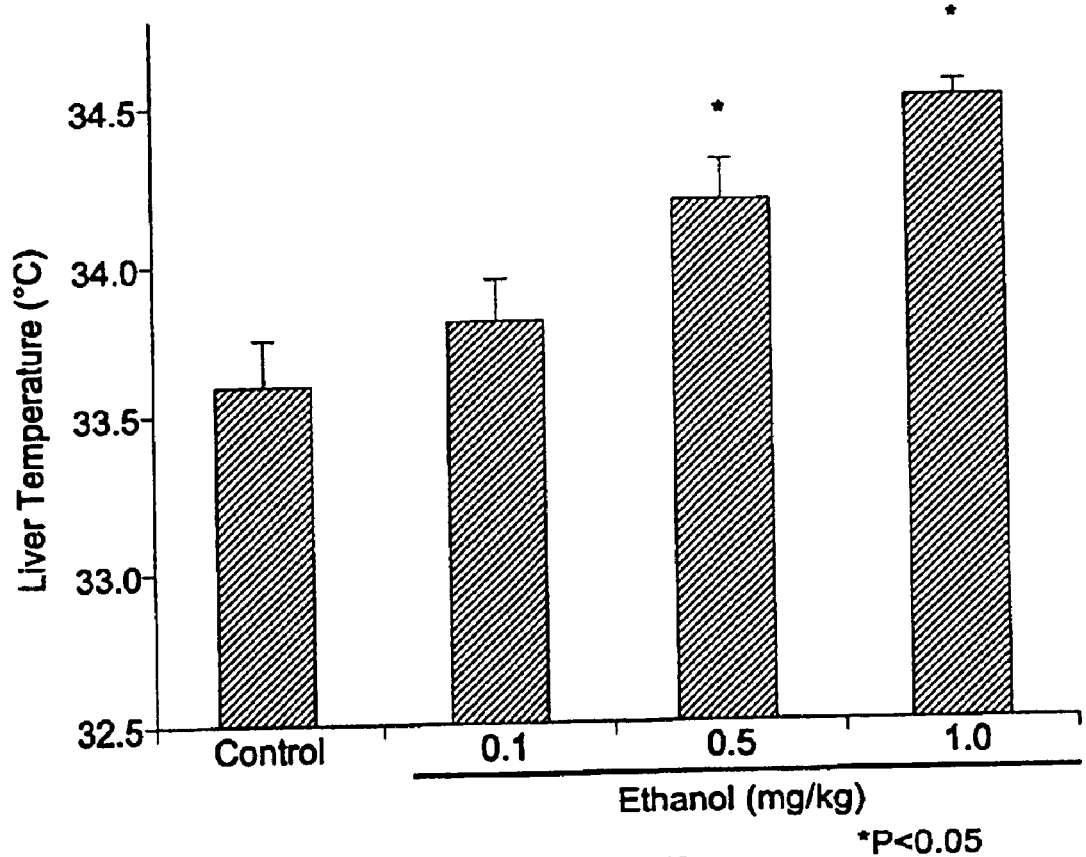

We further explored the possibility that this novel method of imaging internal organs would be useful for measuring and predicting hepatotoxicity. To test this hypothesis, female Sprague-Dawley rats were treated with the ethanol twice daily for 4 days and Bioclusive polymer placed over surgically exposed liver on day 5. The results indicate that ethanol caused a dose-dependent increase in liver thermogenesis (FIGS. 28A and 28B). Core body temperature measured using rectal probes was not changed in ethanol-treated rats (p=0.08 (ANOVA)). While classical markers of liver toxicity, serum aspartate aminotransferase (AST) and alanine aminotransferase (ALT), were not increased above control levels (AST, p=0.3; ALT, p=0.4 (ANOVA)). However, UCP2 mRNA expression correlated well (r=0.95, p<0.01) with liver thermogenesis, increasing almost 2-fold in animals treated with 1 g/kg ethanol twice each day for 5 days. These findings are in excellent agreement with recent studies that demonstrated a 2-fold increase in UCP2 mRNA expression in mice receiving ethanol treatment for 4 weeks (Rashid et al., *Hepatology* 29(4):1131–8 (1999)).

Classical measures of ethanol-induced hepatotoxicity include steatosis (fatty liver), increased serum transaminases (AST and ALT), fibrosis and cirrhosis. In order to achieve measurable increases in these parameters, rats must be fed specialized high-fat diets in combination with ethanol treatment for 4–8 weeks (Zhong et al., *Transplantation Proceedings.* 27(1):528–30, (1995); Tsukamoto et al, *Am J Physiol* 247 R595–R599, (1984)). Whereas, in these studies rats were only administered ethanol and detectable increases in liver thermogenesis were detected in 5 days. Taken together, these studies demonstrate that IR thermography is more sensitive than classical markers for detecting ethanol induced hepatotoxicity and thus can be used as an early indicator of liver toxicities.

Figure 29B:
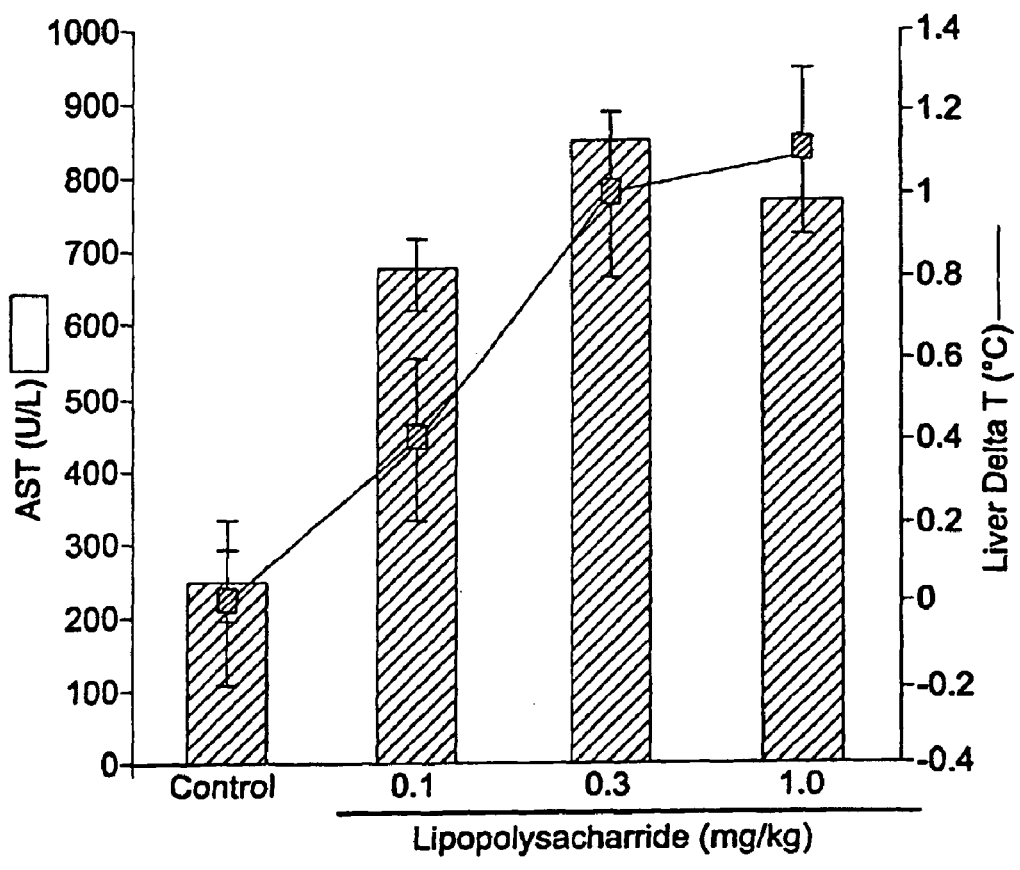

Interestingly, recent evidence indicates that gut-derived endotoxin (lipopolysaccharide or LPS), which is a component of the cell wall of Gram-negative bacteria, participates in alcoholic liver injury (Thurman et al., *Am J Physiol,* 275 G605–G611 (1998)). To test the hypothesis that LPS stimulates liver thermogenesis, ob/ob mice were treated with increasing doses of LPS and IR images of their livers acquired 90 min after treatment. As shown in FIGS. 29A and 29B, thermogenesis increased in animals treated with LPS in a dose-dependent manner. In addition, LPS treatment is known to cause increases in TNFα and UCP2 expression (Cortez-Pinto et al., *Biochem Biophys Res Commun* 251(1):313–9 (1998); Faggioni et al., *Am J Physiol.* 276, R136–42, (1999)). These experiments demonstrated that LPS-induced thermogenesis correlated well with both TNFα and UCP2 mRNA expression (r=0.78, p<0.001 and r=0.77, p<0.01, respectively). However, serum levels of aspartate aminotransferase (AST) and alanine aminotransferase (ALT), classical markers of LPS-induced hepatocyte necrosis, were unchanged 90 min after LPS treatment (ALT, p=0.94; AST, p=0.38 (ANOVA)). Similarly, histopathological examination did not reveal inflammation or necrosis 90 min after LPS treatment, supporting the hypothesis that early metabolic changes, such as increased UCP2 activity, may be responsible for LPS-induced liver thermogenesis rather than inflammatory infiltrate or hepatic necrosis.

To determine if acute thermogenesis correlated with chronic liver injury, ob/ob mice were treated with LPS for 90 min and 10 h, respectively. Thermogenesis measured 90 min after treatment correlated with AST (FIG. 29B, r=0.91, p<0.01) and ALT (r=0.76, p<0.01) release 10 h after treatment. Moreover, histopathological examination of livers showed LPS caused a dose-dependent increase in hepatocyte apoptosis and hepatic necrosis, indicating that LPS-induced increases in thermogenesis precede hepatotoxicity.

Figure 30:
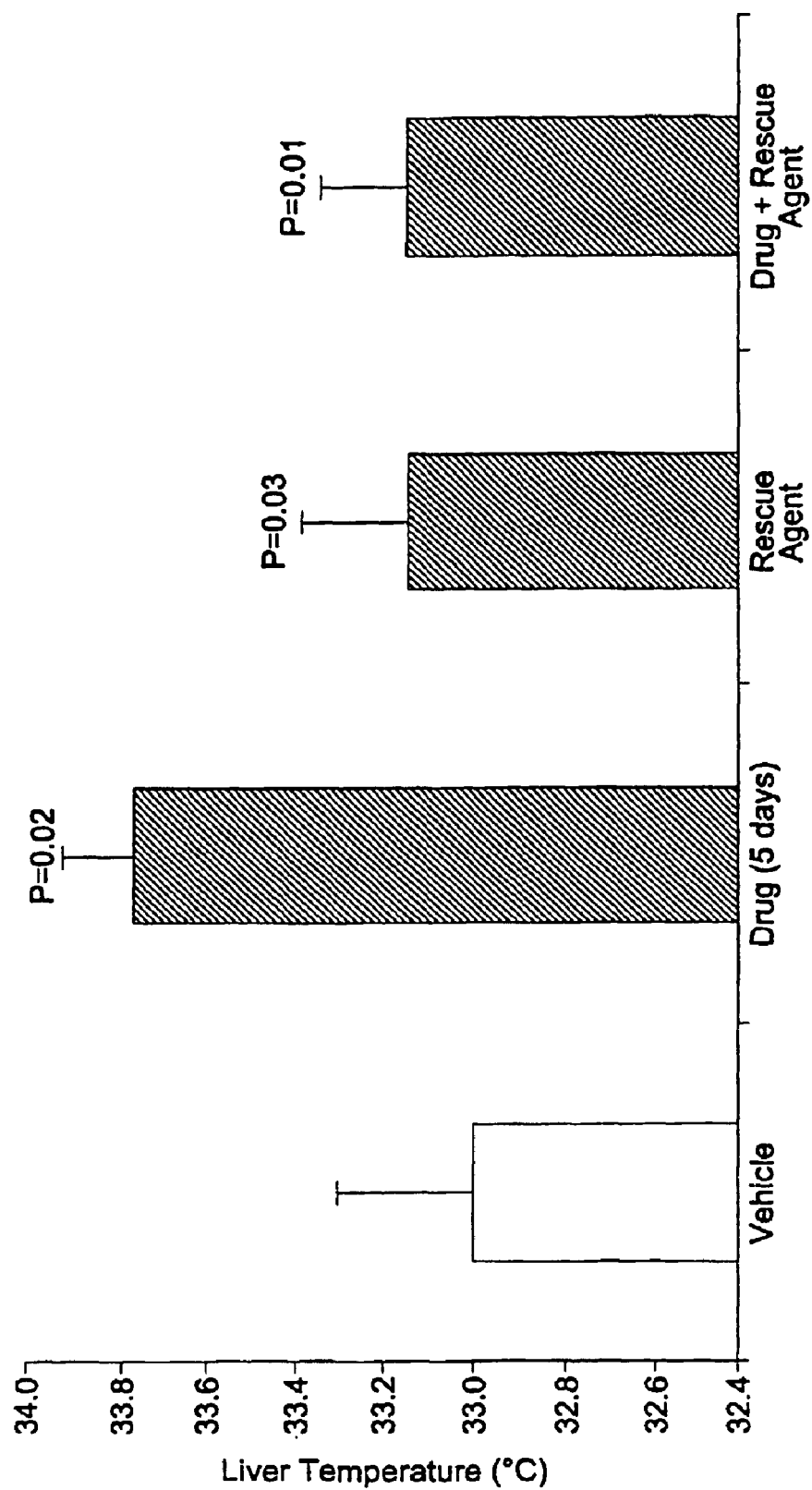
FIG. 30. Graph demonstrating the use of infrared thermography and the IR transparent polymer to profile liver thermogenesis of mice treated with d4T (drug) and/or antioxidants (rescue agent).

In order to further demonstrate utility of IR thermography for measuring liver toxicities and subsequent reversal of the toxicities, livers from mice treated with d4T, a nucleoside reverse transcriptase inhibitor, were thermally profiled in the presence and absence of rescue agent (ascorbate and α-tocopherol). It has been previously shown that administration of d4T to AKR mice induces metabolic changes (i.e. elevated lactate, transaminases and oxidative stress) in these animals. Furthermore, administration of antioxidants such as ascorbate and α-tocopherol reversed these effects. Therefore, to determine if IR thermography could be used to measure the d4T-induced toxicities and subsequent reversals with anti-oxidants, AKR mice were treated for 5 days with 50 mg/kg d4T (drug) and/or antioxidants (50 mg/kg ascorbate and α-tocopherol) (rescue agent) and livers were thermally profiled. Liver thermogenesis increased with d4T (drug) alone, whereas, d4T in the presence of antioxidants reversed the increase in thermogenesis (FIG. 30). The changes measured in liver thermogenesis with d4T in the presence and absence of antioxidants are consistent with the changes measured by both serological endpoints (i.e. serum lactates) and genetic endpoints (i.e. changes in oxidative stress and liver metabolism genes). However, it takes at least 2 weeks until measurable changes in the serological and gene expression endpoints occur. Therefore, these studies further demonstrate that IR thermography is more sensitive than classical markers for detecting drug-induced hepatotoxicity and thus can be used as an early indicator of liver toxicities. Taken together, these data are consistent with the hypothesis that IR thermography of internal organs, such as the liver, measures acute drug-and/or metabolite-induced changes in metabolic activity.

Example 26

IR Thermography as a Clinical Surrogate/Diagnostic for Lipodystrophy

Figure 31:
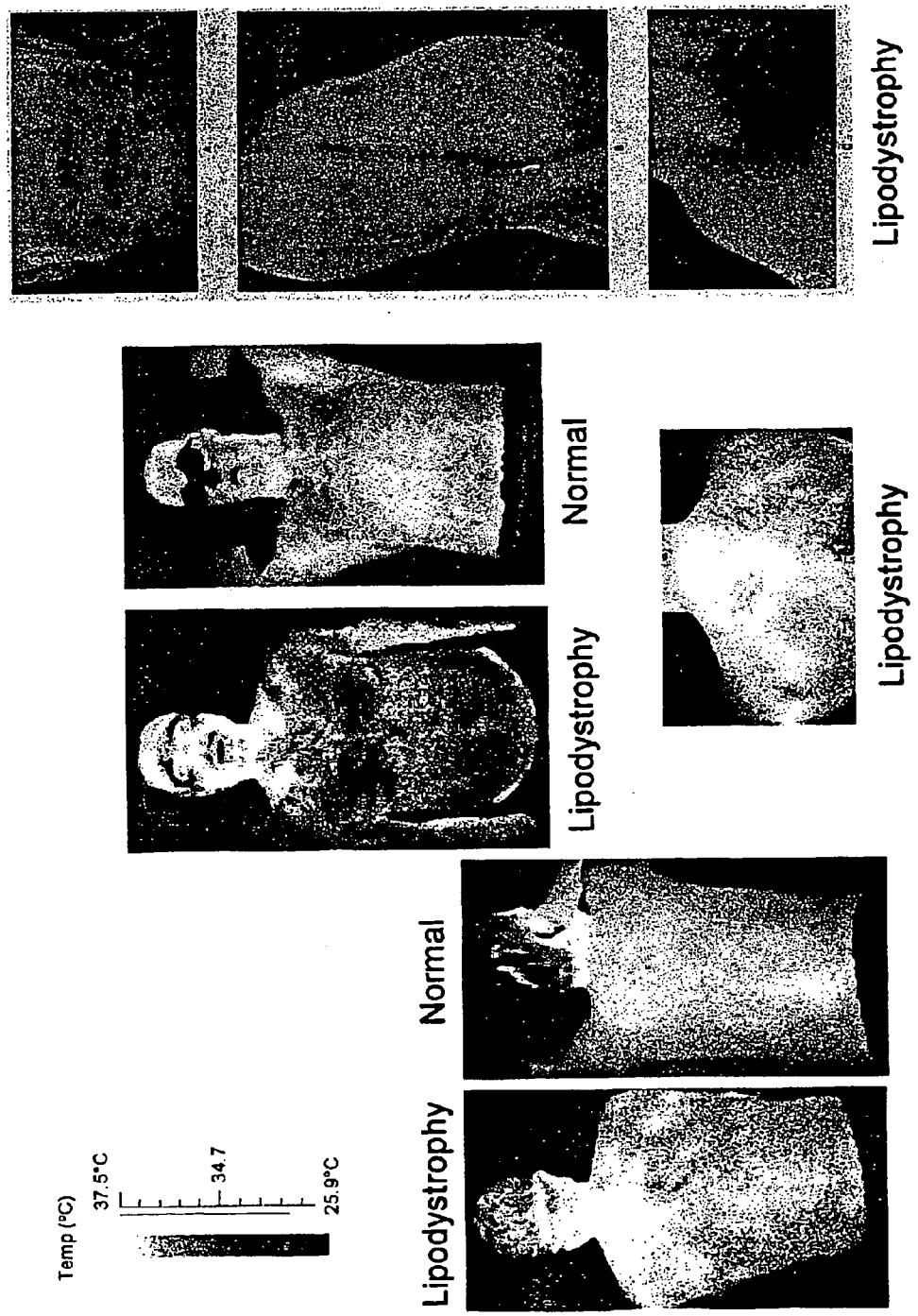
FIG. 31. Thermography of HIV patient suffering from lipodystrophy vs. normal subject. A distinctive thermal profile, particularly of the face, where fat wasting is occurring, and the back of the neck, is visualized by IR thermography.

IR thermography has significant potential for applications involving human subjects. To evaluate this potential, case studies were carried out on subjects displaying alterations in metabolic activity. Body shape and metabolic changes associated with the use of retroviral therapies are causing increasing concern among physicians who treat patients with HIV/AIDS. These changes in metabolism are due to a lipodystrophy syndrome which is characterized by an increase in abdominal fat and loss of subcutaneous adipose depots (Carr A., et al. Lancet 353, 2093–2099 (1999)). Since these symptoms reflect alterations in metabolic activity, IR thermography may provide a non-invasive method to screen patients for alterations in metabolic activity based on their thermal profile. Therefore, to test the use of IR thermography as a surrogate marker for lipodystrophy, a case study was done comparing the thermal profile of a normal patient and an AIDS patient diagnosed with lipodystrophy who was receiving HIV therapy. FIG. 31 shows dramatic differences in the thermal profiles of a normal individual compared to the HIV patient. The changes in thermal pattern are consistent with the changes in metabolic activity of the patient's torso (i.e. fat wasting in the face=increased thermogenesis; fat redistribution in the belly=decreased thermogenesis). Taken together, this case study suggests that IR thermography may be used as a clinical surrogate for diagnosing and monitoring the progression of lipodystrophy. The information provided by IR thermography may enable physicians to prescribe and/or after their patients therapy accordingly.

Example 27

IR Thermography as a Clinical Surrogate/Diagnostic for Psoriasis

Figure 32:
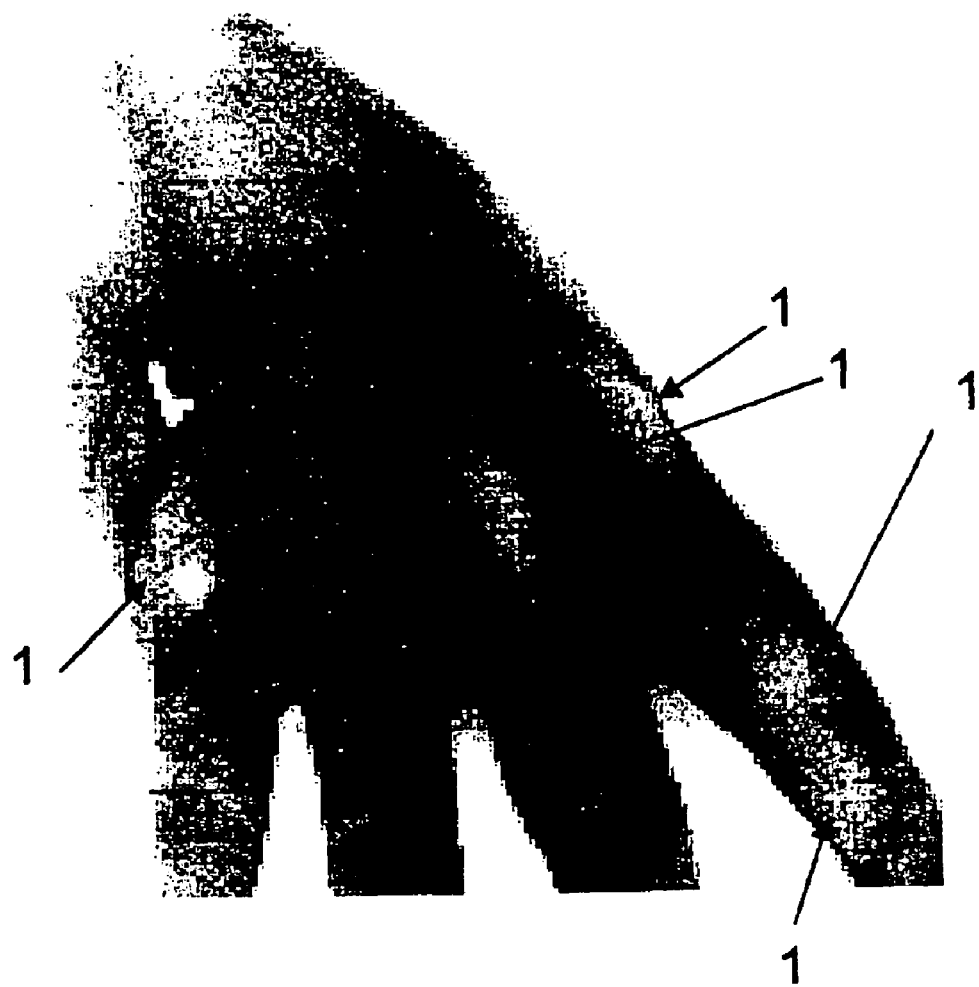
FIG. 32. IR thermography of a patient suffering from psoriasis. The thermally distinct areas (arrows, 1) are profiling in the exact same areas as the psoriatic lesions.

Psoriasis is thought to occur as a result from over expression of the EGF/EGFR systems resulting in disregulation of keratinocyte growth and epidermal hyperplasia (Elder JT et al., *Science* (1989)). One of the primary therapies for psoriasis, the combination of psoralens and UVA light, known as PUVA, has been shown to be a potent inhibitor of EGF cell binding and EGFR tyrosine kinase activity (Laskin JD et al., *Proc. Nat.l Acad. Sci. USA*, (1986)). The psoriasis symptoms of uncontrolled cell growth and epidermal hyperplasia may be reflected as alterations in metabolic activity at the skin surface. Thus, based on their thermal profile, IR thermography may provide a non-invasive method to screen patients for alterations in metabolic activity (i.e. psoriatic plaques). Therefore, to test the hypothesis that IR can be used as a clinical surrogate for Psoriasis, a case study was done thermally profiling a subject diagnosed with Psoriasis. FIG. 32 shows differences in thermal pattern of the psoriatic lesions (arrows, 1). The changes in thermal pattern are consistent with the changes in metabolic activity of the patient's psoriatic lesions (i.e. increased hyperplasia= increased thermogenesis, FIG. 32 (1)). Taken together, this case study suggests that IR thermography may be used as a clinical surrogate for diagnosing and monitoring the progression of Psoriasis. The information provided by IR thermography may enable physicians to diagnose as well as prescribe and/or alter their patient's therapy accordingly.

All documents cited above are hereby incorporated in their entirety by reference.

One skilled in the art will appreciate from a reading of this disclosure that various changes in form and detail can be made without departing from the true scope of the invention.

What is claimed is:

1. A method of diagnosing lipodystrophy in a body region in a test subject in vivo comprising measuring the temperature of the body region using infrared thermography, a raise in temperature relative to the same body region in a normal subject indicating the presence of lipodystrophy in the subject.

2. The method of claim 1, wherein the body region is the face.

3. The method of claim 1, wherein the body region is the back of the neck.

4. The method of claim 1, wherein the subject is HIV-positive.

5. The method of claim 1, wherein the patient has previously been treated with protease inhibitors.

* * * * *

SEQUENCE LISTING

<160> NUMBER OF SEQ ID NOS: 4

<210> SEQ ID NO 1
<211> LENGTH: 40
<212> TYPE: DNA
<213> ORGANISM: Artificial Sequence
<220> FEATURE:
<223> OTHER INFORMATION: Primer

<400> SEQUENCE: 1
aaaaaacccc ggatcgaatt catggttggg ttcaaggcca                    40

<210> SEQ ID NO 2
<211> LENGTH: 47
<212> TYPE: DNA
<213> ORGANISM: Artificial Sequence
<220> FEATURE:
<223> OTHER INFORMATION: Primer

<400> SEQUENCE: 2
cattgttcct tattcagtta ctcgagttag aagggagcct ctcggga            47

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
ttaacgtcaa ggagaaaaaa ccccggatcg                               30

-continued

```
<210> SEQ ID NO 4
<211> LENGTH: 32
<212> TYPE: DNA
<213> ORGANISM: Artificial Sequence
<220> FEATURE:
<223> OTHER INFORMATION: Primer

<400> SEQUENCE: 4
gaaaggaaaa acgttcattg ttccttattc ag                           32
```